United States Patent
Artinger et al.

(10) Patent No.: US 12,339,283 B2
(45) Date of Patent: *Jun. 24, 2025

(54) FLOW CYTOMETRY EVALUATION OF BIOLOGICAL MATERIAL FOR UNASSOCIATED VIRUS-SIZE PARTICLES

(71) Applicant: Sartorius BioAnalytical Intruments, Inc., Bohemia, NY (US)

(72) Inventors: Michael A. Artinger, Boulder, CO (US); Francis Kevin Kohlmeier, Broomfield, CO (US); Michael W. Olszowy, Erie, CO (US); Tyler Donald Gates, Longmont, CO (US)

( * ) Notice: Subject to any disclaimer, the term of this patent is extended or adjusted under 35 U.S.C. 154(b) by 11 days.

This patent is subject to a terminal disclaimer.

(21) Appl. No.: 18/052,661

(22) Filed: Nov. 4, 2022

(65) Prior Publication Data
US 2023/0147597 A1 May 11, 2023

Related U.S. Application Data

(63) Continuation of application No. 16/781,382, filed on Feb. 4, 2020, now Pat. No. 11,585,813, which is a continuation of application No. 15/713,314, filed on Sep. 22, 2017, now Pat. No. 10,585,030, which is a continuation of application No. 15/558,107, filed as application No. PCT/US2016/023737 on Mar. 23, 2016, now Pat. No. 10,161,850.

(60) Provisional application No. 62/280,042, filed on Jan. 18, 2016, provisional application No. 62/280,079, filed on Jan. 18, 2016, provisional application No. 62/280,029, filed on Jan. 18, 2016, provisional application No. 62/280,048, filed on Jan. 18, 2016, provisional application No. 62/273,874, filed on Dec. 31, 2015, provisional application No. 62/137,102, filed on Mar. 23, 2015.

(51) Int. Cl.
| | |
|---|---|
| G01N 33/569 | (2006.01) |
| C12N 7/00 | (2006.01) |
| G01N 15/06 | (2006.01) |
| G01N 15/14 | (2006.01) |
| G01N 15/1434 | (2024.01) |
| G01N 21/64 | (2006.01) |
| G01N 33/533 | (2006.01) |
| G01N 33/58 | (2006.01) |
| G01N 15/01 | (2024.01) |
| G01N 15/075 | (2024.01) |

(52) U.S. Cl.
CPC ......... *G01N 33/56983* (2013.01); *C12N 7/00* (2013.01); *G01N 15/06* (2013.01); *G01N 15/14* (2013.01); *G01N 15/1436* (2013.01); *G01N 15/1459* (2013.01); *G01N 21/6428* (2013.01); *G01N 33/533* (2013.01); *G01N 33/582* (2013.01); *G01N 15/01* (2024.01); *G01N 2015/0687* (2013.01); *G01N 15/075* (2024.01); *G01N 2015/1486* (2013.01); *G01N 2015/1488* (2013.01); *G01N 2015/1493* (2013.01); *G01N 2021/6439* (2013.01); *G01N 2021/6441* (2013.01); *G01N 2333/11* (2013.01); *G01N 2469/10* (2013.01)

(58) Field of Classification Search
CPC .......... G01N 33/56983; G01N 33/533; G01N 33/582; G01N 15/01; G01N 15/06; G01N 2015/1486
See application file for complete search history.

(56) References Cited

U.S. PATENT DOCUMENTS

| | | | |
|---|---|---|---|
| 6,248,514 B1 | 6/2001 | Hutchins et al. | |
| 7,786,282 B2 | 8/2010 | Prussak et al. | |
| 8,003,314 B2 | 8/2011 | Scholl et al. | |
| 9,816,912 B2 * | 11/2017 | Artinger | G01N 15/14 |
| 10,031,061 B2 | 7/2018 | Rowlen et al. | |
| 10,101,262 B2 * | 10/2018 | Artinger | G01N 15/1459 |
| 10,161,850 B2 * | 12/2018 | Artinger | G01N 15/06 |
| 10,408,734 B2 * | 9/2019 | Artinger | G01N 33/56983 |
| 10,545,084 B2 * | 1/2020 | Artinger | G01N 15/1459 |
| 10,585,030 B2 * | 3/2020 | Artinger | G01N 33/582 |
| 10,705,007 B2 | 7/2020 | Rowlen et al. | |
| 10,739,246 B2 * | 8/2020 | Artinger | G01N 15/06 |
| 11,137,337 B2 | 10/2021 | Gates et al. | |
| 11,585,813 B2 * | 2/2023 | Artinger | G01N 15/06 |
| 11,709,116 B2 | 7/2023 | Montange et al. | |

(Continued)

FOREIGN PATENT DOCUMENTS

| | | |
|---|---|---|
| CN | 1563990 A | 1/2005 |
| CN | 102046815 A | 5/2011 |
| WO | 2014210370 A1 | 12/2014 |

OTHER PUBLICATIONS

Gaudin et al., "Sorting of Small Infectious Virus Particles by Flow Virometry Reveals Distinct Infectivity Profiles," Nature Communications, 6:6022 (Feb. 2, 2015 11 pages.

(Continued)

*Primary Examiner* — Gailene Gabel

(74) *Attorney, Agent, or Firm* — Holzer Patel Drennan

(57) ABSTRACT

A method for evaluating a biological material for unassociated virus-size particles having a particular epitope uses a fluorescent antibody stain specific for binding with the epitope and a fluid sample with the virus-size particles and fluorescent antibody stain is subjected to flow cytometry with identification of fluorescent emission detection events indicative of passage through a flow cell of a flow cytometer of unassociated labeled particles of virus size including such a virus-size particle and fluorescent antibody stain.

20 Claims, 16 Drawing Sheets

(56) References Cited

U.S. PATENT DOCUMENTS

| | | |
|---|---|---|
| 12,169,201 B2 | 12/2024 | Artinger et al. |
| 12,196,652 B2 | 1/2025 | Montange et al. |
| 2009/0022759 A1 | 1/2009 | Burgert et al. |
| 2009/0275107 A1 | 11/2009 | Lock et al. |
| 2012/0070818 A1 | 3/2012 | Rowlen et al. |
| 2015/0111776 A1 | 4/2015 | Chen |

OTHER PUBLICATIONS

Rossi et al., "Evaluation of ViroCyt Virus Counter for Rapid Filovirus Quantitation," Viruses, vol. 7, No. 3, (Feb. 20, 2015), pp. 857-872.

Arakelyan et al., "Nanoparticle-Based Flow Virometry for the Analysis of Individual Virions," Journal of Clinical Investigation, vol. 123, No. 9 (2013), pp. 3716-3727.

Reichmuth et al., "Rapid Microchip-Based Electrophoretic Immunoassays for the Detection of Swine Influenza Virus," Lab on a Chip, Miniaturisation for Chemistry, Physics, Biology, Materials Science and Bioengineering, vol. 8, No. 8, (2008), pp. 1319-1324.

Landowski et al., "Nipah Virion Entry Kinetics, Composition, and Conformational Changes Determined by Enzymatic Virus-Like Particles and New Flow Virometry Tools," Journal of Virology, vol. 88, No. 24 (2014), pp. 14197-14206.

Gates et al., "Quantitative Measurement of Varicella-Zoster Virus Infection by Semiautomated Flow Cytometry," Applied and Environmental Microbiology, vol. 75, No. 7 (2009), pp. 2027-2036.

Greve et al., "A New Affordable Flow Cytometry Based Method to Measure HIV-1 Viral Load," Cytometry Part A, 75A (2009), pp. 199-206.

Marie et al., "Enumeration of Marine Viruses in Culture and Natural Samples by Flow Cytometry," Applied and Environmental Microbiology, vol. 65, No. 1 (1999), pp. 45-52.

Schulze-Horsel et al., "Flow Cytometric Monitoring of Influenza A Virus Infection in MDCK Cells During Vaccine Production," BMC Biotechnology, 8:45 (2008), 12 pages.

Wunschmann et al., "Fluorescence-Based Quantitative Methods for Detecting Human Immunodeficiency Virus Type 1-Induced Syncytia," Journal of Clinical Microbiology, vol. 38, No. 8 (2000), pp. 3055-3060.

Hercher et al., "Detection and Discrimination of Individual Viruses by Flow Cytometry," Journal of Histochemistry and Cytochemistry, vol. 27, No. 1 (1979), pp. 350-352.

Stoffel et al., "Design and Characterization of a Compact Dual Channel Virus Counter," Cytometry Part A, 65A (2005), pp. 140-147.

Steen, Harald B., "Flow Cytometer for Measurement of the Light Scattering of Viral and Other Submicroscopic Particles," Cytometry Part A, 57A (2004), pp. 94-99.

Pospichalova et al., "Simplified protocol for flow cytometry analysis of fluorescently labeled exosomes and microvesicles using dedicated flow cytometer," Journal of Extracellular Vesicles (Mar. 31, 2015) 4:25530, 15 pages.

Bottley et al.; "Flow Cytometric Detection of Adenoviruses and Intracellular Adenovirus Proteins"; Adenovirus Methods and Protocols, 2nd Ed., vol. 1, Ch. 16; pp. 205-213; Methods in Modern Medicine, ed. W.S.M. Wold & A.E. Tollefson; Humana Press, 2007.

Brown, M. R. et al. Flow cytometric quantification of viruses in activated sludge. Water Research, 68, (2015), 414-422, available on-line Oct. 10, 2014.

Safety Data Sheet, "Buffer Solution pH 4" (2015) 4 pages, accessed at https://www.lewisu.edu/academics/biology/pdf/pH%20Buffer%204.pdf.

Ei-Hamalawi, A.R.A et al. The fluorometric determination of nucleic acids in pea seeds by use of ethidium bromide complexes. Analytical Biochemistry. (2015), 67(2), 384-391.

Vira et al. "Fluorescent labeled antibodies-balancing functionality and degree of labeling". Anal Biochem 402 (2): 146-150 (Jul. 15, 2010).

Brussard et al. "Flow cytometric detection of viruses". Journal of Virological Methods 85: 175-182 (2000).

Guo et al., "Multispectral labeling of antibodies with polyfluorophores on a DNA backbone and application in cellular imaging", PNAS vol. 108, No. 9: 3493-3498 (Mar. 1, 2011).

Luchowski et al., "Single Molecule Studies of Multiple-Fluorophore Labeled Antibodies. Effect of Homo-FRET on the Number of Photons Available Before Photobleaching", Curr Pharm Biotechnol. 9 (5): 411-420 (Oct. 2008).

Nadaud, et al., "Small platelet microparticle levels are increased in pulmonary arterial hypertension", European Journal of Clinical Investigation, vol. 43 (1), 2013, pp. 64-71 (8 pages).

* cited by examiner

FLOW CYTOMETRY EVALUATION OF BIOLOGICAL MATERIAL FOR UNASSOCIATED VIRUS-SIZE PARTICLES

REFERENCE TO RELATED APPLICATIONS

This application is a continuation of U.S. patent application Ser. No. 16/781,382 entitled "FLOW CYTOMETRY EVALUATION FOR VIRUS-SIZE PARTICLES WITH ANTIBODY STAIN HAVING LOW FLUOROPHORE RATIO" filed Feb. 4, 2020, which is a continuation of U.S. patent application Ser. No. 15/713,314 entitled "EVALUATING BIOLOGICAL MATERIAL FOR UNASSOCIATED VIRUS-LIKE PARTICLES" filed Sep. 22, 2017 (now U.S. Pat. No. 10,585,030), which is a continuation of U.S. patent application Ser. No. 15/558,107 entitled "FLOW CYTOMETRY METHOD FOR EVALUATING BIOLOGICAL MATERIAL FOR UNASSOCIATED VIRUS-SIZE PARTICLES OF INFLUENZA VIRUS VIRAL TYPE" filed Sep. 13, 2017 (now U.S. Pat. No. 10,161,850), which is a U.S. national stage filing under the Patent Cooperation Treaty of international patent application no. PCT/US2016/023737 entitled "FLOW CYTOMETRY METHOD FOR EVALUATING BIOLOGICAL MATERIAL FOR UNASSOCIATED VIRUS-SIZE PARTICLES OF INFLUENZA VIRUS VIRAL TYPE" filed Mar. 23, 2016, which claims the benefit of and incorporates by reference each and every one of the following U.S. provisional patent applications: Ser. No. 62/280,079 entitled FLOW CYTOMETRY METHOD FOR EVALUATING BIOLOGICAL MATERIAL FOR UNASSOCIATED PARTICLES OF VIRUS SIZE filed Jan. 18, 2016; Ser. No. 62/280,029 entitled EVALUATING BIOLOGICAL MATERIAL FOR UNASSOCIATED VIRUS-SIZE PARTICLES OF BACULOVIRUS VIRAL TYPE filed Jan. 18, 2016; Ser. No. 62/280,042 entitled EVALUATING BIOLOGICAL MATERIAL FOR UNASSOCIATED VIRUS-SIZE PARTICLES OF ADENOVIRUS VIRAL TYPE filed Jan. 18, 2016; Ser. No. 62/280,048 entitled EVALUATING BIOLOGICAL MATERIAL FOR UNASSOCIATED VIRUS-SIZE PARTICLES OF ADENO-ASSOCIATED VIRUS VIRAL TYPE filed Jan. 18, 2016; Ser. No. 62/273,874 entitled FLOW CYTOMETRY METHOD FOR EVALUATING BIOLOGICAL MATERIAL FOR UNASSOCIATED PARTICLES OF VIRUS SIZE filed Dec. 31, 2015; and Ser. No. 62/137,102 entitled FLOW CYTOMETRY METHOD FOR EVALUATING BIOLOGICAL MATERIAL FOR UNASSOCIATED PARTICLES OF VIRUS SIZE filed Mar. 23, 2015. Each and every one of the foregoing identified patents and patent applications is incorporated herein by reference, for all purposes.

FIELD OF THE INVENTION

This disclosure relates to flow cytometry evaluation of biological material for unassociated virus-size particles and fluorescent stains useful for such flow cytometry evaluations.

BACKGROUND OF THE INVENTION

There are a number of situations where quick, reliable, accurate and cost effective quantification of free, unassociated viral particles (formally referred to as virions) would be desirable. By quantity or quantification it is meant counting and determining a concentration of individual virus particles.

Some important situations concern the area of influenza viruses. Influenza viruses are viruses within the family Orthomyxovirus and include three genera, type A, type B and type C influenza virus (also referred to as influenza A virus, influenza B virus and influenza C virus). The infectious disease influenza is caused in humans primarily by type A and type B influenza virus. Type A and type B influenza virus serotypes are susceptible to continual evolution through genetic drift, which requires the continual development of new vaccines. This need in heightened for Type A influenza virus, serotypes of which are also susceptible to occasional rapid transformation through genetic drift, which can create pandemic situations and urgent needs for research and expedited vaccine development. Significant research has also been directed to creating viral agents for use as more universal influenza vaccines relative to traditional vaccines, for example in the area of virus-like particles with enhanced vaccine immunogenicity. Quickly and accurately evaluating influenza virus and related viral agents, both in vaccine production operations and for research and monitoring purposes, is a significant challenge, due in part to such genetic drift and genetic shift.

Also, following notable setbacks during the previous decade, the gene therapy field is currently resurgent, both in the breadth and the depth of different applications being pursued using this approach. With this continued success, however, comes the realization of the challenges inherent with transitioning from early research and development to late-stage clinical trials and product launch. A primary issue is the consistent and compliant production of viral vectors at levels necessary to support commercialization. As the number of successful trials grows and the likelihood of multiple product approvals increases, the realization that current manufacturing technologies have not kept pace highlights this as an area in urgent need of innovation. One of the most problematic steps is in the quantification of viral vectors during growth, harvest, purification and release. Current methods such as quantitative PCR and absorbance readings at 260 nm and 280 nm are highly variable, resulting in over- or under-estimation of particles present at any given step. The ramifications for manufacturing are lost product, delays and cost overruns, which are serious, yet pale in comparison to the risks associated with administering too little (no therapeutic effect) or too much (adverse immune response) product to patients. Clearly, there is a critical requirement for a rapid, more precise means of quantifying viral particles used for vector-mediated gene therapy.

Some traditional approaches to virus quantification include viral plaque assay (plaque titer assay), transmission electron microscopy (TEM) and single radial immunodiffusion (SRID) assay. These traditional approaches tend to have one or more of the following limitations: time-consuming, expensive, highly technical, high variability in results and subjective. Some newer approaches that have been proposed generally for virus quantification include field flow fractionation and multi-angle light scattering (FFF-MALS), tunable resistive pulse sensing (TRPS) and nanoparticle tracking analysis (NTS). All of these newer approaches may in some instances have some advantages relative to traditional quantification methods, but also have limitations, including typically providing limited virus data.

Carefully controlled flow cytometry using a combination of protein and nucleic acid fluorescent stains has also been used for quantification of a variety of viruses. Flow cytometry is an analytical technique in which physical and/or chemical properties of particles are measured as they flow in a fluid sample through an investigation cuvette, commonly referred to as a flow cell. Although the fluid sample may be investigated by subjecting the fluid sample to a variety of stimuli, light is one common stimulus technique. Devices containing a flow cell, and associated fluid flow, light delivery and light detection components, are typically referred to as flow cytometers.

The Virus Counter® flow cytometers (ViroCyt, Inc.) have been used to detect the presence of free, unassociated virus particles (sometimes referred to as virions) of a variety of viruses through a combination of very low and precisely controlled sample flow rate through the flow cell and use of two fluorogenic fluorescent stains having different fluorescent emission signatures, with one stain having an affinity for labeling nucleic acid and the other having affinity for labeling proteins. The stains are non-specific as to virus type, but identification of simultaneous detection events for the two different fluorescent emissions of the two fluorescent stains may be indicative of passage of such an unassociated virus particle through the flow cell. Contrary to such techniques as field flow fractionation and multi-angle light scattering (FFF-MALS), tunable resistive pulse sensing (TRPS) and nanoparticle tracking analysis (NTS) that measure only the presence of particles, virions or other particles, the Virus Counter® flow cytometers provide more biologically relevant information given the nature of the dyes used for enumeration.

Non-specific protein and nucleic acid stains of the types as noted above are fluorogenic. The stain molecules have only a very weak fluorescent response in a free, unbound state, but the magnitude of fluorescent response increases significantly when the molecule orientation becomes fixed when bound to a particle. This increase in fluorescent response from the free, unbound state to the bound state may be an order of magnitude increase or more. This permits the strong fluorescent signals of the bound stain molecules to be identified over background fluorescence from unbound stain molecules, because of the relatively much weaker fluorescent response from the unbound stain molecules.

There are some situations, however when such flow cytometry techniques have limitations. For example, the technique is not optimal for evaluation of non-enveloped viruses, for example such as adenovirus or adeno-associated virus. The absence of readily accessible envelope proteins on such non-enveloped viruses can significantly limit the accuracy of the technique for virus quantification. As another example, in some systems (e.g., baculovirus protein expression systems), target virus particles (e.g., baculovirus particles) may be present in a fluid that includes a high concentration of serum protein, often from fetal bovine serum (FBS). This may be the case for example when using BacMam expression vector systems. Presence of these high serum protein concentrations significantly complicates differentiation of fluorescent signals from stained virus protein from a high level of background of fluorescent signals from stained serum protein, which may significantly detrimentally impact virus quantification accuracy.

With respect to influenza virus, it is common to produce influenza virus in chicken eggs. This is a primary technique for producing influenza virus in the vaccine industry and or research purposes. Flow cytometry discrimination of harvested influenza virus particles is significantly complicated by the presence of ancillary material from chicken eggs that is collected along with harvested influenza virus. Such ancillary material may include, for example, cell debris, chicken embryo debris, bacteria, protein aggregates, lipids, lipid assemblies, lipid-protein assemblies, lecithins, lipid-protein aggregates, liposomes, ribosomes, vesicles, protein-nucleic acid complexes or other materials. Many of these ancillary materials may include protein or nucleic acid components that bind with the respective stains, which can create higher background signal levels that may complicate differentiation of the targeted influenza particles from stained debris signals. It is possible to purify the harvested influenza virus samples to some degree to remove at least some of such interfering ancillary material, which can improve flow cytometry operation, but such purification processing can be time consuming and can add significant expense, especially if it is desired to purify harvested influenza virus samples to a very high degree in preparation for flow cytometry evaluation, and even with a significant degree of purification such interfering material may still be present. Some particularly difficult ancillary materials are xanthophylls, which when present at a significant concentration can detrimentally interfere with binding of nucleic acid stain to the influenza virus particles of interest, which can contribute to significant undercounting of influenza virus particles.

Given the importance of applications involving such virus and viral agents, and the potential toxicity of viral agents in general, fast, inexpensive and reliable quantification techniques would be desirable.

SUMMARY OF THE INVENTION

Flow cytometry as a useful technique for evaluating virus particles is relatively new. Most flow cytometry evaluations of biological material have involved detection and investigation of properties of particles that are of a size on the order of cells from multi-cellular organisms or larger. Such particles may be individual cells or microspheres (typically made of a material such as latex or polystyrene) functionalized with an affinity to bind smaller biological units of interest. Such microspheres are also sometimes referred to as beads or microbeads. The presence of cell or microsphere particles is typically identified during flow cytometry through detecting and analyzing scattered light exiting from the flow cell. Various fluorescent stain techniques have also been used to provide additional information about some specific biological properties of such particles, for example particular biological attributes of detected cells or of biological material bound to microspheres. Cell or microsphere particle detection through light scatter is supplemented by detecting also for the specific fluorescent emission from the fluorescent stain. Some fluorescent stains include a fluorescent molecule bound to an antibody with binding capability for a particular epitope of interest for evaluation. These stains, however, tend to be fluorophores, which exhibit a high level of fluorescent response whether or not bound to a particle. Effective quantification of a virus-size particles in a fluid sample by flow cytometry requires counting individual unassociated particles of a virus size, measuring sample flow and calculating the virus-size particle concentration from the measured particle count and measured sample flow. Unlike fluorogenic stains, the presence of background signals from unbound fluorophore stains is a significant concern. Some techniques may be utilized to ensure that a detected fluorescent signal is associated with the cell or microsphere of interest, rather than coming from stained debris or from free, unbound fluorescent stain molecules that may remain in solution. After staining the particles with the desired fluorescent stain, the particles may be separated from liquid that contains residual fluorescent stain molecules in solution, such as by filtration or by accelerated sedimentation, such as by centrifugation, and decantation.

The separated cells or microsphere particles may then be re-suspended in fresh suspension liquid that is free of unbound fluorescent stain. Also, a time correlation analysis may be performed to identify simultaneous occurrence of simultaneous events of light scatter detection indicative of presence of a cell or microsphere particle and fluorescent emission detection indicative of the presence of the fluorescent stain, which helps to ensure that a detected fluorescent signal is in fact associated with properties of biological material of the cells or microspheres.

It has been found, however, that flow cytometry quantification of virus particles may be performed using fluorescent antibody stain, and without particle identification by light scatter detection, without separating stained virus particles from liquid with residual unbound stain following virus-particle staining, and without requiring simultaneous detection of non-specific protein and nucleic acid stains. This facilitates practical use of fluorophore antibody stains for virus detection for virotherapy and other applications, and without complications of identifying particles of virus-size through light scatter detection or simultaneous detection of nucleic acid and protein fluorogenic stains and without removal of stained particles from residual unbound antibody stain fluorophores in the fluid sample following staining. This is remarkable given the very small size of such virus particles.

An aspect of this disclosure is a method for evaluating a biological material sample for unassociated virus-size particles having a particular epitope, i.e., particular antibody-binding capability. Particular antibody-binding activity may be indicative of particle type, for example the viral type of a virus or virus-like particle or the type of an exosome or other nanoparticle. The method includes subjecting to flow cytometry a fluid sample comprising at least a portion of a biological material sample to be evaluated, wherein the fluid sample comprises a fluorescent antibody stain capable of binding, directly or indirectly, with the particular epitope. The flow cytometry may include flowing the fluid sample through a flow cell of a flow cytometer; subjecting the fluid sample flowing through the flow cell to excitation radiation capable of causing a fluorescent emission response from the fluorescent antibody stain; and detecting radiation from the flow cell within a wavelength range of the fluorescent emission and evaluating the detected radiation to identify detection events indicative of passage through the flow cell of unassociated labeled particles of virus size including a said virus-size particle having the epitope and the fluorescent antibody stain. Each such detection event corresponds with a single such unassociated labeled particle.

A number of feature refinements and additional features are applicable to this and other aspects of this disclosure. These feature refinements and additional features may be used individually or in any combination within the subject matter of this aspect or any other aspect of this disclosure. As such, each of the following features may, but are not required to be, used with any other feature or a combination of features of this aspect or any other aspect of this disclosure.

A primary area of application for the method of this aspect is in the area of influenza virus, including in situations when a sample to be evaluated includes interfering ancillary material from chicken eggs (including any such ancillary material as discussed above), such as is common in the vaccine industry. The vaccine industry is constantly developing and manufacturing new vaccine products to address the rapid evolution and emergence of influenza virus strains, and has a significant need for fast, inexpensive and reliable techniques for quantifying the presence of virus-size particles of an influenza virus viral type. This need extends for example to quantifying influenza virus particles and other viral particles, such as virus-like particles of an influenza virus viral type. Variations of the method of this aspect are, however, also applicable to other virus and viral agent applications, including as further discussed below.

The method may include preparing a fluid sample that includes the biological material to be evaluated for presence of the unassociated particles of virus size and at least one fluorescent antibody stain that is capable of binding, directly or indirectly, with the unassociated virus-size particles through the epitope to form unassociated labeled particles of virus size that may be detected during flow cytometry. Preparing the fluid sample may include mixing the biological material or a portion thereof to be evaluated with the fluorescent antibody stain. Subjecting the fluid sample to flow cytometry may include flowing the fluid sample through a flow cell of a flow cytometer under flow conditions for passage of virus-size particles individually through the flow cell.

The unassociated particles of virus size targeted for detection may be any particles of virus size including an epitope of interest. Such particles may have multiple epitopes, at least one of which is of interest for particle evaluation. Multiple epitopes may be of interest on the same particle of virus size of interest, and may be targeted using a corresponding number of different fluorescent antibody stains. Examples of some unassociated particles of virus size that may be targeted for detection include viral particles (including viruses and particles such as virus-like particles with virus attributes) and exosomes. The discussion provided herein is exemplified primarily by reference to viral particles, but the principles discussed apply also to other particles of virus size (e.g., exosomes and other nanoparticles) having a particular epitope that may be targeted for detection.

A significant advantage of the method is that residual, unbound fluorescent antibody stain in solution need not be removed from the fluid sample prior to flow cytometry. Separation of remaining unbound fluorescent antibody stain from the fluorescently labeled particles of virus size of interest for evaluation would require cumbersome and time consuming processing, such as ultracentrifugation. This is significantly different than separating antibody stain from larger labeled particles such as cells or immunoassay beads in prior applications, and separating the fluorescent antibody stain from particles of virus size is significantly more complicated, time consuming and expensive than in such larger-particle contexts. In preferred implementations, preparing a fluid sample includes, after the mixing, not removing unbound fluorescent antibody stain, that is fluorescent antibody stain not bound in the unassociated labeled particles (e.g., free in solution), from the fluid sample prior to flow cytometry. In other words, residual unbound fluorescent antibody stain from the mixing may be retained in the fluid sample to remain in the fluid sample when the fluid sample is subjected to flow cytometry. Such unbound fluorescent antibody stain may represent most of the fluorescent antibody stain that is mixed with the biological material during the noted mixing step. However, an important consideration for flow cytometry performance is control of concentration of such residual, unbound fluorescent antibody stain molecules in solution so that fluorescent emission signals from such unbound fluorescent antibody stain molecules do not overwhelm or dominate over fluorescent emission signals from the unassociated labeled particles of virus size and prevent differentiation of the emission signals from the unassociated labeled particles. In some preferred implementations, the fluid sample as fed to the flow cytometer may have a concentration of such unbound fluorescent antibody stain, not bound in unassociated labeled particles, in a range having a lower limit of 0.25 microgram per milliliter, 0.5 microgram per milliliter, 0.7 microgram per milliliter, 1 microgram per milliliter, 2 micrograms per milliliter, 3 micrograms per milliliter or 5 micrograms per milliliter and an upper limit of 10 micrograms per milliliter, 8 micrograms per milliliter, 7 micrograms per milliliter, 6 micrograms per milliliter, 5 micrograms per milliliter, 4 micrograms per milliliter, 3 micrograms per milliliter, 2.5 micrograms per milliliter or 2 micrograms per milliliter, with the upper limit being larger than the lower limit. When a fluid sample includes multiple different types of fluorescent antibody stains, such a concentration of residual, unbound fluorescent antibody stain may be applied to a concentration of each separate fluorescent antibody stain type and/or to a combined concentration of some or all of the fluorescent antibody stains. Such a concentration of residual, unbound fluorescent antibody stain of about 2, about 2.5 or about 3 micrograms per milliliter or within a relatively narrow range (e.g., within 0.5 microgram per milliliter) above or below 2, 2.5 or 3 micrograms per milliliter may be preferred for many implementations. In some preferred implementations, the fluid sample as fed to the flow cytometer may have a total concentration of a fluorescent antibody stain, including residual, unbound fluorescent antibody stain and fluorescent antibody stain bound in unassociated labeled particles in a range having a lower limit of 0.25 microgram per milliliter, 0.5 microgram per milliliter, 0.7 microgram per milliliter, 1 microgram per milliliter, 2 micrograms per milliliter, 3 micrograms per milliliter or 5 micrograms per milliliter and an upper limit of 10 micrograms per milliliter, 8 micrograms per milliliter, 7 micrograms per milliliter, 6 micrograms per milliliter, 5 micrograms per milliliter or 4 micrograms per milliliter, 3 microgram per milliliter, 2.5 micrograms per milliliter or 2 micrograms per milliliter, with the upper limit being larger than the lower limit. Such a total concentration of fluorescent antibody stain of about 2, about 2.5 or about 3 micrograms per milliliter or within a relatively narrow range (e.g., within 0.5 micrograms per milliliter) above or below 2, 2.5 or 3 micrograms per milliliter may be preferred for many implementations. When a fluid sample includes multiple different types of fluorescent antibody stains, such a total concentration of fluorescent antibody stain may be applied to a total concentration of each separate fluorescent antibody type and/or to a total combined concentration for some or all of the fluorescent antibody stains. Such a concentration of about 2, about 2.5 or about 3 micrograms per milliliter or within a relatively narrow range (e.g., within 0.5 micrograms per milliliter) above or below 2, 2.5 or 3 micrograms per milliliter may be preferred for many implementations. As will be appreciated, an optimal concentration for such a total concentration of fluorescent antibody stain or for such a concentration of residual, unassociated antibody stain may vary somewhat between particular applications, but the specified ranges may be generally applicable across many applications. Optimal concentration for a particular application may depend upon such variables as concentration of the targeted unassociated particles of virus size, the amount of the epitope (number of binding sites for the fluorescent antibody stain) on such unassociated particles and affinity of the fluorescent antibody stain for binding with the epitope on the unassociated particles. In some preferred implementations, the fluid sample as fed to the flow cytometer may have a concentration of the unassociated labeled particles in a range having a lower limit of $1\times10^5$, $1\times10^6$ or $1\times10^7$ particles per milliliter and an upper limit of $1\times10^9$, $1\times10^8$ or $1\times10^7$ particles per milliliter, provided that the upper limit is larger than the lower limit. When a fluid sample includes multiple different types of particles having different epitopes to be detected with different types of fluorescent antibody stains, such a concentration of unassociated labeled particles may be applied to a concentration of the unassociated labeled particles of each particle type and/or to a combined concentration for some or all of the unassociated labeled particles of all of the particle types to be detected. In some preferred implementations, essentially all of the particles of a type to be detected are in unassociated labeled particles of virus size when the fluid sample is fed to the flow cytometer. In some preferred implementations, when detection events occur during the flow cytometry that are indicative of unassociated labeled particles of virus size during the flow cytometry there are a number of such detection events per minute that are in a range having a lower limit of 300, 1,000 or 10,000 of such detection events per minute and an upper limit of 325,000 or 100,000 of such detection events per minute. As will be appreciated, sample fluid may need to be run at a variety of different dilutions to obtain desired concentrations of unassociated labeled particles and fluorescent stains (associated and unassociated with unassociated labeled particles) and appropriate counts per minute of detection events.

Another advantage of the processing disclosed herein is that particles of virus size of specific type (e.g., as indicated by having particular antigen-binding capability) type may be identified using flow cytometry without detecting for light scatter to identify the presence of particles, as has been the case for example when identifying virus type in a host cell or attached to a microsphere. In preferred implementations, the flow cytometry does not include (is in the absence of) detecting light scatter, and may include only detecting for fluorescent emissions from fluorescent stains or only detecting for fluorescent emissions of one or more fluorescent antibody stains.

A fluorescent antibody stain may include a fluorescent component or components attached to an antibody molecule that is specific to binding to an epitope of a targeted particle viral type. Such fluorescent component(s) may be any component(s) with fluorescent activity to function as a fluorescent label as attached to the antibody molecules. The attachment of a fluorescent component to the antibody molecule may be direct or indirect. The attachment may be through a chemical bond or other adherence mechanism. Some examples of fluorescent components that may be included in the fluorescent antibody stain include fluorophores (fluorescent chemical compounds), fluorescent conductive nanocrystals (quantum dots), fluorescent polymers, fluorescent phycobilins, and recombinant fluorescent proteins. The description herein is exemplified primarily with reference to the use of fluorophores, but the description applies also to other fluorescent components that could be attached to the antibody molecule. In the case of a fluorophore, the fluorescent antibody stain may preferably include an average number of attached fluorophore groups (dye molecules) per antibody molecule of the fluorescent antibody stain (F/P ratio) in a range having a lower limit of 3, 4 or 5 and an upper limit of 10, 9, 8 or 7, with a range of 5 to 7 being preferred for many applications. The antibody molecules of a fluorescent antibody stain may be monoclonal or polyclonal. Monoclonal antibodies may be preferred for targeting detection of many viral types in many situations. However, because of the rapid evolution of some virus, a polyclonal antibody may be preferred for some applications targeted to evaluation for various virus serotypes. This may be the case for example for influenza virus (especially type A influenza virus) and other virus that may be prone to rapid evolution, such as may be prone to rapid genetic drift, genetic drift and reassortment, for example RNA viruses. The viral type targeted for evaluation may be associated with any type of virus. Some example viral types, other than influenza virus, include baculovirus, adenovirus, enterovirus, adeno-associated virus (AAV) or norovirus and their specific serotypes. Viral type refers to the particular category of viral attribute that is targeted for detection and discrimination, and which may be at a family, subfamily, specie or serotype level, or any identifiable subset of the foregoing. As some examples, a targeted viral type may include a single specific serotype or may include multiple serotypes that share a common antigenic attribute for interaction with a fluorescent antibody stain (e.g., multiple serotypes that include a common epitope binding with the same monoclonal fluorescent antibody stain). In applications involving the evaluation for the presence of two different targeted viral types in a fluid sample, the different viral types may represent for example different families, subfamilies, genera, species or serotypes. One such example may be evaluation for the presence of two different serotypes of influenza virus as the different viral types. Another such example may be evaluation for different species of virus as the two different viral types. Another such example may be evaluation for two different virus families, for example for baculovirus and for virus-like particles of a different family of virus (e.g., influenza virus, adenovirus, adeno-associated virus). As will be appreciated, a fluorescent antibody stain with polyclonal antibody will include a variety of different stained antibody molecules that each bind with a different epitope of a targeted viral type, for example with different epitopes on different serotypes (e.g., different types, subtypes and/or strains of influenza virus). One preferred example for use of a polyclonal antibody is evaluation for an influenza viral type that spans multiple serotypes (e.g., polyclonal antibody with antibody molecules binding with epitopes of both type A and type B influenza virus, or polyclonal antibody molecules binding with epitopes of different subtypes and strains of type A influenza virus and/or with different strains of type B influenza virus).

As will be appreciated, influenza virus includes three types, type A, B and C, which all have a virus particle size often in a range of about 80 nanometers to 120 nanometers. A target influenza virus viral type may include any one or more than one of these three types. Type A influenza virus includes many different serotypes, and is susceptible to genetic drift and occasional rapid genetic shift. Accordingly, when a targeted influenza virus viral type includes type A influenza virus, polyclonal fluorescent antibody stain is often beneficial. Likewise, when targeting analysis across type A and type B influenza virus serotypes, use of a polyclonal fluorescent antibody may often be beneficial. However, in situations when analysis is targeted to a specific type A serotype, or specifically to type B influenza virus, with a single specific targeted epitope, then use of a monoclonal fluorescent antibody stain may be preferred. Type C influenza virus may also be targeted for evaluation, for example for research purposes.

In some applications, virus-size particles of a baculovirus viral type may be targeted for evaluation, either as the sole targeted viral type or in applications involving targeting another viral type as well such as targeting evaluation also of virus-like particles of the other viral type.

Baculovirus are a family (baculoviridae) of rod-shaped viruses up to 300 nm long, and which are particularly useful to produce recombinant proteins. Baculovirus normally infect and replicate in insect cells, and recombinant protein expression in insect cell systems using a genetically modified Baculovirus expression vector is a well-known technique. Baculovirus can also be genetically modified to include mammalian promoters to drive recombinant protein expression in mammalian cells. Modified baculovirus systems including mammalian promoters that are useful for transfer of inserted genetic material by transduction to mammalian cells are often referred to as the "BacMam" system for Baculovirus gene transfer into Mammalian cells.

Baculovirus is also very useful in the production of virus-like particles, which may include a variety of viral proteins. Example viral types that may be expressed in such virus-like particles include influenza virus, adenovirus and adeno-associated virus. Depending upon the particular process or processing stage within a process, baculovirus may be a desirable product or an undesirable contaminant. In either case, accurate monitoring and quantification of baculovirus at various points in a production operation are important for process and product control. As noted above, the presence of fetal bovine serum (FBS) in some baculovirus protein expression systems (e.g., the BacMam system) may significantly complicate differentiation of fluorescent signals from stained protein in viral particles of interest from a high level of background fluorescent signals from stained serum protein when using the prior technique of using a combination of nonspecific, fluorogenic protein and nucleic acid stains.

The fluorescent antibody stain may bind with the viral particle directly or indirectly through an epitope. By directly binding through an epitope it is meant that a site on the antibody portion of the fluorescent antibody stain binds with the epitope. By indirectly binding through an epitope, it is meant that there is an intermediate binding unit between the epitope and the fluorescent antibody stain. For example, the intermediate binding unit may be a different antibody (different than the antibody of the fluorescent antibody stain) that binds directly with an epitope and the fluorescent antibody stain is bound to that antibody, thereby binding the fluorescent antibody stain in the unassociated labeled particle.

The fluorescent antibody stain may include a fluorescent component, for example a fluorophore, that is excited by any convenient excitation radiation and with an appropriate Stokes shift between the absorption spectrum of the excitation radiation and the emission spectrum of the fluorescent emission. The fluorophore may be provided by a fluorescent dye molecule linked, or conjugated, with another molecule in a form in which the dye is in a fixed, highly fluorescent state. A fluorescent dye may be conjugated directly with an antibody or may be conjugated with another component that is then attached to the antibody (e.g. biotinylated fluorescent antibody stain, discussed below).

The excitation radiation for a fluorescent antibody stain, or for other fluorescent stains that may also be used, may be in any suitable wavelength range or ranges for the fluorescent stain or stains being used. When multiple fluorescent stains are used, it is preferred that the emission spectra of the different fluorescent stains do not overlap or only minimally overlap so that individual detection is facilitated. Excitation radiation may often be in the visible or near-visible spectrum (e.g., ultraviolet through near infrared). Some example sources for excitation radiation include LED's and lasers providing a narrow light spectrum. A variety of small lasers are available for use as an excitation radiation source. Some example lasers are green light lasers, for example green He—Ne or Nd:YAG lasers. Other possible lasers to provide excitation radiation are discussed, for example, in: Methods in Molecular Biology, Vol. 263, Flow Cytometry Protocols, 2d. ed., Edited by Hawley, Teresa S. and Haley Robert G., Humana Press, 2004, Chapter 23 "Small Lasers in Flow Cytometry", by Telford, William G., pages 399-418; Methods in Cell Biology, Vol. 102, Recent Advances in Cytometry, Part A: Instrumentation, Methods, Edited by Darzynkiewicz, Zbigniew et al., Elsevier, 2011, Chapter 15 "Lasers in Flow Cytometry", by Telford, William G., pages 375-407; and Telford, William G. et al., Supercontinuum white light lasers for flow cytometry, Cytometry A. 2009 May, 75(5): 450-459. doi:10.1002/cyto.a.20687.

In some preferred implementations when two or more different fluorescent stains are utilized for a single fluid sample, for example to evaluate for different biological material components, which may be different viral types, the multiple fluorescent stains may preferably be excited by the same narrow-spectrum excitation radiation, although in other implementations multiple excitation radiation sources or a single source (e.g., tunable white light source) providing multiple excitation radiation spectra may be used provided that the fluorescent emission responses of the different fluorescent stains are distinguishable from such different excitation radiation spectra. Some example excitation radiation for many applications may be narrow spectra including one of the following wavelengths: 350 nanometers, 405 nanometers, 488 nanometers, 532 nanometers, 543 nanometers, 561 nanometers, and 635 nanometers. The fluorescent emission spectra may include any narrow spectra, typically in the visible and near-visible spectrum. It is often preferable that a fluorescent emission spectrum of a fluorescent stain, including a fluorescent antibody stain, has a significant Stokes shift in peak wavelength relative to the peak excitation spectrum wavelength for that fluorescent stain. The Stokes shift in wavelength may be at least 5 nanometers, at least 10 nanometers, at least 20 nanometers or more. Many fluorescent stains have a Stokes shift in a range of 10 to 50 nanometers, although some may have much larger Stokes shifts.

Some example antibodies for use in fluorescent antibody stains for some viral types are shown in Table 1.

TABLE 1

| VIRAL TYPE | ANTIBODY | EXAMPLE ANTIBODY SUPPLIERS |
| --- | --- | --- |
| Influenza A,B | M149 (Polyclonal) | Takara |
| Baculovirus | AcV1 (Monoclonal) | Novus Biologicals Abnova |
| Adenovirus | 8C4 (Monoclonal) | Life Technologies (Thermo Fisher Scientific) LifeSpan BioSciences |
| Adeno-Associated Virus | | |
| Serotype 1 (AAV-1) | ADK1a (Monoclonal) | |
| Serotype 2 (AAV-2) | A20 (Monoclonal) | PROGEN Biotechnik |
| Serotype 3 (AAV-3) | A20 (Monoclonal) | |
| Serotype 4 (AAV-4) | ADK4 (Monoclonal) | |
| Serotype 5 (AAV-5) | ADK5a or ADK5b (Both Monoclonal) | |
| Serotype 6 (AAV-6) | ADK6 (Monoclonal) | |
| Serotype 8 (AAV-8) | ADK8 or ADK8/9 (Both Monoclonal) | |
| Serotype 9 (AAV-9) | ADK9 or ADK8/9 (Both Monoclonal) | |

An antibody of a fluorescent antibody stain may be a pan-serotype antibody (binding with multiple serotypes). The polyclonal M149 product from Takara is an anti-human influenza A, B rabbit polyclonal antibody that is pan-serotype across various influenza virus serotypes, including Type B influenza virus and various serotypes of Type A influenza virus. Monoclonal antibody of fluorescent antibody stain may be serotype specific or may be pan-serotype to some degree. For example, ADK8/9 listed in Table 1 is pan-serotype for AAV-8 and AAV-9 serotypes. As another example, for adenovirus an antibody in a fluorescent antibody stain for example binds to a capsid protein that is present across multiple serotypes. This is the case, for example, for 8C4 listed in Table 1, which binds with hexon protein that is present across multiple adenovirus serotypes.

A wide variety of fluorophores may be used in the fluorescent antibody stains. A fluorophore may be attached directly to the antibody or through a linking group. Such a linking group may be a biotin-derived linking group on a biotinylated antibody through which a fluorophore conjugated streptavidin may be bound to the antibody. For convenience of reference, such fluorescent antibody stains having a fluorophore attached to a biotinylated antibody may be referred to herein as a biotinylated fluorescent antibody stain. Table 2 shows some example fluorescent dye products in the Alexa Fluor product line (Life Technologies, Thermo Fisher Scientific) that may be used in conjugated form as fluorophores and peak excitation (absorption) wavelength and emission wavelength for conjugates of the dye molecules. The Stokes shift of the conjugate is the difference between these wavelengths:

TABLE 2

| Alexa Fluor Dye Product | Absorption Wavelength Maximum (nm) | Emission Wavelength Maximum (nm) |
| --- | --- | --- |
| Alexa Fluor 350 | 346 | 442 |
| Alexa Fluor 405 | 402 | 421 |
| Alexa Fluor 430 | 434 | 539 |
| Alexa Fluor 488 | 495 | 519 |
| Alexa Fluor 514 | 518 | 540 |
| Alexa Fluor 532 | 531 | 554 |
| Alexa Fluor 546 | 556 | 573 |
| Alexa Fluor 555 | 555 | 565 |
| Alexa Fluor 568 | 578 | 603 |
| Alexa Fluor 594 | 590 | 617 |
| Alexa Fluor 610 | 612 | 628 |
| Alexa Fluor 633 | 632 | 647 |
| Alexa Fluor 635 | 633 | 647 |
| Alexa Fluor 647 | 650 | 668 |
| Alexa Fluor 660 | 663 | 690 |
| Alexa Fluor 680 | 679 | 702 |
| Alexa Fluor 700 | 702 | 723 |
| Alexa Fluor 750 | 749 | 775 |
| Alexa Fluor 790 | 782 | 805 |

Some example dyes for use as fluorophores in a conjugate form with a green laser excitation light source, useful with a variety of antibodies to make a fluorescent antibody stain, are shown in Table 3.

TABLE 3

| FLUOROPHORE | EXAMPLE FLUOROPHORE SUPPLIERS |
|---|---|
| Alexa Fluor 532 | Life Technologies |
| | Thermo Fisher Scientific |
| CF532 | Biotium |
| DyLight 521 | emp Biotech |

Any of the example dyes listed in Tables 2 and 3, or other dyes, may be used in a fluorescent antibody stain with any of the example antibodies listed in Table 1.

The fluid sample may include only a single fluorescent stain, which would be a fluorescent antibody stain. In alternative implementations, the fluid sample may include multiple fluorescent stains (i.e., two or more than two different fluorescent stains), at least one of which is a fluorescent antibody stain. When multiple fluorescent stains are used, two or more than two of the fluorescent stains may be fluorescent antibody stains and/or one or more than one may be a fluorescent stain other than a fluorescent antibody stain, for example a non-specific fluorogenic stain. One example of such a non-specific fluorogenic stain is a stain for labeling nucleic acid. By non-specific fluorescent stain it is meant a fluorescent stain that is not specific as to viral type. An example of one non-specific fluorogenic stain for nucleic acid that is excitable by a green laser light source is POPO-3 from Life Technologies (Thermo Fisher Scientific). When using multiple different fluorescent antibody stains, the different fluorescent antibody stains may be directed toward identifying different viral types of viral particles, in which case each of the different fluorescent antibody stains will be capable of binding with different viral particles of different viral types to form different unassociated labeled particles. The flow cytometry may include detecting radiation from the flow cell within different wavelength ranges of the different fluorescent antibody stains to identify detection events indicative of passage of the different unassociated labeled particle types through the flow cell, which are indicative of the presence of the different viral types.

The mixing of biological material for evaluation with the fluorescent antibody stain may be performed in a liquid medium, for example in a buffered aqueous liquid. During the mixing, the fluorescent antibody stain may be provided in a form in which the fluorophore is already attached to the antibody or the fluorescent antibody stain may form in situ during the mixing from precursor components provided to the mixing. The fluorescent antibody stain may form in solution from such precursors during the mixing and then attach to unassociated particles and/or may form on the unassociated particles to form unassociated labeled particles. For example, in the case of a biotinylated fluorescent antibody stain, the biotinylated antibody stain may be pre-prepared and provided to the mixing in the pre-prepared state, such as dispersed in a buffered solution, or precursors for the biotinylated antibody stain may be provided separately to the mixing and may first be contacted during the mixing to form the biotinylated antibody in situ. As one example, a pre-prepared biotinylated antibody and a pre-prepared fluorophore:streptavidin conjugate may be separately supplied to the mixing, for example in separate buffered solution formulations. The pre-prepared biotinylated antibody and pre-prepared fluorophore:streptavidin conjugate may then react to form the biotinylated fluorescent antibody stain. Such reaction may occur prior to binding of the antibody to an unassociated particle and/or such reaction may occur after a biotinylated fluorescent antibody has already become bound to an unassociated particle, in which case the biotinylated fluorescent antibody stain may form directly on the unassociated particle, thereby forming an unassociated labeled particle with the formation of the biotinylated fluorescent antibody stain. When providing such precursors separately to the mixing, the precursors may be added in appropriate proportions to provide a desired concentration of the resulting fluorescent antibody stain and preferably without a lot of residual, unassociated fluorophore:streptavidin conjugate that would add significant additional background fluorescence.

The virus-size particles targeted for detection may be viral particles. By viral particles it is meant individual particles of virus (e.g., virions) or virus-like particles and viral type refers to the particular type of virus or virus-like particles associated with that type of virus. As will be appreciated virus-like particles are particles that are similar to a virus, but that are not infectious because they are lacking in a complete virus make-up, such as viral genetic material. The virus-size particles targeted for detection may be exosomes or other nanoparticles that have an epitope for binding with an antibody.

By virus-size particle or particle of a virus size, it is meant a particle of a size on the order of individual, free virus particles, or virions, which are typically in a range of from tens of nanometers to hundreds of nanometers. In some implementations, virus-size particles may have a size in a range having a lower limit of 10 nanometers, 20 nanometers, 40 nanometers, 60 nanometers or 80 nanometers and an upper limit of 2 microns, 1 micron, 600 nanometers, 300 nanometers or 200 nanometers. In some implementations virus-size particles may have any one or more of length dimension, diameter dimension or maximum cross dimension within such a range. By a particle being unassociated, it is meant that the particle is not part of a larger particle structure that is larger than virus size, for example the unassociated particle is not within a host cell or bound to a microsphere or part of an agglomerate that is larger than virus size. An unassociated labeled particle will have a somewhat larger size that the unlabeled virus-size particle (e.g., an unlabeled virion, exosome or virus-like particle). Even with the bound fluorescent antibody stain, the unassociated labeled particles are of virus-size, and may often have a maximum cross dimension that is larger than the maximum cross-dimension of unlabeled virus-size particle that is in a range having a lower limit of 10 nanometers, 20 nanometers or 30 nanometers and an upper limit of 200 nanometers, 150 nanometers, 100 nanometers, 50 nanometers or 25 nanometers, with the upper limit being larger than the lower limit. For example, it is common for individual antibody molecules to be of a size on the order of about 5 to 10 nanometers may increase the maximum cross-dimension of the labeled particle by twice that amount, or by about 10 to 20 nanometers, relative to the unlabeled virus-size particles. As will be appreciated, indirectly bound antibody stain may increase the maximum cross dimension by a larger amount as a result of intermediate binding groups.

The biological material to be evaluated may be obtained from any source. Some example sources include manufacturing operations in which virus are cultured (e.g., vaccine production), genetically modified viral particles are produced (e.g., virus-like particles) such as for alternative forms of vaccines, in which genetically modified viruses are produced for expression of recombinant proteins, or for delivery of genetic material for virotherapy, or in which batches of purified virus-size particles are prepared to test exclusion limits in biological fluids manufacturing. The method may be performed in association with or as part of such a manufacturing operation. The biological material may be the result of prior processing of an initial biological material, which may be a crude material that has been purified or otherwise processed to prepare a more suitable sample for flow cytometry evaluation. The biological material may be provided for mixing with the fluorescent antibody stain in any convenient form, including in an aqueous buffered solution, for example a phosphate buffered solution, which may include one or more additives or other reagents useful for processing. Likewise, the fluorescent antibody stain may be provided in any convenient form, including in a buffered solution, for example a phosphate buffered solution or other buffered solution. The biological material may be provided in a purified form such as may result from purification processing. Such purification processing may be as disclosed in International Patent Publication WO2014/210370A1, the entire contents of which are incorporated herein by reference. The biological material may be provided for mixing with the fluorescent antibody stain in a Tris-HCl buffer solution as disclosed for use in flow cytometry in WO2014/210370A1, or a different buffered solution may be used. The flow cytometer may, for example, be a Virus Counter® 2100 flow cytometer or preferably a Virus Counter® 3100 flow cytometer (ViroCyt, Inc.). Such flow cytometers are specifically designed to operate at very low sample flow rates to evaluate fluid samples for the presence of virus-size particles. Other flow cytometers may also be used, although less preferred, that provide adequate focusing of virus-size particles in the center of a flow of fluid sample for investigation in the flow cell. Some examples of other flow cytometers equipped with a green light laser source for excitation radiation are Attune® NxT (Thermo Fisher Scientific), CyFlow® Space (Sysmex) and S1000EXi (Stradedigm). Some examples of other flow cytometers that may include an excitation radiation source other than a green light laser are ACSCalibur™ (Becton Dickinson), BD LSR-Fortessa™ (Becton Dickinson), BD FACSCanto™ (Becton Dickinson), FACSVerse (Becton Dickinson), Gallios™ (Beckman Coulter), CyAn™ ADP (Beckman Coulter), SE520EXi (Stratedigm) and SP6800 (SONY). As noted above, the biological material in the fluid sample may be in a purified form for enhanced flow cytometry evaluation, and which may be the result of purification of a crude sample of biological material according to processing disclosed in WO2014/210370A1.

Preparing a fluid sample may include, prior to the mixing of biological material for evaluation with the fluorescent antibody stain, purifying a crude sample of biological material to prepare the biological material for the fluid sample as subjected to the flow cytometry. The purifying may include filtering out particles of larger-size impurities of the crude sample. Such larger-size impurities may include particles larger than virus size. Such larger-size impurities may include for example, cell debris, bacteria, mycobacteria protein aggregates, lipids, lipid assemblies, lipid-protein assemblies, lecithins, lipid-protein aggregates, liposomes, ribosomes, vesicles, protein-nucleic acid complexes or other materials. The filtering may include filtration with a filter separation size, or filtration size, that is not larger than 2 microns, not larger than 1.5 microns, not larger than 1.3 microns, not larger than 1 micron, not larger than 0.9 micron, not larger than 0.8 micron or not larger than 0.75 micron. The separation size may often be at least 0.05 micron, at least 0.1 micron, at least 0.3 micron, at least 0.4 micron, at least 0.5 micron, at least 0.6 micron or at least 0.7 micron. The purifying may include chromatographic removal of at least a portion of smaller-size impurities that may be smaller than virus size. Such smaller-size impurities may include, for example proteins and/or nucleic acids, and material derived from viruses, such as fragments or debris from viruses. The chromatographic removal may include spin chromatography in a centrifuge. The spin chromatography may include centrifuging the sample to be purified, which may be in a buffer solution, in the presence of chromatographic media that captures smaller-size impurities. Supernatant including remaining biological material may be further processed, such as by the filtering, or provided directly to be mixed with a fluorescent antibody stain.

In other implementations, the fluid sample may include a sample of biological material in a crude form that that has not been purified or has not been purified to a significant degree. Even using such a crude sample of biological material, specificity of the fluorescent antibody stain peak signals of labeled virus-size particles may be distinguishable from background readings.

In some preferred implementations the flow cytometry may include flowing the fluid sample through the flow cytometer flow cell at a very low fluid sample flow rate. Such a sample fluid flow rate may be in a range of from 250 to 3000 nanoliters per minute. As noted above, flow cytometers with larger flow rates may also be used that are capable of focusing virus-size particles in the center of a flow of fluid sample for investigation in the flow cell. Such flow cytometers may, for example, have fluid sample flows of up to 1 milliliter per minute. In preferred implementations, the flow cytometry may include hydrodynamically focusing flow of the fluid sample with a sheath fluid and flowing the fluid sample and the sheath fluid through the flow cell. Moreover, in some more preferred implementations, the flow cytometry or a flow cytometer used for such flow cytometry (e.g., Virus Counter® 3100 flow cytometer) may employ evaluation of particle attributes from fluorescent emission signals as described in international patent application no. PCT/US2015/033907 (published as WO2015/187783) entitled FLOW CYTOMTER PEAK SIGNAL IDENTIFICATION EMPLOYING DYNAMIC THRESHOLDING, the entire contents of which is incorporated herein by reference. Such, evaluation uses a dynamic threshold determination for identifying peak signal threshold for particle counting, and which is particularly advantageous for use with the methods disclosed herein for quantitatively evaluating the labeled unassociated particles of virus size. The Virus Counter® 3100 flow cytometer has been found to have advantageous capabilities for differentiating fluorescent response signals from unassociated labeled particles of virus size from background signals of residual unbound fluorescent antibody stain, identifying fluorescent response detection events indicative of passage of an unassociated labeled particle of virus size through the flow cell of the flow cytometer, counting such unassociated labeled particles in the fluid sample based on such detection events, and calculating and displaying concentration of the unassociated labeled particles in the flow sample in real time relative to passage of the fluid sample through the flow cell. The Virus Counter® 3100 flow cytometer monitors, measures and carefully controls fluid sample flow rate to the flow cell, and unlike other flow cytometers uses integrated measured flow rate data over time to determine sample fluid volume passing through the flow cell for concentration calculation purposes. Additional information is provided in WO2010/132053, the contents of which are incorporated herein by reference.

In some implementations the flow cytometry may include counting the detection events as occurrences of individual ones of the unassociated labeled particles passing through the flow cell to determine a count for unassociated labeled particles in a volume of the fluid sample passing through the flow cell; determining the volume of fluid sample passing through the flow cell that corresponds with the count; and determining a concentration of the unassociated labeled particles in the volume of the fluid sample passing through the flow cell using the count of unassociated labeled particles. Such counting may be performed in real time relative to the detecting of the radiation corresponding with the detection event, and determining of the concentration may also be performed in real time relative to passage of the volume of the fluid sample through the flow cell. Determining the volume of fluid sample passing through the flow cell may include measuring in real time with a flow sensor the flow rate of the fluid sample to the flow cell and integrating resulting measured flow rate data over time. Identification of detection events indicative of passage through the flow cell of the unassociated labeled particles may be determined in the absence of correlating with light scatter detection information. Flow cytometry operation control and data acquisition and analysis (e.g., identifying detection events, counting, determining volume, determining concentration, measuring flow rate data, integrating measured flow rate data) may be performed by an electronic controller, for example using a Virus Counter® 3100 flow cytometer.

The fluid sample may include multiple fluorescent stains (two or more fluorescent stains), at least one of which is a fluorescent antibody stain. In some implementations a fluorescent stain may be a first fluorescent stain having a first fluorescent emission and the fluid sample may include a different second fluorescent stain (and possibly also a different third or even more different fluorescent stains) that has a different second fluorescent emission. The first and second fluorescent emissions may be separately detected. First detection events for the first fluorescent emission may be indicative of a first particle property (e.g., presence of an epitope) and second detection events for the second fluorescent emission may be indicative of a second particle property (e.g., presence of a different epitope or some other property). The different properties of the first and second detection events may be in relation to both properties being present on a single virus-size particle (in which case first and second detection events will temporally coincide with the passage of a single particle through the flow cell) or may be in relation to each of the properties being present on different particles (in which case the first and second detection events will not temporally coincide). Such first and second fluorescent stains may or may not be excited by the same wavelengths of excitation radiation, although for simplicity of operation it is convenient to have both fluorescent stains excited by the same narrow spectra of excitation radiation.

In some implementations, a first fluorescent stain may be a fluorescent antibody stain and the second fluorescent stain may be a stain for nucleic acid, which may be a non-specific fluorogenic stain. Detection events for the second fluorescent emission may be indicative of passage of particles of virus size containing nucleic acid stained with the fluorescent nucleic acid stain. Results of the separate detecting of the first and second fluorescent stains may be compared for identification of occurrences of a said first detection event that temporally coincides with a said second detection event, which may be a further indication of passage through the flow cell of an unassociated labeled particle including both the epitope and the nucleic acid properties, for example which may be indicative of an in-tact virus particle. The comparison of the first and second detection events alternatively or additionally may include identification of occurrences of a first detection event that does not temporally coincide with a second detection event, which may for example be indicative of a virus-like particle or an exosome (or other nanoparticle) having the epitope property but not the nucleic acid property, because of the absence of genetic material. The comparison of the first and second detection events may alternatively or additionally include identification of occurrences of a second detection event that does not temporally coincide with a first detection event, for example which may be indicative of an exosome (or other nanoparticle) including the nucleic acid property but not the epitope property.

When using multiple fluorescent stains, there may be multiple fluorescent antibody stains. For example a first fluorescent antibody stain with a first fluorescent emission may be capable of binding with a first epitope and a different second fluorescent antibody stain with a second fluorescent emission may be capable of finding with a different second epitope. A third or more additional fluorescent antibody stains and/or one or more non-specific stains (e.g., non-specific nucleic acid stain) may also be used, although the flow cytometer used will need to be provided with capability to discriminate all of the different fluorescent emission spectra. The first and second fluorescent emissions may each be separately detected. The first detection events of radiation of the first florescent emission may be indicative of passage of unassociated labeled particles of virus size including particles of virus size including the first epitope and second detection events of radiation of the second fluorescent emission may be indicative of passage of unassociated labeled particles of virus size including particles of virus size including the second epitope. In the case when a virus-size particle has both the first and second epitopes, first and second detection events will temporally coincide, whereas when there are two different kinds of virus-size particles with one kind having the first epitope and the other kind having the second epitope, the first and second detection events will not temporally coincide. For example, a first epitope may be indicative of particles of a first viral type and the second epitope may be indicative of particles of a different second viral type. Alternatively, the first and second epitopes may both be indicative of the same viral type, for example when a viral particle includes both the first and second epitopes. In a case when the first and second epitopes may both be indicative of the same viral type, the viral type may for example be any of such example viral types.

In order to obtain even more specificity in relation to contents of a biological material sample under evaluation, different portions of the sample may be separately evaluated by flow cytometry with different fluorescent antibody stains used in each of the different fluid samples subjected to the different flow cytometry evaluations. In this way, a plurality of portions of a biological material sample may be processed to make a matrix of different fluid samples for flow cytometry with different combinations of fluorescent stains to test for different combinations of particle properties in the biological material sample. Each of the different fluid samples may, for example include different combinations of fluorescent antibody stain with a non-specific fluorogenic stain (e.g., nucleic acid stain) and/or with multiple fluorescent antibody stains. Such matrix-type evaluation may, for example, be used to prepare and test by flow cytometry one or more than one differently labeled fluid samples to evaluate for presence of a desired virus-size product particle and/or to evaluate for presence of undesired contaminant particles of virus size.

The method of evaluation including flow cytometry may be part of, or may be performed in connection with, a method for manufacturing a product comprising virus-size particles. Such manufacturing may include: generating the virus-size particles in a biological production operation; harvesting from the biological production operation crude product comprising the virus-size particles; and purifying at least a portion of material of the crude product to prepare a purified product including the virus-size particles. Such a purified product may be a final product or may be an intermediate product that may be subjected to further processing. Flow cytometry evaluation performed as part of or in connection with the manufacturing may include collecting a biological material sample from a stage of the production processing during which virus particles would be expected to be present in the biological material and evaluating the sample for presence of particles of virus size having a particular epitope, including subjecting at least a portion of the sample to flow cytometry. Such evaluation including flow cytometry may for example include any of the features or any combination of the features noted above. Such manufacturing may include performing the collecting multiple times to collect different said biological material samples to be evaluated from multiple different stages of the manufacturing and performing an evaluation including flow cytometry on each such collected biological material sample to be evaluated. In this way, product yield and quality may be verified through the various stages of manufacture processing and processing problems may be quickly identified, analyzed and corrective action taken. For example, the collecting may be performed at a first stage during the generating or harvesting and at a second stage during or after the purifying.

The method of evaluation including flow cytometry may be performed in an environment that is not a part of or in connection with such manufacturing. For example, the method may be performed in connection with research or diagnostic activities.

One application for the method disclosed herein is evaluating a biological material sample for virus-like particles when the biological material sample is suspected of including virus-like particles. This may be the case for example during or in connection with manufacture operations to make virus-like particles or products including virus-like particles, for example for use in vaccines or as a carrier (vector).

Another important application for the method disclosed herein is evaluating a biological material sample for influenza virus. This may be the case for example during or in connection with manufacture operations to make influenza virus for use to make vaccines.

Another important application for the method disclosed herein is evaluating a biological material sample for baculovirus particles. This may be the case for example during or in connection with manufacture operations using baculovirus to produce recombinant proteins or for generating virus-like particles.

Another important application for the method disclosed herein is evaluating a biological material for in-tact virus particles. Such virus detection may be to evaluate for virus contaminants and/or to evaluate for presence of desired virus products. In one variation, the virus may be a virus programmed for virotherapy. Such a virus may be for example, an anticancer oncolytic virus, a viral vector for gene therapy or immunotherapy.

Another important application for the method disclosed herein is evaluating a biological material sample for exosomes or other nanoparticles. Detection of such exosomes or other nanoparticles, may be for example help to identify contamination by an exosome or other nanoparticle or presence of desired exosome or other nanoparticle product. Exosomes have been a source of false positive indications in virus particle flow cytometry using fluorogenic protein and nucleic acid dye combinations, because such exosomes sometimes include both proteins and nucleic acid that can be stained and misidentified as a virus particle. Also, exosomes or other nanoparticles may independently be an object of investigation.

Another aspect of this disclosure is a composition in the form of a fluid formulation, such as for a fluid sample in preparation for flow cytometry evaluation. The fluid formulation comprises:

an aqueous liquid medium;
unassociated labeled particles of virus size in the aqueous liquid medium at a concentration of from $1 \times 10^5$ to $15 \times 10^9$ of the unassociated labeled particles per milliliter, wherein the unassociated labeled particles each includes a virus-size particle having a particular epitope and a fluorescent antibody stain specific for binding, directly or indirectly with the epitope; and
a concentration of the fluorescent antibody stain that is in an unassociated state in the aqueous liquid medium not bound in the unassociated labeled particles in a range of from 0.25 (or more) microgram per milliliter to 10 (or less) micrograms per milliliter.

A number of feature refinements and additional features are applicable to this and other aspects of this disclosure. These feature refinements and additional features may be used individually or in any combination within the subject matter of this aspect or any other aspect of this disclosure. As such, each of the following features may, but are not required to be, used with any other feature or a combination of features of this aspect or any other aspect of this disclosure.

Such a fluid formulation may be or have any feature or features described with respect to the fluid sample of the method aspect. Any of the aqueous liquid medium, unassociated labeled particles and concentration and components thereof, virus-size particle, epitope, fluorescent antibody stain and concentration of unassociated concentration of fluorescent antibody stain may be or have any feature or features described in relation to the fluid sample of the method aspect.

Other features of this and other aspects will be further understood with reference to the drawings and in view of the discussion provided below, to example implementations described below and to the claims.

DETAILED DESCRIPTION

Figure 1:
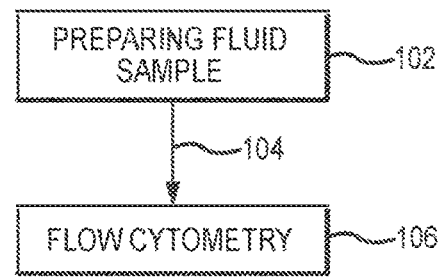
FIG. 1 shows a general process block diagram for some implementations of a flow cytometry method of the disclosure.
Figure 2:
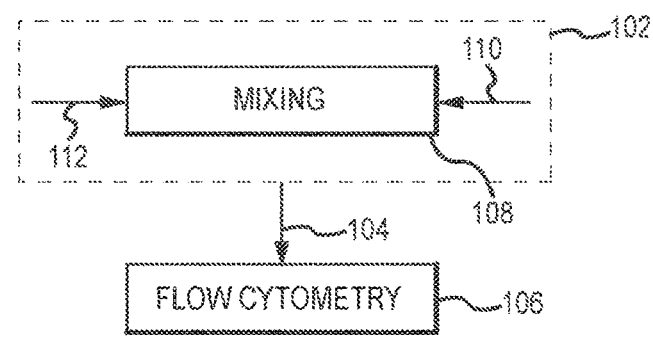
FIG. 2 shows a process block diagram illustrating some more specific processing implementations within the general processing of FIG. 1.

FIG. 1 shows a general process block diagram of processing for a flow cytometry method for evaluating biological material for the presence of unassociated viral particles of a particular targeted viral type. The processing shown in FIG. 1 includes a step of preparing a fluid sample 102 to prepare a fluid sample 104 that is then subjected to flow cytometry 106. The fluid sample 104 resulting from the preparing fluids sample 102 step includes a fluorescent antibody stain capable of binding, directly or indirectly, with the unassociated viral particles of the targeted viral type to form unassociated labeled particles that may be detected during the flow cytometry 106. The preparing fluid sample 102 may include mixing the biological material to be tested with at least one fluorescent antibody stain. FIG. 2 shows a process block diagram of a more specific example implementation of the general processing shown in FIG. 1, in which the preparing fluid sample 102 includes a mixing 108 step during which biological material 110 to be evaluated is mixed with a fluorescent antibody stain 112 that is capable of binding, directly or indirectly, with epitopes indicative of the targeted viral type for which the biological material 110 is being evaluated. As introduced to the mixing 108, the biological material 110 may be in a buffered solution at appropriate concentration for processing, and may be the result of prior processing from an initial crude sample of biological material. Such a solution in which the biological material 110 may be fed to the mixing 108 may also include other additives or reagents useful during the processing. Likewise, the fluorescent antibody stain may be provided to the mixing 108 step in an appropriately buffered solution with one or more additives or other reagents. For example, the fluorescent antibody stain 112 may be provided in buffer solution also including reagents to stabilize, help preserve or disperse the fluorescent antibody stain 112 prior to the mixing 108. For example, the fluorescent antibody stain 112 may be provided in a buffered solution containing an anti-agglomeration agent (e.g., bovine albumin) and/or an anti-microbial agent (e.g., sodium azide). The buffered-solution may be a phosphate buffered solution or other buffered solution at an appropriate PH.

Figure 3:
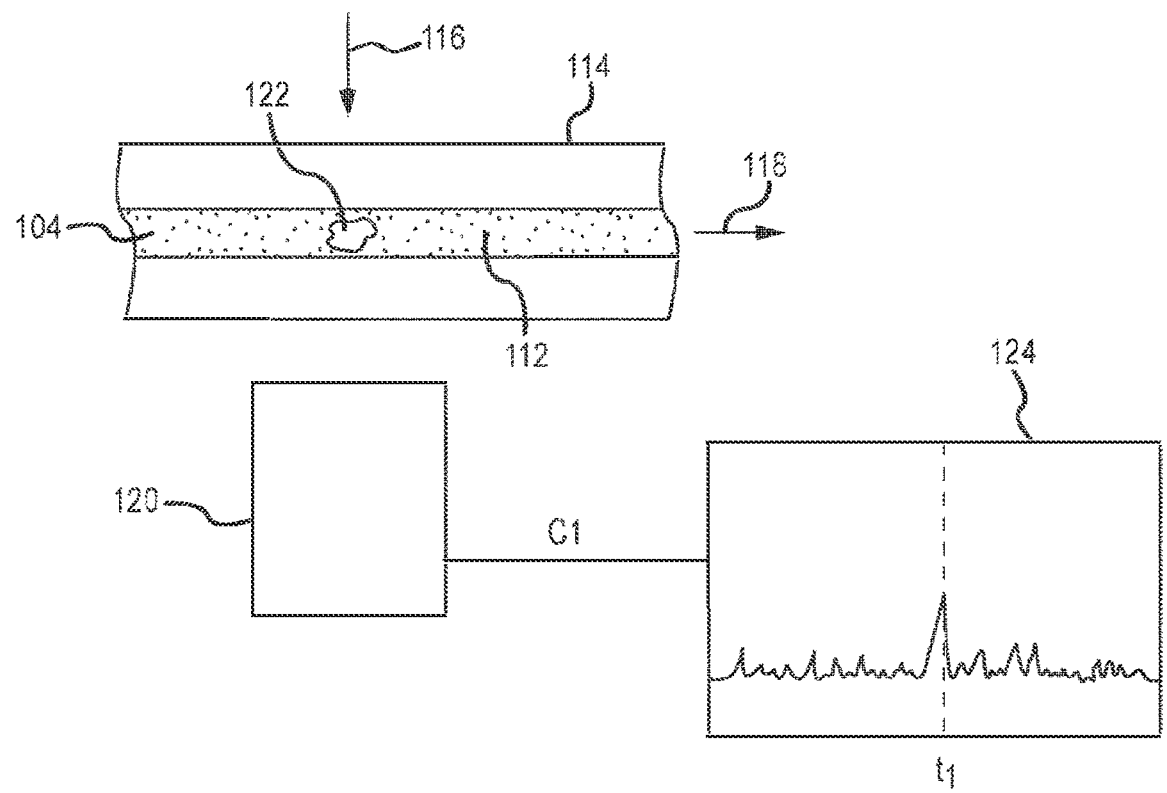
FIG. 3 illustrates an example of processing that may be performed during flow cytometry with the processing shown in FIG. 2.

FIG. 3 illustrates an example of processing that may be performed during the flow cytometry 106 of the example implementation of FIG. 2. As shown in FIG. 3, a flow of the fluid sample 104 through a flow cell 114 of a flow cytometer is subjected in the flow cell 114 to excitation radiation 116, for example from a laser, LED or other light source. In the example shown in FIG. 3, the flow of fluid sample 104 through the flow cell 114 is in the direction of the flow arrow 118. A detector system 120 includes optical componentry for detecting radiation coming from the flow cell within a wavelength range of the fluorescent emission of the fluorescent antibody stain 112. Illustrated in FIG. 3 is passage of an unassociated labeled particle 122 of virus size including a viral particle having fluorescent antibody stain bound thereto. FIG. 3 also illustrates an example time plot 124 of output (C1) of a photodetector detecting for the fluorescent emission and showing a peak voltage at time t1 corresponding with passage of such an unassociated labeled particle 122 through the flow cell 114. Also shown in FIG. 3 for illustration purposes are residual, unbound fluorescent antibody stain 112 in the fluid sample 104 that may contribute to some of the larger background peaks in the time plot 124.

Figure 4:
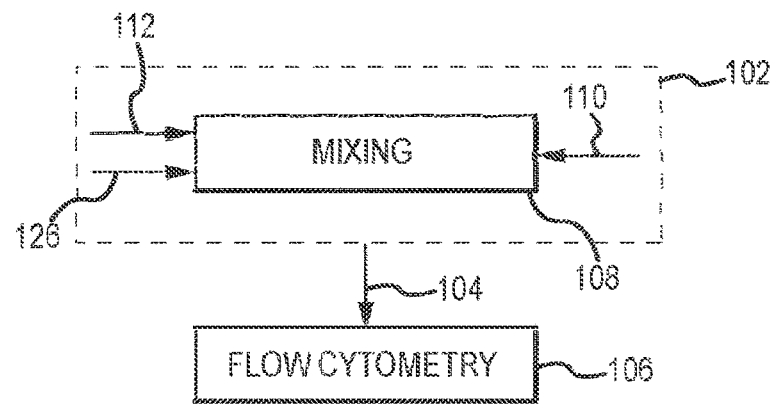
FIG. 4 shows a process block diagram illustrating some other more specific processing implementations within the general processing of FIG. 1.
Figure 5:
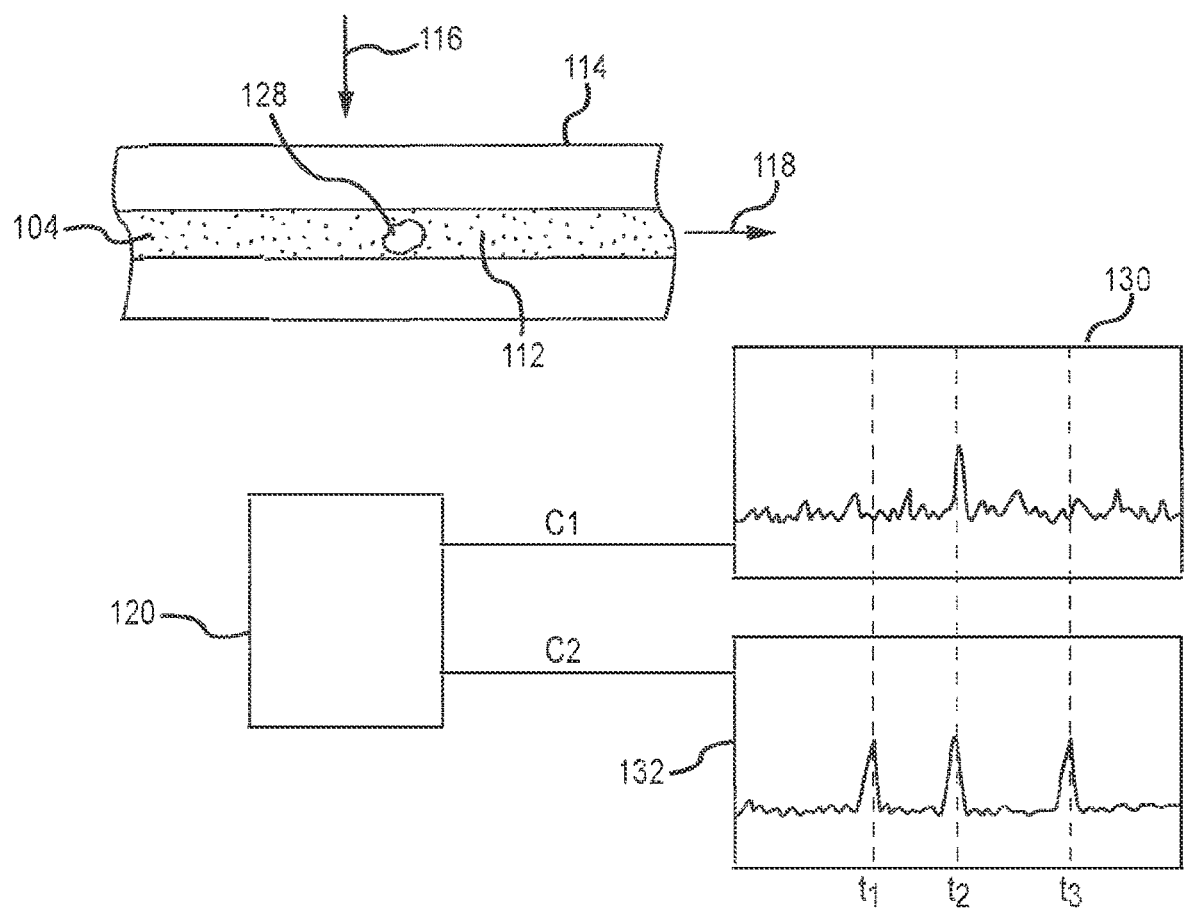
FIG. 5 illustrates an example of processing that may be performed during flow cytometry with the processing shown in FIG. 4.

The fluid sample 104 of FIG. 1 subjected to the flow cytometry 106 may be made using two or more different fluorescent stains, at least one of which is a fluorescent antibody stain. FIG. 4 shows example processing that is the same as that shown in FIG. 2, except that during the mixing 108 a second fluorescent stain 126 is provided to the mixing 108 step for inclusion in the fluid sample 104 that is subjected to the flow cytometry 106. In the example shown in FIG. 4, the second fluorescent stain 126 is a stain for nucleic acid that is not selective as to viral type. The second fluorescent stain 126 may be a fluorogenic stain and may be provided in a single formulation with the fluorescent antibody stain 112 or may be provided in a separate formulation. In a preferred processing situation, the fluorescent antibody stain 112 and the second fluorescent stain 126 may be provided in a single formulation, such as a single buffered solution in desired proportions for inclusion in the fluid sample 104. FIG. 5 illustrates an example of processing for the flow cytometry 106 of FIG. 4. As shown in FIG. 5, a flow of the fluid sample 104 through the flow cell 114 is subjected in the flow cell 114 to the excitation radiation 116. In the illustration shown in FIG. 5, the detection system 120 includes a first photodetector for detecting fluorescent emission from the fluorescent antibody stain 112 and a second photodetector for detecting a different fluorescent emission from the second fluorescent stain. FIG. 5 shows an example unassociated labeled particle 128 including a viral particle having attached thereto both the fluorescent antibody stain 112 and the second fluorescent stain 126. FIG. 5 shows a first time plot 130 with an example output (C1) of the first photodetector detecting for fluorescent emission from the fluorescent antibody stain 112 and a second time plot 132 showing example output (C2) from the second photodetector detecting for fluorescent emission from the second fluorescent stain 126. The time coincidence of voltage peaks at time t2 in the first time plot 130 and the second time plot 132 are indicative of passage of the unassociated labeled particle 128 through the flow cell 114. The voltage peaks at times t1 and t3 shown in the second time plot 132 are indicative of passage of particles through the flow cell 114 that contain the second fluorescent stain but that do not contain the fluorescent antibody stain 112. Such particles that may include the second fluorescent stain 126 and not the fluorescent antibody stain 112 may be, for example, viral particles of a different viral type than the viral type of the viral particle of the unassociated labeled particle 128. Greater magnitude of background and larger background peaks shown in the time plot 130 may be indicative of the passage of unbound fluorescent antibody stain 112 through the flow cell 114. For illustration purposes, FIG. 5 shows the presence of such unbound fluorescent antibody stain 112 in the fluid sample 104 passing through the flow cell 114. The second time plot 132 includes a background pattern with smaller background peaks indicative of the second fluorescent stain being a fluorogenic material that provides very little background fluorescent emission when not attached to nucleic acid with a particle.

Figure 6:
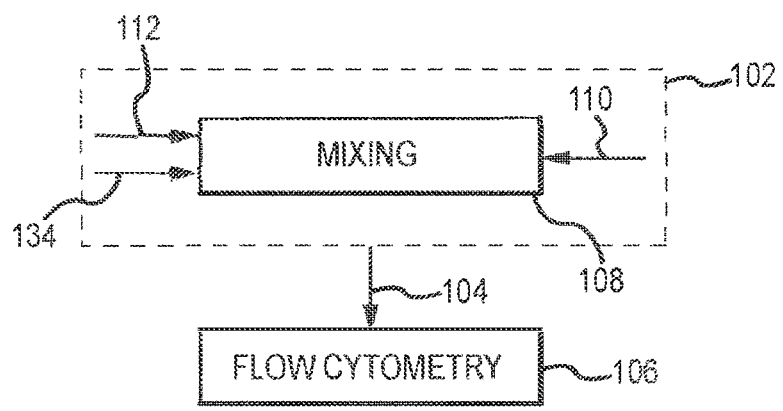
FIG. 6 shows a process block diagram illustrating some other more specific processing implementations within the general processing of FIG. 1.
Figure 7:
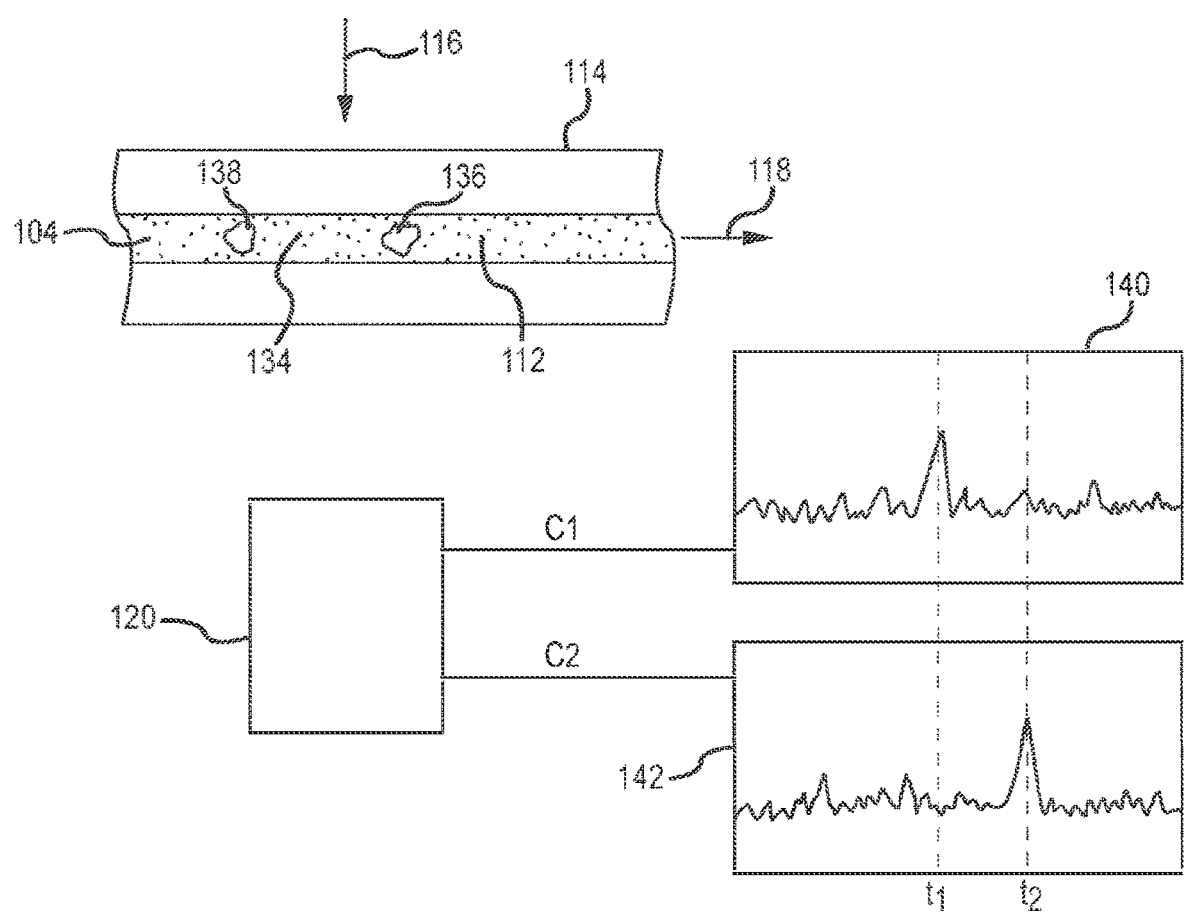
FIG. 7 illustrates an example of processing that may be performed during flow cytometry with the processing shown in FIG. 6.

FIG. 6 shows example processing that is the same as that shown in FIG. 4, except that the second fluorescent stain provided to the mixing 108 is a second fluorescent antibody stain 134 that is specific for binding to epitopes of viral particles of a different viral type (e.g., different virus or of a different serotype of the same virus) than the fluorescent antibody stain 112. Processing such as that shown in FIG. 6 may be used to discriminate between the presences of viral particles of different viral types present in the biological material 110 and to quantify the presence of viral particles of each of the two different types in the fluid sample. FIG. 7 illustrates an example of processing that may occur during the flow cytometry 106 of the processing example shown in FIG. 6. FIG. 7 is the same as FIG. 5, except showing the fluid sample 104 including an example first type of unassociated labeled particle 136 including a viral particle of a first viral type with the fluorescent antibody stain 112 attached thereto and a second type of unassociated labeled particle 138 including a viral particle of a second viral type having the second antibody stain 134 attached thereto. FIG. 7 shows a first time plot 140 illustrating example output (C1) of a first photodetector detecting fluorescent emissions of the fluorescent antibody stain 112 and a second time plot 142 illustrating example output (C2) from a second photodetector detecting fluorescent emissions from the second antibody stain 134. For illustration purposes, the fluid sample 104 in FIG. 7 is shown including unassociated first fluorescent antibody stain 112 and unassociated second fluorescent antibody stain 134. As shown in FIG. 7, a voltage peak on the first time plot 140 at time t1 is indicative of passage of the first type of unassociated labeled particle 136 through the flow cell 114 and the voltage peak at t2 shown in the second time plot 142 is indicative of passage of the second type of unassociated labeled particle 138 through the flow cell 114.

Figure 8:
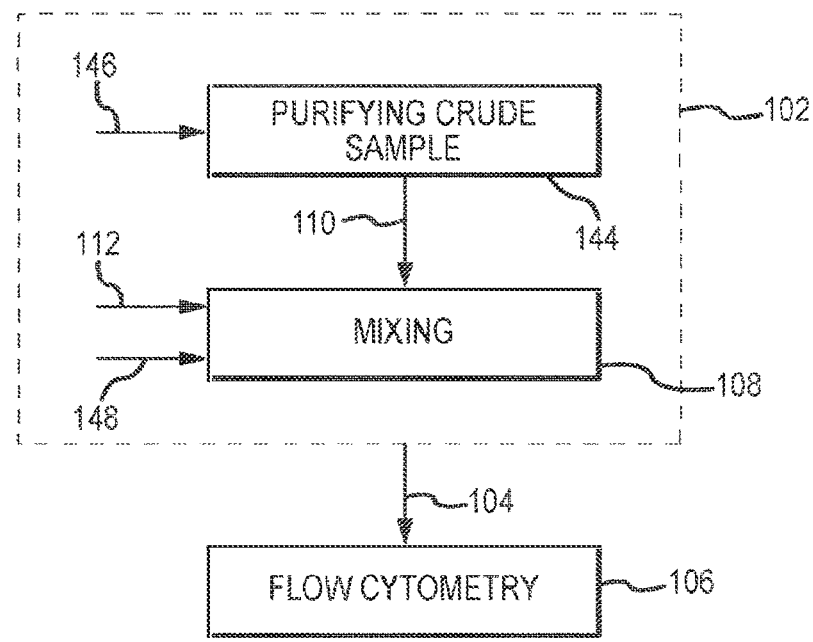
FIG. 8 shows a process block diagram illustrating some other more specific processing implementations within the general processing of FIG. 1.

FIG. 8 shows an example of processing according to the general processing shown in FIG. 1 in which the preparing a fluid sample 102 includes a purifying crude sample step 144 prior to the mixing 108. During the purifying crude sample 144, a crude sample of biological material 146 is subjected to purification processing to remove at least a portion of impurities that may interfere with the flow cytometry 106, to prepare the biological material 110 in a more pure form to be mixed with the fluorescent antibody stain 112 during the mixing 108 to prepare the fluid sample 104. For illustration purposes, the processing in FIG. 8 includes providing a second fluorescent stain 148 to the mixing 108 for inclusion in the fluid sample. The second fluorescent stain 148 may be a second fluorescent antibody stain that is different than the fluorescent antibody stain 112 or may be a non-specific fluorescent stain, for example a nucleic acid stain. The crude sample of biological material 146 may or may not be provided in a diluted form with buffer solution or other reagents and may or may not have been subjected to processing prior to introduction to the purifying crude sample 144 step.

Figure 9:
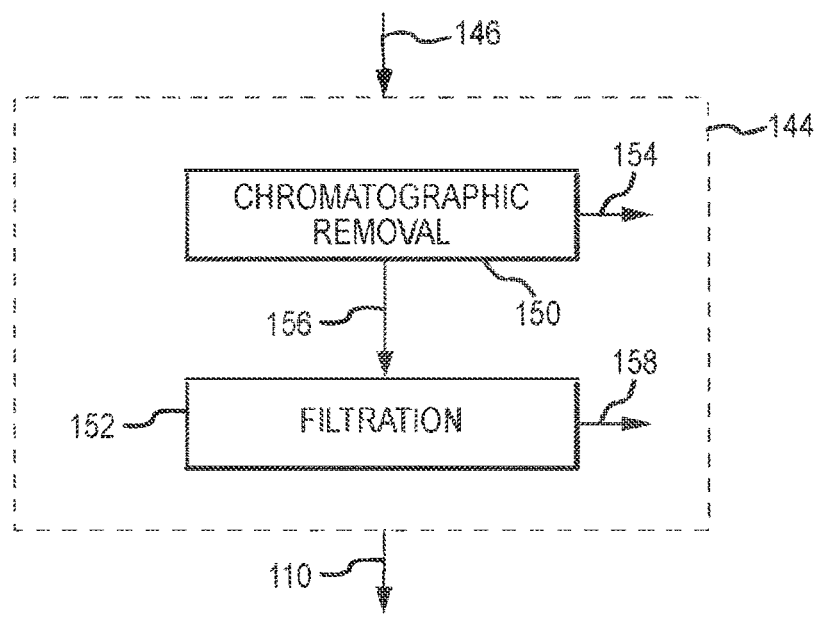
FIG. 9 shows a process block diagram illustrating some more specific processing implementations within a purifying crude sample step of the processing of FIG. 8.

FIG. 9 shows an example of processing that may be performed during the purifying crude sample 144 step of the general processing shown in FIG. 8. In the example processing shown in FIG. 9, the purifying crude sample 144 includes a chromatographic removal 150 step followed by a filtration 152 step. During the chromatographic removal 150, smaller-size impurities 154 are removed from the crude sample of biological material 146 by chromatography, with the smaller-size impurities 154 being retained within chromatographic media. The smaller-size impurities may be impurities smaller than a virus size. Processed liquid 156 from the chromatographic removal 150 is then subjected to the filtration 152 to filter out larger-size impurities 158. The larger-size impurities 158 may be removed as filter retentate and the biological material 110 provided to the mixing 108 may be or include filtrate from the filtration 152 or portions thereof, with or without further processing.

EXAMPLES

In the examples below, flow cytometry tests are performed on a Virus Counter® 3100 flow cytometer (ViroCyt, Inc.). Plots in the Figures referred to in these examples that plot virus particle concentration versus dilution factor are log-log plots. Flow cytometry tests using fluorescent antibody stain are performed without washing stained virus samples following staining and without detection of light scatter to assist with particle detection. Except as otherwise stated below, fluorescent antibody stains in these examples generally include an average number of attached dye molecules (fluorophores) per antibody molecule in the fluorescent antibody stain (F/P ratio) of 3 to 7. Concentrations of fluorescent antibody stains provided in these examples are total concentrations in the samples. As will be appreciated, some of this fluorescent antibody stain attaches to and stains virus particles in the samples, but most of fluorescent antibody stain in the samples will typically be in an unbound state when the samples are subjected to flow cytometry. All sample fluids in these examples are prepared to a pH within a range of pH 7 to pH8 with buffered solution.

Examples 1-6

In Examples 1-6 below the fluorescent antibody stain includes AcV1 monoclonal antibody that is specific for the gp64 envelope glycoprotein of baculovirus in a conjugate with a dye that is either Alexa Fluor 532 (identified below and in the figures as AFAcV1 antibody stain) or in a conjugate with CF532 (identified below as CFAcV1 antibody stain).

Example 1

Figure 10:
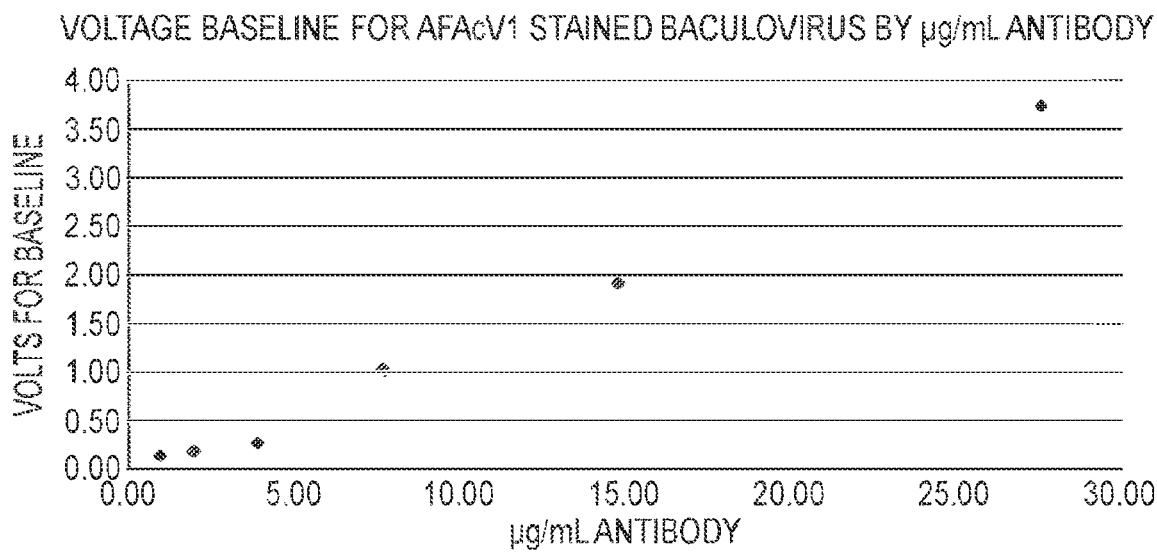
FIG. 10 is a plot summarizing some results for Example 1 presented below.
Figure 11:
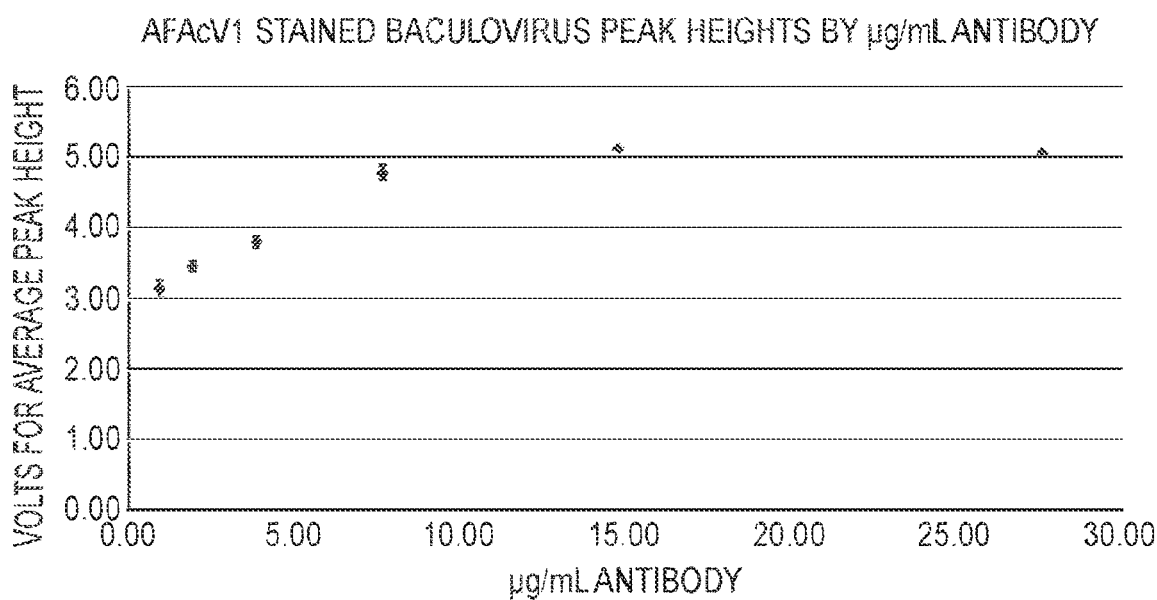
FIG. 11 is a plot summarizing some results for Example 1 presented below.
Figure 12:
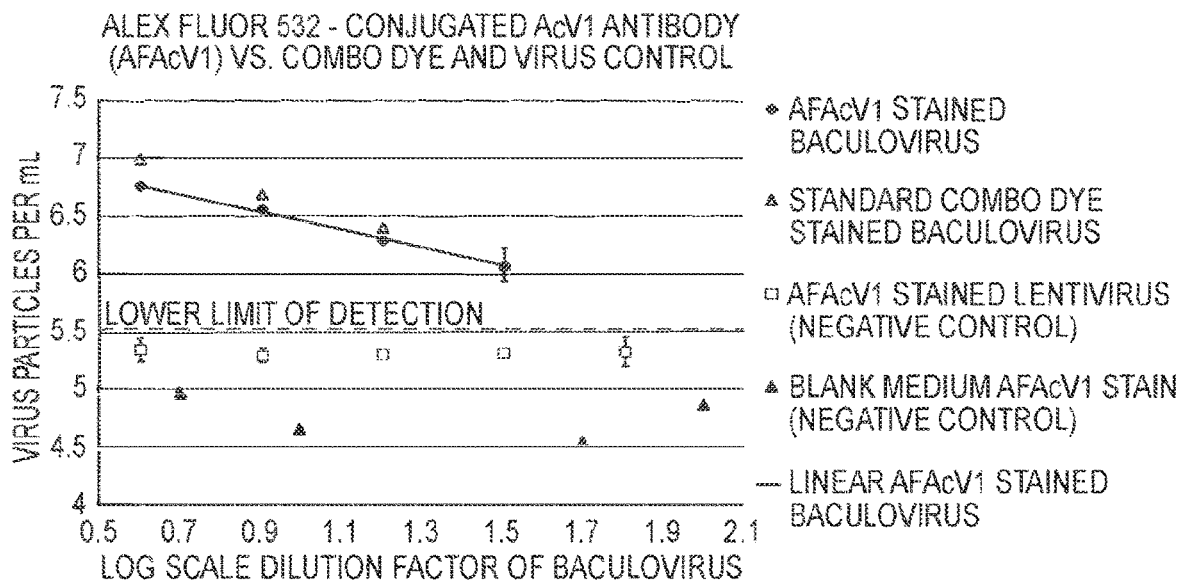
FIG. 12 is a plot summarizing results of for Example 2 presented below.

Test formulations including baculovirus and the baculovirus-specific fluorescent antibody stain AFAcV1 are prepared at a concentration of about 5×106 unassociated baculovirus particles per milliliter and with various concentrations of the fluorescent antibody stain. The different test formulations are subjected to flow cytometry. FIG. 10 summarizes measured baseline voltage response from a photodetector (photomultiplier tube) detecting for the fluorescent emission of the AFAcV1 stain (including the baseline component resulting from unbound AFAcV1 stain remaining in solution) as a function of AFAcV1 concentration in micrograms per milliliter. FIG. 11 summarizes identified average peak height voltages for specific fluorescent emission responses for detection events indicative of a baculovirus stained with the AFAcV1 stain as a function of the same AFAcV1 concentrations in micrograms per milliliter. The AFAcV1 concentrations shown are total concentrations in the test formulations, and as such include both AFAcV1 bound with the baculovirus and unbound AFAcV1, although a majority of the AFAcV1 in the test formulation will be in an unbound state even at the lowest total concentrations shown in FIG. 11.

As seen in FIG. 10, non-specific signal background in the test formulations increases with increasing concentrations of the AFAcV1 stain. As seen in FIG. 11, peak height of voltage signals from stained baculovirus increase at lower concentrations but level out as baculovirus particles become saturated with AFAcV1 stain bound to the particles. As seen in a comparison of FIGS. 10 and 11, there is a narrow range of the fluorescent antibody stain concentrations below about 8 micrograms per milliliter where the non-specific voltage baseline is low enough and the specific voltage peak heights of stained baculovirus are high enough for viable discrimination of baculovirus stained with the fluorescent antibody stain.

Example 2

Comparative flow cytometry tests are performed on baculovirus test formulations using the fluorescent antibody stain AFAcV1 relative to conventional virus staining with a combination of a non-specific protein stain and a non-specific nucleic acid stain (fluorogenic stains). Conventional staining tests are performed using the Combo Dye stain reagent (ViroCyt, Inc.), which is pre-formulated with appropriate proportions of non-specific protein stain and non-specific nucleic acid stain. Test solutions are subjected to flow cytometry evaluation. For Combo Dye runs, detection of a baculovirus particle is counted only when there are simultaneous separate detection events for fluorescent emissions from the nucleic acid stain and the protein stain. For the fluorescent antibody stain, detection of a baculovirus particle is counted based on detection events for fluorescent emissions from the AFAcV1 alone. For AFAcV1 tests, the total concentration of the AFAcV1 stain (both bound and unbound to baculovirus) in the test solutions is about 3 micrograms per milliliter. Four test solutions are prepared at different dilutions of stock baculovirus solution for each of the Combo Dye and fluorescent antibody stain tests, to provide four different baculovirus concentrations generally within a range of 106 to 107 virus particles per milliliter in buffered solution for each of the stain combinations. For a specificity control, the fluorescent antibody stain was tested against an unrelated virus, lentivirus, as well as buffered solution absent virus of any type.

Results are summarized in FIG. 12, which shows a plot of baculovirus concentration determined by flow cytometry as a function of dilution factor for the AFAcV1 stain tests at the Combo Dye tests. Both the vertical and horizontal axes are log-scale. As seen in FIG. 12, baculovirus concentrations indicated for the AFAcV1 tests are close to those indicated for the Combo Dye tests. FIG. 12 also summarizes data for the lentivirus and blank medium tests relative to an approximate lower detection limit for the flow cytometer of about log 5.5 particles per milliliter (about 1×105.5 particles per milliliter). The results demonstrate that data from the antibody stain-treated sample were analogous to the data generated using the Combo Dye. In addition, the antibody failed to bind to lentivirus, confirming the specificity of the fluorescent antibody stain. Furthermore, the antibody did not increase background to unacceptable levels when added to the blank medium.

Example 3

Flow cytometry dilution series using a variety of antibody stain concentrations are performed against a titration of baculovirus solution containing about 1×105 to 1×108 baculovirus particles per milliliter. Each dilution series includes flow cytometry of 200 microliter samples prepared at different dilutions of the stock baculovirus solution, with all samples in each dilution series containing the same concentration of the fluorescent antibody stain. Four dilution series are run at antibody stain concentrations of about 1.25, 2.5, 5 and 7.5 micrograms of CFAcV1 antibody stain per milliliter of sample. Flow cytometry tests are performed to detect and evaluate for fluorescent emissions from stained baculovirus. Results of the flow cytometry tests for each dilution series are summarized in FIGS. 13 and 14. FIG. 13 shows a plot of uncorrected baculovirus concentration (virus particles per milliliter) as determined for the samples by the flow cytometry tests, whereas FIG. 14 shows a plot of the same data but corrected the dilution factor. Both figures are log-log plots. FIGS. 13 and 14 both show good results (close to linear fit) at intermediate dilution factors, with the flow cytometry results corrected for dilution shown in FIG. 14 being close to the actual baculovirus concentrations of the baculovirus stock solution for the intermediate dilution factors. At lower dilution factors (higher baculovirus concentrations in the sample) and higher dilution factors (lower baculovirus concentrations in samples) results tend to degrade, which may indicate lower counts due to possible agglomeration of some baculovirus particles at the lower dilution factors and higher counts due to possible interference from background signals from unbound antibody stain at the higher dilution factors.

Example 4

Figure 13:
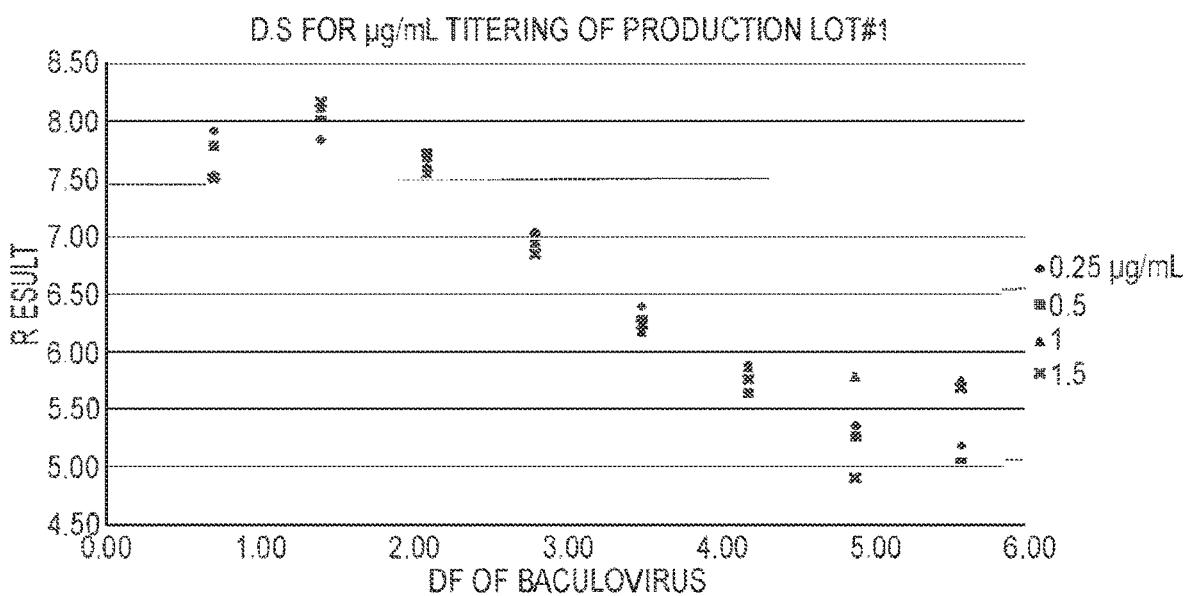
FIG. 13 is a plot summarizing some results for Example 3 presented below.
Figure 14:
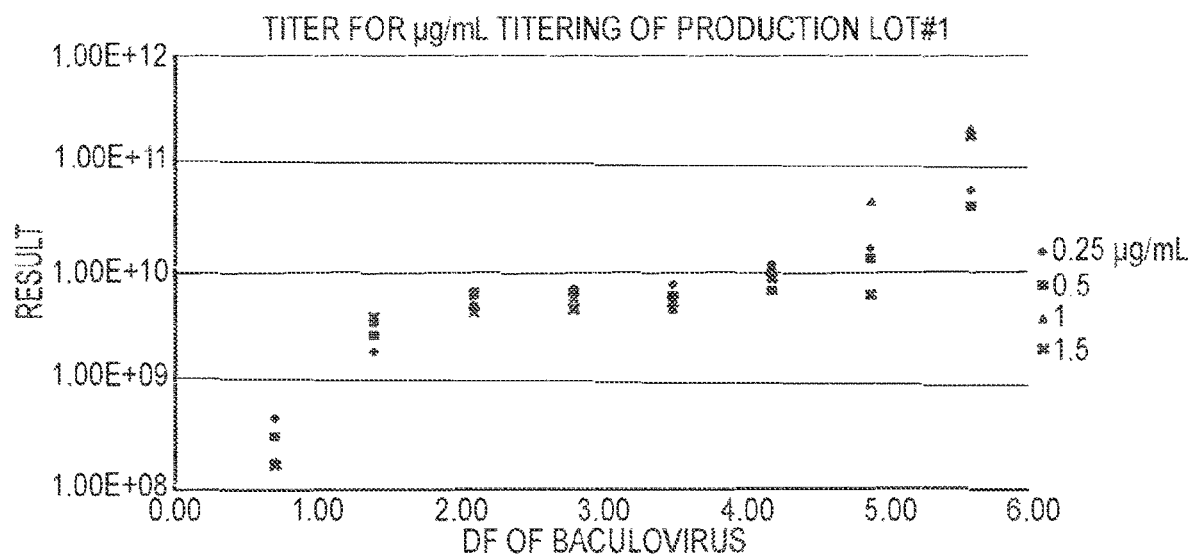
FIG. 14 is a plot summarizing some results for Example 3 presented below.
Figure 15:
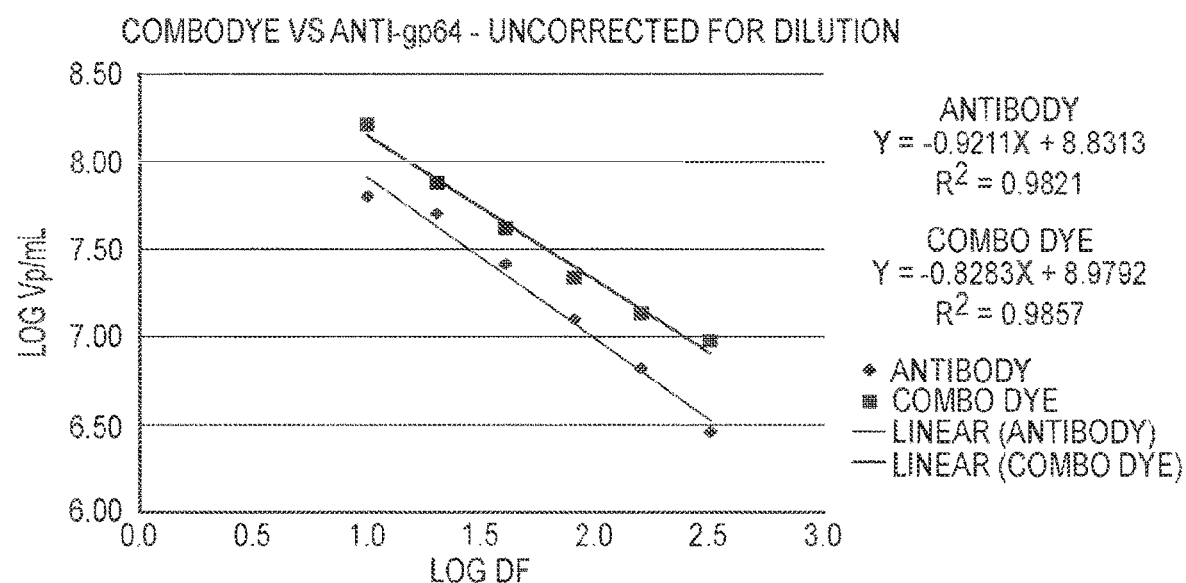
FIG. 15 is a plot summarizing some results for Example 4 presented below.
Figure 16:
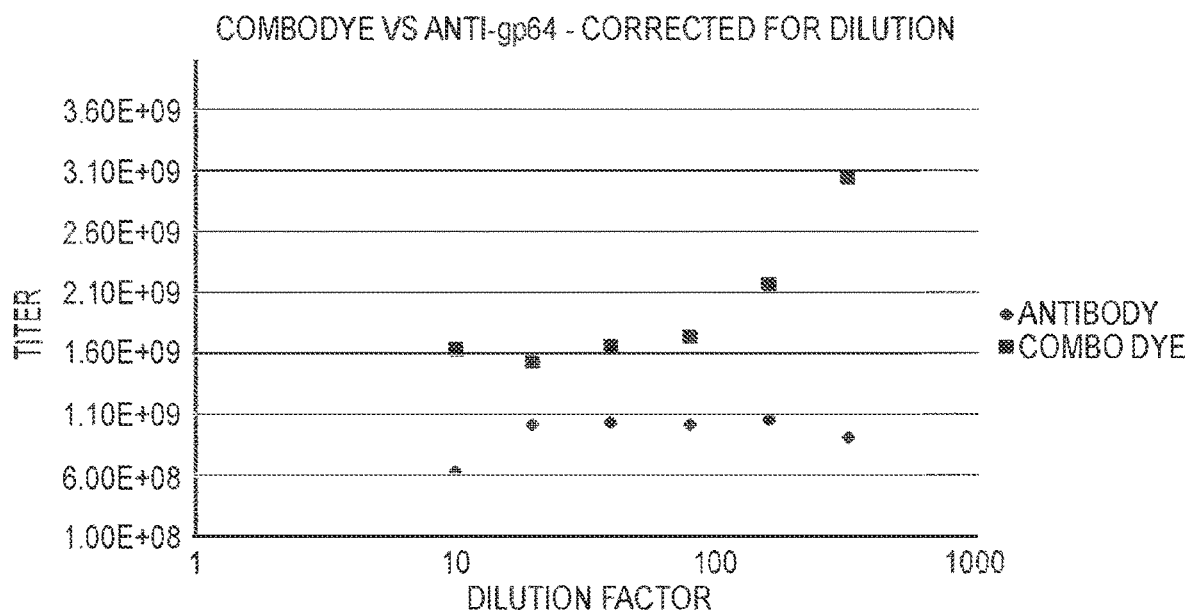
FIG. 16 is a plot summarizing some results for Example 4 presented below.

Comparative flow cytometry tests are performed using the fluorescent antibody stain CFAcV1 relative to Combo Dye (non-specific protein and nucleic acid fluorogenic stains), similar to Example 1. The concentration of fluorescent antibody stain in samples is about 2.5 micrograms per milliliter. Results are summarized graphically in FIGS. 15 and 16, with FIG. 15 plotting flow cytometry determined concentration of virus particles per milliliter versus dilution factor and FIG. 16 plotting the same data corrected by the dilution factor, similar to as described above for FIGS. 13 and 14. In this example, the virus concentration results generated using the fluorescent antibody stain are consistently lower than the virus concentration results generated using Combo Dye, and as shown in FIG. 16, the dilution-corrected virus concentration results determined using flow cytometry using the fluorescent antibody stain are closer to expectation based on the baculovirus concentration in the stock baculovirus solution.

Example 5

Figure 17:
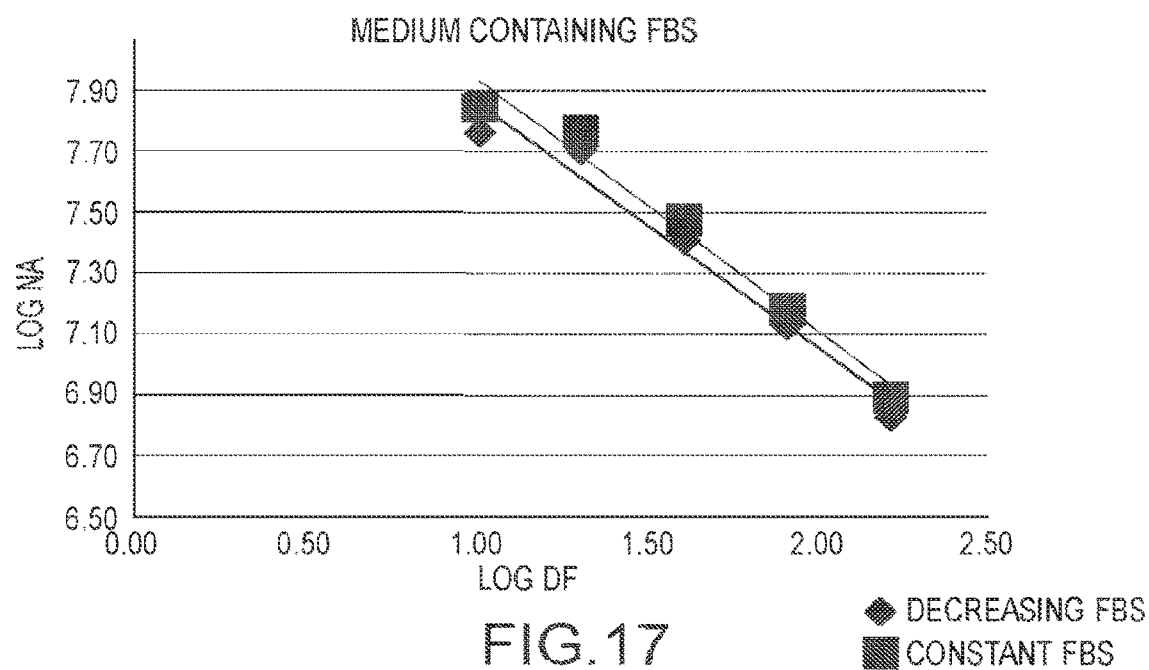
FIG. 17 is a plot summarizing results for Example 5 presented below.

Flow cytometry tests are performed to evaluate baculovirus detection using the fluorescent antibody stain FCAcV1 in the presence of fetal bovine serum (FBS). A titration of baculovirus is prepared containing from about 1×107 to 1×108 baculovirus particles per milliliter and about 3% by volume FBS (constant FBS) or diluted across approximately 2.5 logs (decreasing FBS). The flow cytometry dilution series are performed, with each sample containing about 2.5 micrograms per milliliter fluorescent antibody stain. In one dilution series, additional FBS is added to diluted samples, so that the concentration of FBS in all flow cytometry samples in the dilution series is about the same as in the stock solution (about 3% by volume FBS). In a second dilution series, no additional FBS is added and so the concentration of FBS is diluted along with baculovirus concentration. Results of the two dilution series are graphically summarized in FIG. 17. As shown in FIG. 17, the results of the two dilution series are very similar, indicating that presence of FBS in the samples was not detrimental to baculovirus identification using the fluorescent antibody stain.

Example 6

Figure 18:
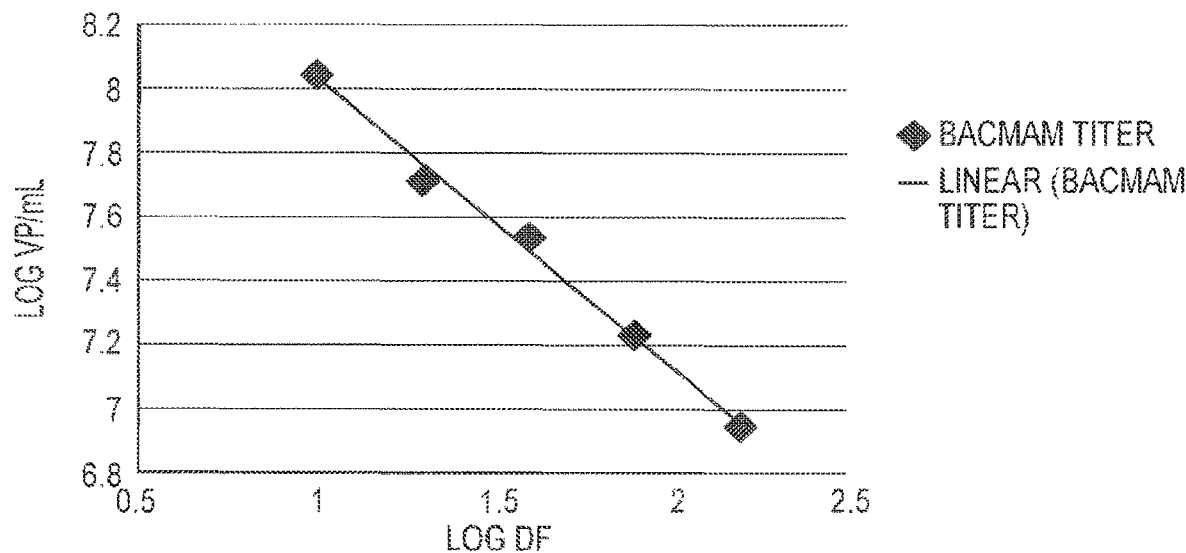
FIG. 18 is a plot summarizing results for Example 6 presented below.

A flow cytometry dilution series is run on a solution containing BacMam virus (modified baculovirus). A stock solution is prepared containing about 1×107 to 1×108 BacMam virus particles per milliliter and about 3% FBS. Flow cytometry samples are prepared with a concentration of the fluorescent antibody stain CFAcV1 of about 2.5 micrograms per milliliter. Results for the flow cytometry dilution series are graphically summarized in FIG. 18, which plots the concentration of BacMam virus per milliliter determined by flow cytometry at the different dilution factors, and demonstrating a good linear fit to the data.

Examples 7-8

Adenovirus are a family (adenoviridae) of non-enveloped virus about 90 to 100 nanometers in size with an icosahedral nucleocapsid containing a double stranded DNA genome ranging from 26 to 48 kbp in size. Adenovirus is infective of a number of vertebrate hosts, including many distinct serotypes that infect humans. Adenovirus is an important virus for use in a number of virotherapy applications, including for oncolytic, gene therapy and immunotherapy applications. Adenovirus is one of the primary vehicles for delivering genetic payloads to specific cell types, especially neoplastic cells. Adenovirus have high potential toxicity, and carful and accurate monitoring and quantification of adenovirus is important throughout various stages of manufacture and for accurate dosing in virotherapeutic formulations. For example, adenovirus is known to cause respiratory disease in humans, primarily in children, and it is essential that key viral genes are replaced with the required therapeutic gene or genes. To avoid this issue, as well as the likelihood of a host immune response to the vector, non-human strains of adenovirus are also being investigated. One of the most problematic aspects of producing adenovirus viral vectors is in the quantification of adenovirus viral vectors during growth, harvest, purification and release In Examples 7 and 8 below the fluorescent antibody stain is an 8C4 monoclonal antibody-CF 532 conjugate (identified below as CF-8C4). The 8C4 antibody is specific for the hexon protein of adenovirus, and is effective across different adenovirus serotypes (tested against at least serotypes 2 through 6).

Example 7

Comparative flow cytometry tests are performed on adenovirus test formulations using the fluorescent antibody stain CF-8C4 on two different test formulations containing different adenovirus serotypes. One test formulation included adenovirus serotype 4 and the other test formulation included adenovirus serotype 5. For all tests, the total concentration of the CF-8C4 antibody stain (both bound and unbound to adenovirus) in the test solutions is about 2.5 micrograms per milliliter. For each test formulation four test solutions are prepared at different dilutions of stock adenovirus solution for each for the dilution series, to provide four different virus concentrations for testing in buffered solution for each test formulation.

Figure 19:
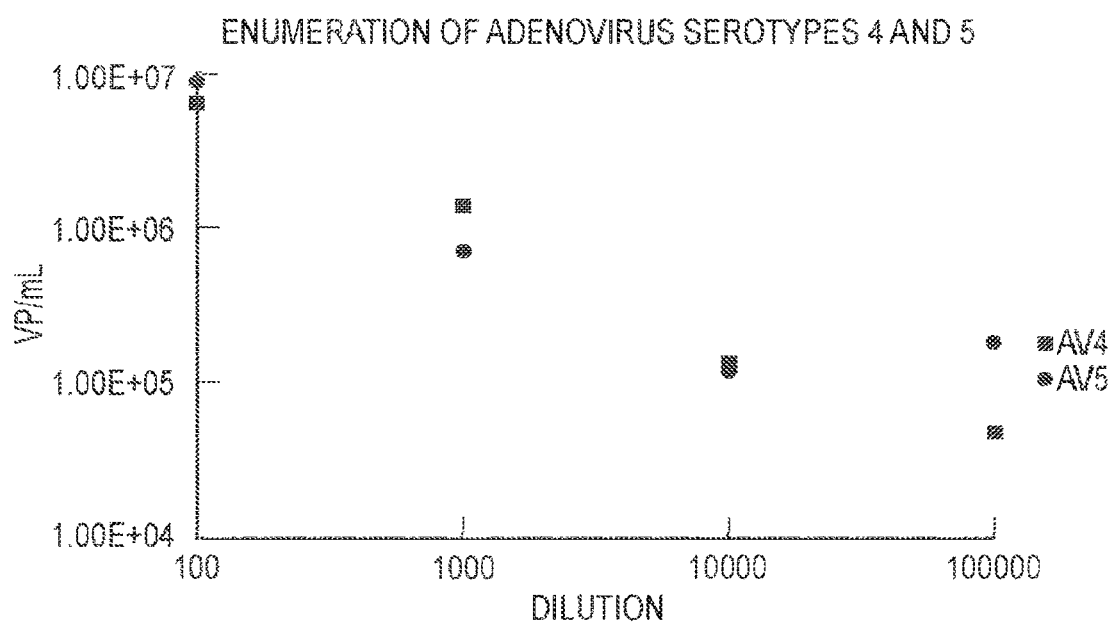
FIG. 19 is a plot summarizing results for Example 7 presented below.

Results are summarized in FIG. 19, which shows a plot of adenovirus concentration for each dilution of the dilution series for each of the different serotypes determined by flow cytometry as a function of dilution factor. Both the vertical and horizontal axes are log-scale. As seen in FIG. 19, the concentrations for each dilution series fall almost on a line indicating that the CF-8C4 binds with both serotypes, although data tend to diverge at high dilution factors where concentrations are at or below the detection limit of the flow cytometer (about 105.5 particles per milliliter).

Example 8

Comparative flow cytometry tests are performed on adenovirus test formulations using the same fluorescent antibody stain as used in Example 1 (CF-8C4) relative to controls of an influenza virus and lentivirus, which are not antigenic for the 8C4 antibody. The adenovirus used in the test formulations is serotype 4. For all tests, the total concentration of the CF-8C4 antibody stain (both bound and unbound to adenovirus) in the test solutions is about 2.5 micrograms per milliliter. Six test solutions are prepared at different dilutions of stock adenovirus solution for each for the dilution series, to provide six different virus concentrations for testing in buffered solution. For a specificity control, the fluorescent antibody stain was tested against unrelated viruses of influenza and lentivirus types.

Figure 20:
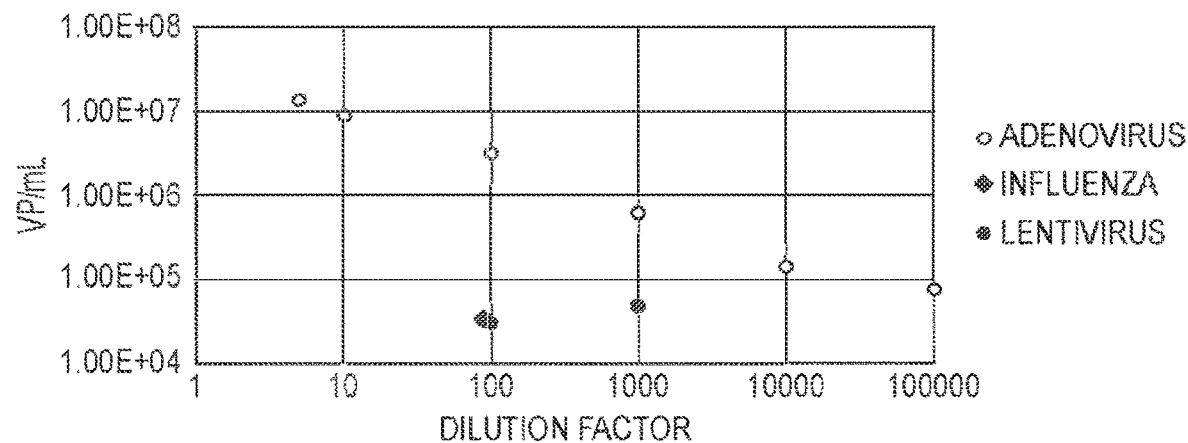
FIG. 20 is a plot summarizing results for Example 8 presented below.

Results are summarized in FIG. 20, which shows a plot of adenovirus concentration for each dilution determined by flow cytometry as a function of dilution factor for the different test formulations. Both the vertical and horizontal axes are log-scale. As seen in FIG. 20, for adenovirus the plot of concentrations for the dilution series show good linearity. FIG. 20 also summarizes data for the control formulations relative to an approximate lower detection limit for the flow cytometer (about 105.5 particles per milliliter), indicating that the fluorescent antibody stain failed to bind to the influenza virus and lentivirus controls, confirming the specificity of the fluorescent antibody stain.

Examples 9-10

Adeno-associated virus (AAV) are a family of small, nonenveloped viruses on the order of 20 nanometers in size and a 4.7 kb single stranded DNA genome. AAV has many serotypes that can infect both dividing and quiescent cells in human hosts. Adeno-associated virus are important virus for use in a number of virotherapy applications, including as gene therapy vector. Because of the extremely small size, adeno-associated virus is difficult to detect and accurately quantify, for example in manufacture operations for making recombinant adeno-associated virus and for dosing control.

Adeno-associated virus (AAV) is generally non-replicating, with replication generally requiring the presence of an additional factor. For example, AAV may be replicated in the presence of adenovirus using certain proteins of adenovirus genes. Some advantages of using AAV as a viral vector are the absence of pathogenicity, low host immune response and long-term expression. Accurate quantification of AAV during manufacture and formulation operations is important to monitor performance of manufacturing constructs and track product yields and to provide accurate dosing. Even though not pathogenic, excessive dosing with an infectious viral agent such as adeno-associated virus can cause serious problems to patients.

One of the most problematic steps is in the quantification of AAV viral vectors during growth, harvest, purification and release. Methods such as quantitative PCR and absorbance readings at 260 nm and 280 nm are highly variable, resulting in over- or under-estimation of particles present at any given step. The ramifications for manufacturing are lost product, delays and cost overruns, which are serious, yet minor in comparison to the risks associated with administering too little (no therapeutic effect) or too much (adverse immune response) product to patients. Clearly, there is a critical requirement for a rapid, more precise means of quantifying AAV viral particles used for vector-mediated gene therapy.

In Examples 9-10 below flow cytometry tests are performed on adeno-associated virus serotype 2 (AAV-2) using a fluorescent antibody stain including anti-AAV-2 monoclonal antibody A20 (PROGEN Biotechnik) conjugated with Alexa Fluor 532 dye (identified below as CF-A20 antibody stain). A20 is an antibody for a conformational epitope of assembled capsid of AAV-2 and AAV-3.

Example 9

Comparative flow cytometry tests are performed on AAV-2 test formulations using the fluorescent antibody stain CF-A20 relative to controls of AAV-5 and AAV-9 which are not antigenic for the A20 antibody. Two different AAV-2 test formulations are prepared using AAV-2 obtained from different commercial sources. For all tests, the total concentration of the CF-A20 antibody stain (both bound and unbound to AAV-2) in the test solutions is about 2.5 micrograms per milliliter. Five test solutions are prepared at different dilutions of stock virus solution for each for each dilution series, to provide five different virus concentrations for testing in buffered solution. For a specificity control, the fluorescent antibody stain was tested against the AAV-5 and AAV-9 serotypes, as well as buffered solution including CF-A20 but absent virus of any type.

Figure 21:
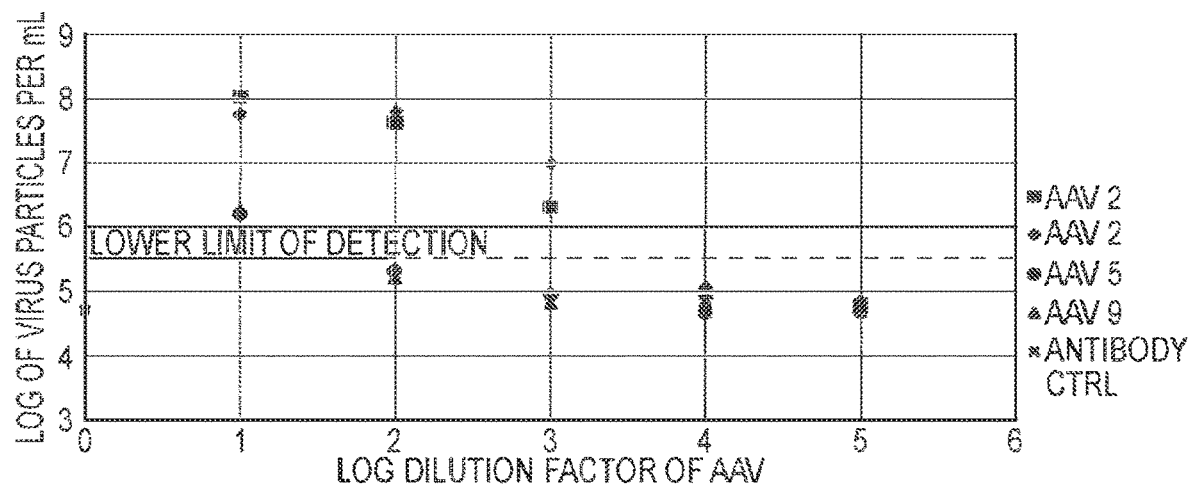
FIG. 21 is a plot summarizing results for Example 9 presented below.

Results are summarized in FIG. 21, which shows a plot of AAV-2 concentration for each AAV-2 sample determined by flow cytometry as a function of dilution factor for the CF-A20 stain tests and for the controls. Both the vertical and horizontal axes are log-scale. As seen in FIG. 21, AAV-2 concentrations indicated for the CF-A20 tests are close for each of the two AAV-2 test formulations. FIG. 21 also summarizes data for the control formulations relative to an approximate lower detection limit for the flow cytometer (about 105.5 particles per milliliter). The results demonstrate that data from the antibody stain-treated AAV-2 samples were reasonably consistent between different sources of AAV-2. In addition, the antibody failed to bind to AAV-5 or AAV-9, confirming the specificity of the fluorescent antibody stain for AAV-2 relative to those other serotypes. Furthermore, the fluorescent antibody stain did not increase background to unacceptable levels when added to the blank medium.

Example 10

Figure 22:
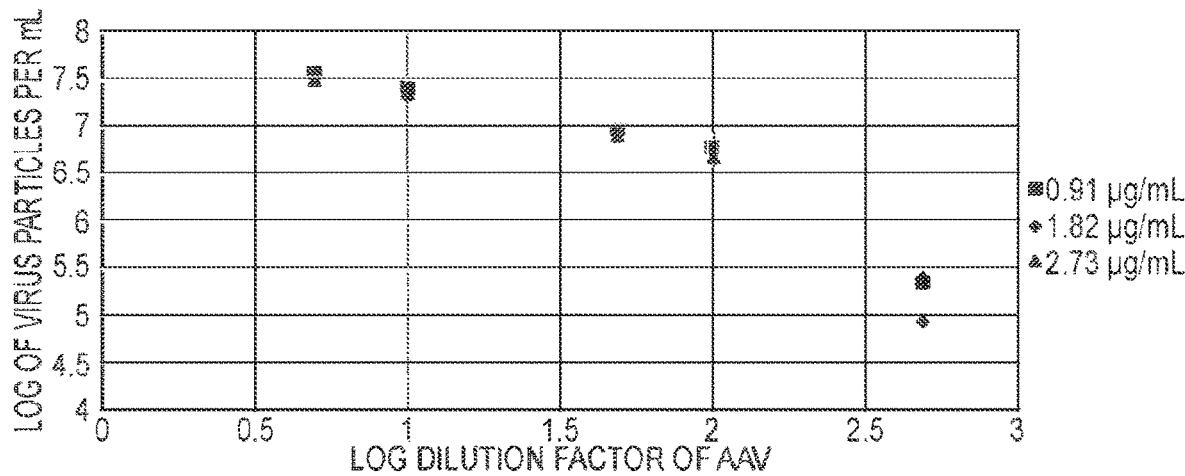
FIG. 22 is a plot summarizing some results for Example 10 presented below.
Figure 23:
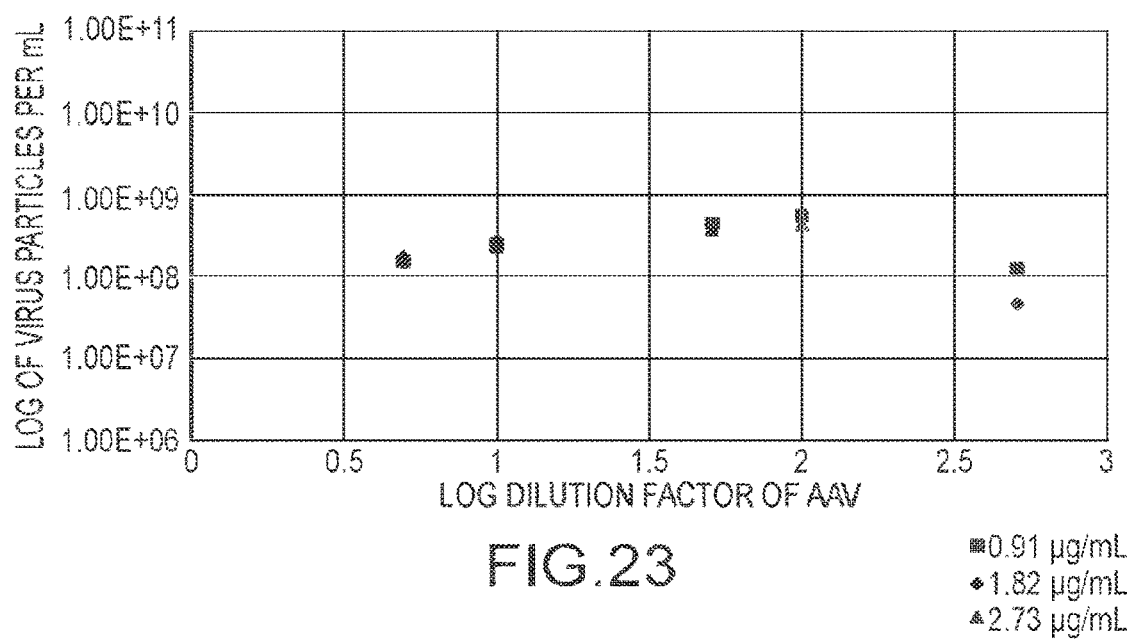
FIG. 23 is a plot summarizing some results for Example 10 presented below.
Figure 24:
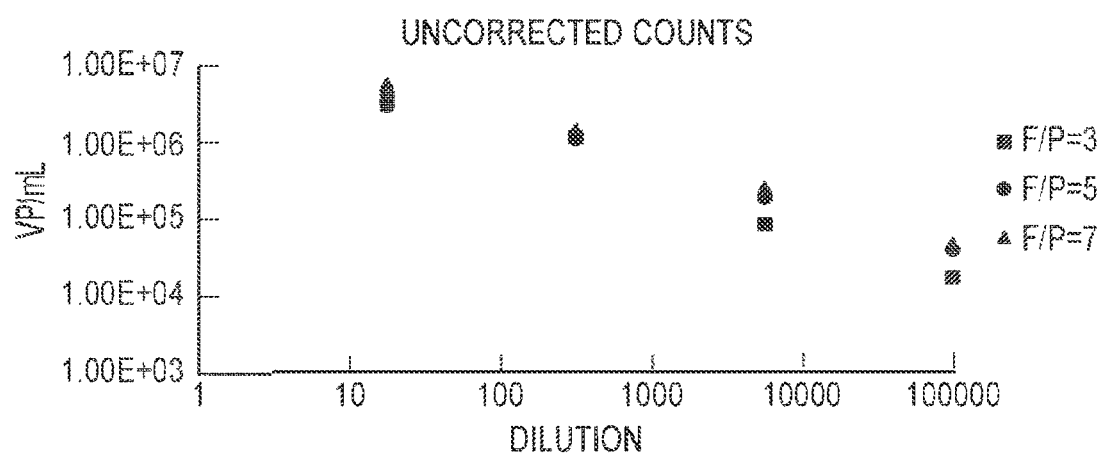
FIG. 24 is a plot summarizing some results for Example 11 presented below.
Figure 25:
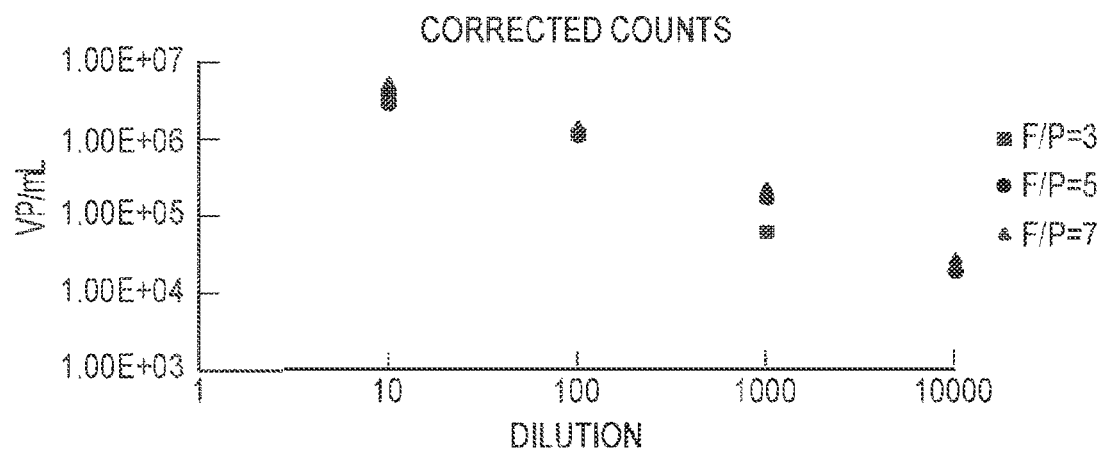
FIG. 25 is a plot summarizing some results for Example 11 presented below.
Figure 26:
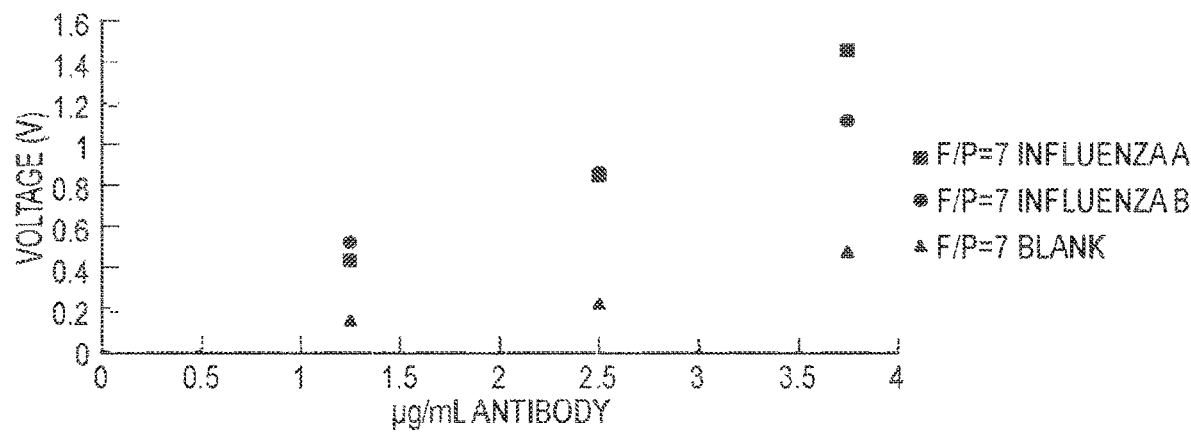
FIG. 26 is a plot summarizing results for Example 12 presented below.
Figure 27:
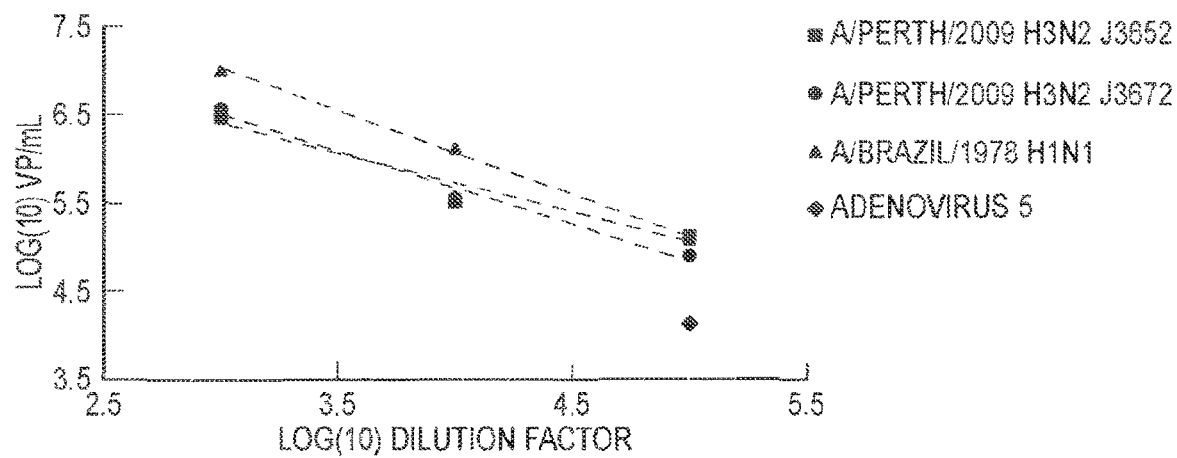
FIG. 27 is a plot summarizing some results for Example 13 presented below.
Figure 28:
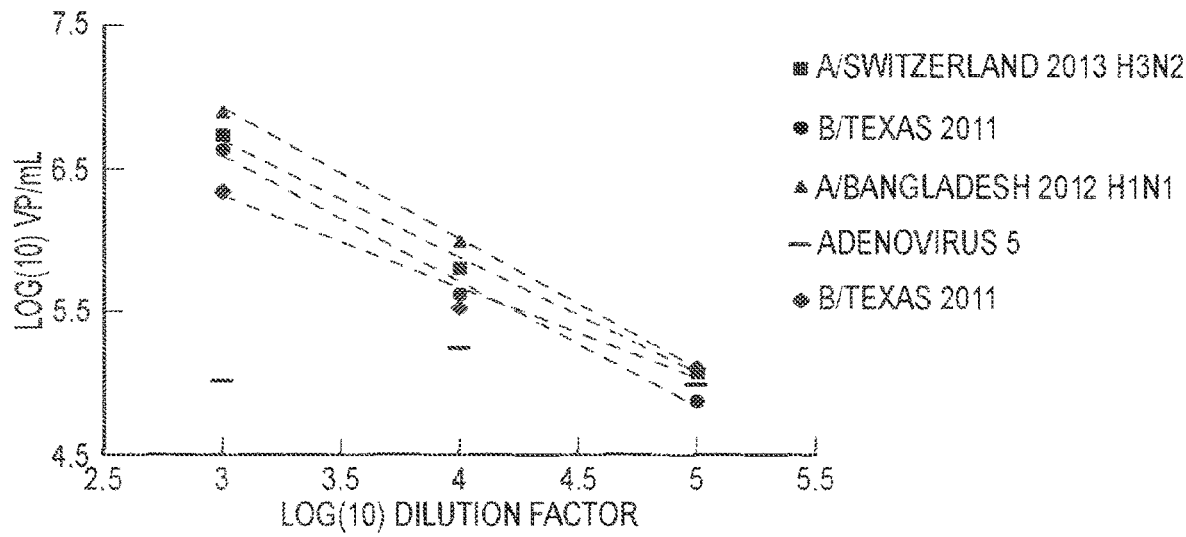
FIG. 28 is a plot summarizing some results for Example 13 presented below.
Figure 29:
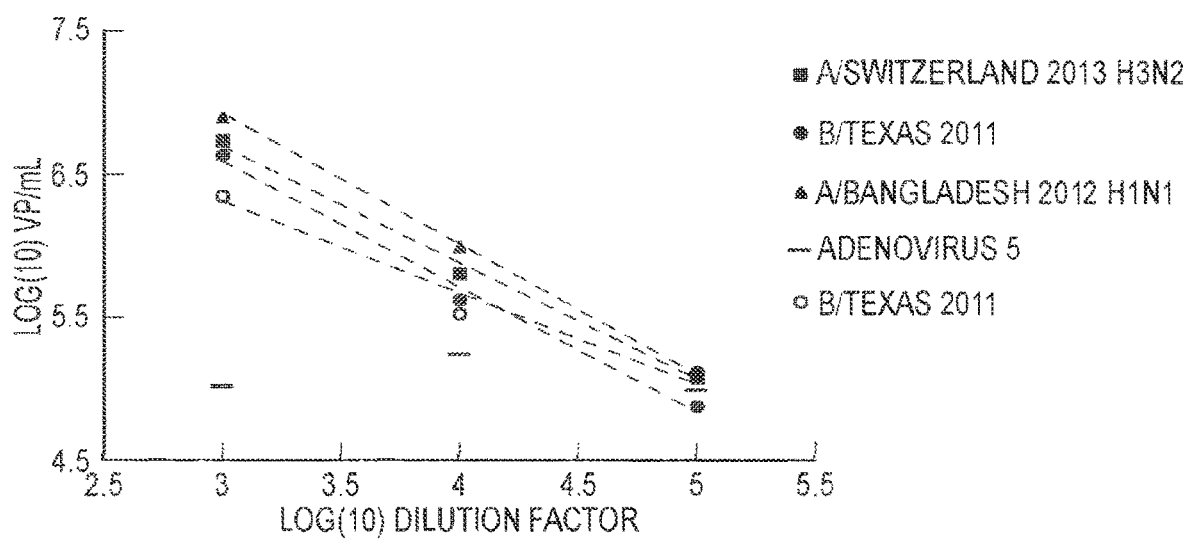
FIG. 29 is a plot summarizing some results for Example 13 presented below.
Figure 30:
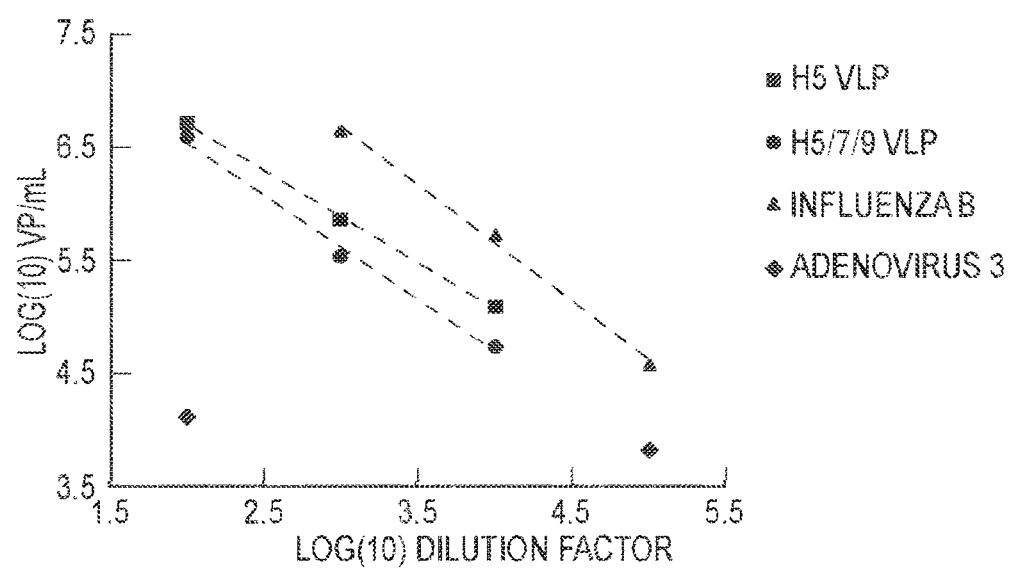
FIG. 30 is a plot summarizing some results for Example 13 presented below.

Flow cytometry dilution series using a variety of antibody stain concentrations are performed against a titration of AAV-2 solution containing about 1×105 to 1×108 AAV-2 particles per milliliter. Each dilution series includes flow cytometry of 200 microliter samples prepared at different dilutions of the stock AAV-2 solution, with all samples in each dilution series containing the same concentration of the fluorescent antibody stain. Three dilution series are run at antibody stain concentrations of about 0.91, 1.82 and 2.73 micrograms of CF-A20 antibody stain per milliliter of sample. Flow cytometry tests are performed to detect and evaluate for fluorescent emissions from stained AAV-2. Results of the flow cytometry tests for each dilution series are summarized in FIGS. 22 and 23. FIG. 22 shows a plot of uncorrected AAV-2 concentration (virus particles per milliliter) as determined for the samples by the flow cytometry tests, whereas FIG. 23 shows a plot of the same data but corrected the dilution factor. Both figures are log-log plots. FIGS. 22 and 23 both show generally good results (close to linear fit) at intermediate dilution factors, with the flow cytometry results corrected for dilution shown in FIG. 23 being close to the actual AAV-2 concentrations of the AAV-2 stock solution for the intermediate dilution factors. At lower dilution factors (higher AAV-2 concentrations in the sample) and higher dilution factors (lower AAV-2 concentrations in samples) results tend to degrade, which may indicate lower counts due to possible agglomeration of some AAV-2 particles at the lower dilution factors and higher counts due to possible interference from background signals from unbound antibody stain at the higher dilution factors.

Examples 11-13

In Examples 11-13 below, flow cytometry tests are performed for various influenza virus viral types using a fluorescent antibody stain including M149 polyclonal antibody (rabbit polyclonal antibody to human influenza A, B—Clontech/Takara) conjugated with a dye of CF532 (identified below as M140-532 antibody stain)

Example 11

Example M149-532 fluorescent antibody stain formulations are prepared with an F/P ratios of 3, 5 and 7. Test formulations for flow cytometry testing are prepared including type A influenza virus particles over a titration of unassociated influenza virus per milliliter and subjected to flow cytometry testing with each of the three formulations of M149-532 fluorescent antibody stain. Flow cytometry dilution series are run on using each of the different M149-532 formulations with a total concentration of about 2.5 micrograms per milliliter of the respective M149-532 fluorescent antibody stain for each of the flow cytometry runs. Results of the flow cytometry tests for the different dilution series are summarized in FIGS. 24 and 25. FIG. 24 shows uncorrected virus particle counts per milliliter (not corrected for background signals) and FIG. 25 shows corrected virus particle counts per milliliter (corrected for background signals). As shown in both FIGS. 24 and 25, tests using F/P ratio of 5 and 7 demonstrate good results (nearly linear) and consistent flow cytometry results across the dilution series, whereas the tests using F/P ratio of 3 show consistent results for the highest virus particle concentration tested (dilution factor 10×), but not at the lower concentration points (dilution factors of 1000× and 10,000×) where measured virus particles per milliliter drop off considerably. Notably, even after correcting for background, good and consistent results are obtained across the entire dilution series for the tests using F/P ratios of 5 and 7, but for the 10,000× dilution test using an F/P ratio of 3 the labeled virus particle detection peaks were not distinguishable from background. The F/P ratio of 3 does not appear to be sufficient to adequately conjugate with all of the antibody in the antibody stain, and so a significant number of antibody molecules remain unconjugated with fluorophore and may bind with virus particles but do not contribute to fluorescent emission response of the labeled virus particles. In contrast, using for both the F/P ratios of 5 and 7, there appears to be conjugation of fluorophore with all or nearly all of the antibody molecules, but without causing significant fluorescent emission quenching due to fluorophore crowding on the antibody molecules.

Example 12

Test formulations including influenza A virus or influenza B virus are prepared at concentrations of about 1×107 unassociated virus particles per milliliter and containing various concentrations of M149-532 fluorescent antibody stain (1.25, 2.5 and 3.75 micrograms per milliliter for influenza B test formulations and 1.25 and 3.75 micrograms per milliliter for influenza A test formulations). Blank formulations including corresponding concentrations (1.25, 2.5 and 3.75 micrograms per milliliter) of M149-532 and no virus particles are also prepared. The different test formulations and blank formulations are subjected to flow cytometry. FIG. 26 summarizes measured average peak height voltages indicative of detection of fluorescently stained virus particles for the different M149-532 concentrations in test formulations and background voltage peaks of the blank formulations. As shown in FIG. 26, peak height of voltage signals from stained influenza A and B virus increase with increasing concentration of fluorescent antibody stain, as do background peaks from the blank formulations. Notably, the spread between influenza B formulation peak height voltage and corresponding blank voltage peak increases significantly going from 1.25 to 2.5 micrograms per milliliter of fluorescent antibody stain, but does not similarly increase going from 2.5 to 3.75 micrograms per milliliter. Testing even higher concentrations of fluorescent antibody stain would start to show degradation of discrimination between stained virus particle peak height voltage and background voltage peaks from unbound fluorescent antibody stain from higher background voltage peaks from higher concentrations of unbound fluorescent antibody stain and stain agglomerates.

Example 13

Test formulations are prepared for a number of different virus-size particles of influenza viral type, including several serotypes of influenza A virus, influenza B virus and some virus-like particles including different hemagglutinin (H) subtypes. Some control formulations including the fluorescent antibody stain and either adenovirus serotype 3 or adenovirus serotype 5 are also prepared. Flow cytometry tests are performed for a dilution series for each test formulation and each control formulation, with each dilution sample subjected to flow cytometry including a concentration of M149-532 fluorescent antibody stain of about 2.5 micrograms per milliliter. Table 4 summarizes the different virus size particles for the test formulations and control formulations.

TABLE 4

| Virus-Size Particles Type | Specific Particles Tested | |
|---|---|---|
| A-Type Influenza Virus | A/Switzerland/2013 H3N2 | |
| A-Type Influenza Virus | A/Puerto Rico/1934 H1N1 | |
| A-Type Influenza Virus | A/Perth/2009 H3N2 J3652 | |
| A-Type Influenza Virus | A/Perth/2009 H3N2 J3672 | |
| A-Type Influenza Virus | A/Brazil/1978 H1N1 | |
| A-Type Influenza Virus | A/Switzerland/2013 H3N2 | |
| A-Type Influenza Virus | A/Bangladesh/2012 H1N1 | |
| B-Type Influenza Virus | B/Texas 2011 | |
| B-Type Influenza Virus | Influenza B virus | |
| Virus-like Particles of influenza virus viral type | H5 VLP | virus-like particles with H5 subtype of hemagglutinin |
| Virus-like Particles of influenza virus viral type | H5/7/9 VLP | virus-like particles with H5, H7 and H9 hemagglutinin subtypes |
| Adenovirus (Control) | Adenovirus 3 serotype | |
| Adenovirus (Control) | Adenovirus 5 serotype | |

Results are summarized in FIGS. 27-31, which show plots of measured particle concentration as a function of dilution factor for all of these test formulations and control formulations. As seen in FIGS. 26-30, all of the test formulations including virus-size particles of an influenza virus viral type show good results (close to linear fit) across the dilution series, whereas results for the adenovirus control formulations demonstrate specificity of the M149-532 fluorescent antibody stain, which failed to bind with the adenovirus particles.

Example Implementation Combinations

Some example implementation combinations, and for various types of implementation applications, which may be the subject of claims with or without additional features as disclosed above, are disclosed as follows:

1. A method for evaluating a biological material sample for unassociated virus-size particles having a particular epitope, the method comprising:
subjecting to flow cytometry a fluid sample comprising at least a portion of the biological material sample, wherein the fluid sample comprises a fluorescent antibody stain capable of binding, directly or indirectly, with the particular epitope, the flow cytometry comprising:
flowing the fluid sample through a flow cell of a flow cytometer;
subjecting the fluid sample flowing through the flow cell to excitation radiation capable of causing a fluorescent emission response from the fluorescent antibody stain; and
detecting radiation from the flow cell within a wavelength range of the fluorescent emission and evaluating the detected radiation to identify detection events indicative of passage through the flow cell of unassociated labeled particles of virus size including a said virus-size particle having the epitope and the fluorescent antibody stain.

For Some Virus-Like Particle Applications:

2. A method according to example implementation combination 1, wherein the biological material sample is suspected of including virus-like particles.

3. A method according to example implementation combination 2, wherein the virus-size particles are baculovirus virus particles of a different viral type than the virus-like particles and the detection events are indicative of passage through the flow cell of the unassociated labeled particles including a said virus particle. As an enhancement, the fluorescent antibody stain may include antibody for binding with baculovirus gp64 envelope glycoprotein as an epitope, and optionally such an antibody may be monoclonal (e.g., AcV1 monoclonal antibody).

4. A method according to example implementation combination 3, wherein:
the fluorescent antibody stain is a first fluorescent antibody stain, the epitope is a first epitope, the fluorescent emission is a first fluorescent emission, the detecting is first detecting, the detection event is a first detection event and the virus-like particles have a second epitope that is different than the first epitope;
the fluid sample includes a second fluorescent antibody stain different than the first fluorescent antibody stain and capable of binding, directly or indirectly, with a second epitope different than the first epitope, the second fluorescent antibody stain having a second fluorescent emission response to the excitation radiation that is different than the first fluorescent emission response; and
the flow cytometry comprises second detecting for second radiation from the flow cell within a wavelength range of the second fluorescent emission and evaluating the detected second radiation for detection events indicative of passage through the flow cell of second unassociated labeled particles of virus size including a said virus-like particle and the second fluorescent antibody stain.

5. A method according to any one of example implementation combinations either one of example implementation combination 3 or example implementation combination 4, wherein the second epitope is indicative of a viral type selected from the group consisting of rhabdovirus, nodavirus, influenza virus, adenovirus and adeno-associated virus.

6. A method according to example implementation combination 2, wherein the virus-size particles are the virus-like particles.

7. A method according to example implementation combination 6, wherein the virus-size particles have a viral type selected from the group consisting of rhabdovirus, nodavirus, influenza virus, adenovirus and adeno-associated virus.

8. A method according to example implementation combination 2, wherein the virus-size particles are virus particles of a different viral type than the virus-like particles and the detection events are indicative of passage through the flow cell of the unassociated labeled particles including a said virus particle.

9. A method according to example implementation combination 8, wherein:
the fluorescent antibody stain is a first fluorescent antibody stain, the epitope is a first epitope, the fluorescent emission is a first fluorescent emission, the detecting is first detecting, the detection event is a first detection event and the virus-like particles have a second epitope that is different than the first epitope;
the fluid sample includes a second fluorescent antibody stain different than the first fluorescent antibody stain and capable of binding, directly or indirectly, with a second epitope different than the first epitope, the second fluorescent antibody stain having a second fluorescent emission response to the excitation radiation that is different than the first fluorescent emission response; and
the flow cytometry comprises second detecting for second radiation from the flow cell within a wavelength range of the second fluorescent emission and evaluating the detected second radiation for detection events indicative of passage through the flow cell of second unassociated labeled particles of virus size including a said virus-like particle and the second fluorescent antibody stain.

10. A method according to example implementation combination 9, wherein the first epitope is indicative of a baculovirus viral type. As an enhancement, the first fluorescent antibody stain may include antibody for binding with baculovirus gp64 envelope glycoprotein as an epitope, and optionally such an antibody may be monoclonal (e.g., AcV1 monoclonal antibody).

11. A method according to any one of example implementation combinations either one of example implementation combination 8 or example implementation combination 9, wherein the second epitope is indicative of a viral type selected from the group consisting of rhabdovirus, nodavirus, influenza virus, adenovirus and adeno-associated virus.

12. A method according to any one of example implementation combinations 2-11, wherein the epitope is a first epitope, the flow cytometry is first flow cytometry, the fluid sample is a first fluid sample including a first portion of the of the biological material sample, the unassociated labeled particles are first unassociated labeled particles and the excitation radiation is first excitation radiation, and the method comprises:
subjecting to flow cytometry a second fluid sample comprising a second portion of the biological material sample, wherein the fluid sample comprises a second fluorescent antibody stain that is different than the first antibody stain and is capable of binding, directly or indirectly, with a second epitope that is different than the first epitope, the second flow cytometry comprising:
flowing the second fluid sample through a flow cell of a flow cytometer;
subjecting the second fluid sample flowing through the flow cell to second excitation radiation, which is the same as or different than the first excitation radiation, capable of causing a second fluorescent emission response that is different than the first fluorescent emission response from the second fluorescent antibody stain; and
detecting radiation from the flow cell within a wavelength range of the fluorescent emission and evaluating the detected radiation to identify detection events indicative of passage through the flow cell of second unassociated labeled particles of virus size including a particle of virus size having the second epitope and the second fluorescent antibody stain.

13. A method according to example implementation combination 12, wherein:
the first and second fluid samples each includes at least two different fluorescent antibody stains for binding, directly or indirectly, with two different epitopes; and
the first and second fluid samples each includes at least one fluorescent antibody stain that is not in the other said fluid sample.

14. A method according to example implementation combination 13, wherein the at least two fluorescent antibody stains of each said fluid sample are targeted to detecting at least two different types of particles of virus size in the said fluid sample and at least one said type of particle is different between the first sample fluid and the second sample fluid.

15. A method according to any one of example implementation combinations 2-14, wherein the biological material sample is a sample collected from a stage of a production operation for producing the virus-like particles during which the virus-like particles are expected to be present in the biological material.

16. A method for manufacturing a product comprising virus-like particles, the method comprising:
production processing to prepare a purified product including the virus-like particles, the production processing including:
generating the virus-like particles in a biological production operation;
harvesting from the biological production operation crude product comprising the virus-like particles generated during the generating;
purifying at least a portion of material of the crude product to prepare a purified product including the virus-like particles;
collecting a biological material sample from a stage of the production processing during which virus-like particles would be expected to be present in the biological material;
evaluating the sample for presence of particles of virus size having a particular epitope, the evaluating comprising performing the method according to any one of example implementation combinations 2-15.

17. A method according to example implementation combination 16, comprising performing the collecting multiple times to collect different said biological material samples to be evaluated from multiple different said stages and performing a said evaluating on each said collected biological material sample to be evaluated.

18. A method according to example implementation combination 17, wherein the multiple different said stages includes at least a first stage during the generating or the harvesting and a second stage during or after the purifying.

For Some Influenza Applications:

19. A method according to example implementation combination 1, wherein the biological material sample is suspected of including influenza virus particles.

20. A method according to example implementation combination 19, wherein the virus-size particles are the influenza virus particles.

21. A method according to example implementation combination 20, wherein:
the fluorescent antibody stain is a first fluorescent stain, the fluorescent emission is a first fluorescent emission, the detecting is first detecting and the detection event is a first detection event;
the fluid sample includes a second fluorescent stain for nucleic acid, the second fluorescent stain having a second fluorescent emission response, different than the first fluorescent emission response, to the excitation radiation when attached to nucleic acid; and
the flow cytometry comprises second detecting for second radiation from the flow cell within a wavelength range of the second fluorescent emission and evaluating the detected second radiation for detection events indicative of passage of particles of virus size containing nucleic acid stained with the second fluorescent stain; and
comparing results for the first detecting and the second detecting for identification of occurrences of a said first detection event that temporally coincides with a said second detection event that is further indicative of passage through the flow cell of a said unassociated labeled particle including a said influenza virus particle.

22. A method according to example implementation combination 20, wherein:
the fluorescent antibody stain is a first fluorescent antibody stain, the epitope is a first epitope, the fluorescent emission is a first fluorescent emission, the detecting is first detecting and the detection event is a first detection event;
the fluid sample includes a second fluorescent antibody stain different than the first fluorescent antibody stain and capable of binding, directly or indirectly, with a second epitope different than the first epitope, the second fluorescent antibody stain having a second fluorescent emission response to the excitation radiation that is different than the first fluorescent emission response; and
the flow cytometry comprises second detecting for second radiation from the flow cell within a wavelength range of the second fluorescent emission and evaluating the detected second radiation for detection events indicative of passage through the flow cell of unassociated labeled particles of virus size including a particle of virus size with the second epitope and the second fluorescent antibody stain.

23. A method according to example implementation combination 22, wherein the first epitope and the second epitope are indicative of the influenza virus.

24. A method according to example implementation combination 22, wherein the second epitope is indicative of a different influenza virus serotype than the first epitope.

25. A method according to any one of example implementation combinations 22-24, wherein the first epitope is indicative of presence of an influenza hemagglutinin antigen and the second epitope is indicative of presence of an influenza neuraminidase antigen.

26. A method according to any one of example implementation combinations 22-24, wherein the first epitope is indicative of presence of a first influenza hemagglutinin antigen and the second epitope is indicative of presence of a second influenza hemagglutinin antigen that is different than the first influenza hemagglutinin antigen.

27. A method according to any one of example implementation combinations 22-24, wherein the first epitope is indicative of presence of a first influenza neuraminidase antigen and the second epitope is indicative of presence of a second influenza neuraminidase antigen that is different than the first influenza neuraminidase antigen.

28. A method according to any one of example implementation combinations 22-27, wherein influenza virus is an influenza A virus or influenza B virus.

29. A method according to any one of example implementation combinations 20-28, wherein the epitope is a first epitope, the flow cytometry is first flow cytometry, the fluid sample is a first fluid sample including a first portion of the of the biological material sample, the unassociated labeled particles are first unassociated labeled particles and the excitation radiation is first excitation radiation, and the method comprises:
  subjecting to flow cytometry a second fluid sample comprising a second portion of the biological material sample, wherein the fluid sample comprises a second fluorescent antibody stain that is different than the first antibody stain and is capable of binding, directly or indirectly, with a second epitope that is different than the first epitope, the second flow cytometry comprising:
  flowing the second fluid sample through a flow cell of a flow cytometer;
  subjecting the second fluid sample flowing through the flow cell to second excitation radiation, which is the same as or different than the first excitation radiation, capable of causing a second fluorescent emission response that is different than the first fluorescent emission response from the second fluorescent antibody stain; and
  detecting radiation from the flow cell within a wavelength range of the fluorescent emission and evaluating the detected radiation to identify detection events indicative of passage through the flow cell of second unassociated labeled particles of virus size including a particle of virus size with the second epitope and the second fluorescent antibody stain.

30. A method according to example implementation combination 29, wherein:
  the first and second fluid samples each includes at least two different fluorescent antibody stains for binding, directly or indirectly, with two different epitopes; and
  the first and second fluid samples each includes at least one fluorescent antibody stain that is not in the other said fluid sample.

31. A method according to example implementation combination 30, wherein the at least two fluorescent antibody stains of each said fluid sample are targeted to detecting at least two different types of particles of virus size in the said fluid sample and at least one said type of particle is different between the first sample fluid and the second sample fluid.

32. A method according to example implementation combination 31, wherein at least one of the fluorescent antibody stains in the first fluid sample is targeted to detecting an epitope of a first influenza virus serotype and at least one of the fluorescent antibody stains in the second fluid sample is targeted to detecting an epitope of a second influenza virus serotype that is different than the first influenza virus serotype.

33. A method according to any one of example implementation combinations 20-32, wherein the biological material sample is a sample collected from a stage of a production operation for producing the influenza virus particles during which the influenza virus particles are expected to be present in the biological material.

34. A method for manufacturing a product comprising influenza virus particles, the method comprising:
  production processing to prepare a purified product including the influenza virus particles, the production processing including:
  generating the influenza virus particles in a biological production operation;
  harvesting from the biological production operation crude product comprising the influenza virus particles generated during the generating;
  purifying at least a portion of material of the crude product to prepare a purified product including the influenza virus particles;
  collecting a biological material sample from a stage of the production processing during which influenza virus particles would be expected to be present in the biological material;
  evaluating the sample for presence of particles of virus size having a particular epitope, the evaluating comprising performing the method according to any one of example implementation combinations 19-34.

35. A method according to example implementation combination 34, comprising performing the collecting multiple times to collect different said biological material samples to be evaluated from multiple different said stages and performing a said evaluating on each said collected biological material sample to be evaluated.

36. A method according to example implementation combination 35, wherein the multiple different said stages includes at least a first stage during the generating or the harvesting and a second stage during or after the purifying.

For Some Baculovirus Applications:

37. A method according to example implementation combination 1, wherein the biological material sample is suspected of including baculovirus particles.

38. A method according to example implementation combination 37, wherein the virus-size particles are the baculovirus particles. As an enhancement, the fluorescent antibody stain may include antibody for binding with baculovirus gp64 envelope glycoprotein as an epitope, and optionally such an antibody may be monoclonal (e.g., AcV1 monoclonal antibody).

39. A method according to example implementation combination 38, wherein:
  the fluorescent antibody stain is a first fluorescent stain, the fluorescent emission is a first fluorescent emission, the detecting is first detecting and the detection event is a first detection event;
  the fluid sample includes a second fluorescent stain for nucleic acid, the second fluorescent stain having a second fluorescent emission response, different than the first fluorescent emission response, to the excitation radiation when attached to nucleic acid; and
  the flow cytometry comprises second detecting for second radiation from the flow cell within a wavelength range of the second fluorescent emission and evaluating the detected second radiation for detection events indicative of passage of particles of virus size containing nucleic acid stained with the second fluorescent stain; and comparing results for the first detecting and the second detecting for identification of occurrences of a said first detection event that temporally coincides with a said second detection event that is further indicative of passage through the flow cell of a said unassociated labeled particle including a said baculovirus particle.

40. A method according to example implementation combination 38, wherein:

the fluorescent antibody stain is a first fluorescent antibody stain, the epitope is a first epitope, the fluorescent emission is a first fluorescent emission, the detecting is first detecting and the detection event is a first detection event;

the fluid sample includes a second fluorescent antibody stain different than the first fluorescent antibody stain and capable of binding, directly or indirectly, with a second epitope different than the first epitope, the second fluorescent antibody stain having a second fluorescent emission response to the excitation radiation that is different than the first fluorescent emission response; and the flow cytometry comprises second detecting for second radiation from the flow cell within a wavelength range of the second fluorescent emission and evaluating the detected second radiation for detection events indicative of passage through the flow cell of unassociated labeled particles of virus size including a particle of virus size with the second epitope and the second fluorescent antibody stain.

41. A method according to example implementation combination 40, wherein the first epitope is indicative of baculovirus and the second epitope is indicative of a second viral type other than baculovirus.

42. A method according to example implementation combination 41, wherein the second viral type is selected from the group consisting of rhabdovirus, nodavirus, influenza virus, adenovirus and adeno-associated virus.

43. A method according to any one of example implementation combinations 38-42, wherein the epitope is a first epitope, the flow cytometry is first flow cytometry, the fluid sample is a first fluid sample including a first portion of the of the biological material sample, the unassociated labeled particles are first unassociated labeled particles and the excitation radiation is first excitation radiation, and the method comprises:

subjecting to flow cytometry a second fluid sample comprising a second portion of the biological material sample, wherein the fluid sample comprises a second fluorescent antibody stain that is different than the first antibody stain and is capable of binding, directly or indirectly, with a second epitope that is different than the first epitope, the second flow cytometry comprising:

flowing the second fluid sample through a flow cell of a flow cytometer;

subjecting the second fluid sample flowing through the flow cell to second excitation radiation, which is the same as or different than the first excitation radiation, capable of causing a second fluorescent emission response that is different than the first fluorescent emission response from the second fluorescent antibody stain; and detecting radiation from the flow cell within a wavelength range of the fluorescent emission and evaluating the detected radiation to identify detection events indicative of passage through the flow cell of second unassociated labeled particles of virus size including a particle of virus size with the second epitope and the second fluorescent antibody stain.

44. A method according to example implementation combination 43, wherein:

the first and second fluid samples each includes at least two different fluorescent antibody stains for binding, directly or indirectly, with two different epitopes; and the first and second fluid samples each includes at least one fluorescent antibody stain that is not in the other said fluid sample.

45. A method according to example implementation combination 44, wherein the at least two fluorescent antibody stains of each said fluid sample are targeted to detecting at least two different types of particles of virus size in the said fluid sample and at least one said type of particle is different between the first sample fluid and the second sample fluid.

46. A method according to example implementation combination 45, wherein at least one of the fluorescent antibody stains in the first fluid sample is targeted to detecting an epitope of baculovirus and at least one of the fluorescent antibody stains in the second fluid sample is targeted to detecting an epitope of a second viral type that is different than baculovirus.

47. A method according to any one of example implementation combinations 38-46, wherein the biological material sample is a sample collected from a stage of a production operation for producing the baculovirus particles during which the baculovirus particles are expected to be present in the biological material.

48. A method for manufacturing a product comprising baculovirus particles, the method comprising:

production processing to prepare a purified product including the baculovirus particles, the production processing including:

generating the baculovirus particles in a biological production operation;

harvesting from the biological production operation crude product comprising the baculovirus particles generated during the generating;

purifying at least a portion of material of the crude product to prepare a purified product including the baculovirus particles;

collecting a biological material sample from a stage of the production processing during which baculovirus particles would be expected to be present in the biological material;

evaluating the sample for presence of particles of virus size having a particular epitope, the evaluating comprising performing the method according to any one of example implementation combinations 37-47.

49. A method according to example implementation combination 48, comprising performing the collecting multiple times to collect different said biological material samples to be evaluated from multiple different said stages and performing a said evaluating on each said collected biological material sample to be evaluated.

50. A method according to example implementation combination 49, wherein the multiple different said stages includes at least a first stage during the generating or the harvesting and a second stage during or after the purifying.

51. A method according to any one of example implementation combinations 48-49, wherein the baculovirus have been modified to express recombinant protein, and the method comprises generating and recovering the recombinant protein.

For Some Virus Applications:

52. A method according to example implementation combination 1, wherein the biological material sample is suspected of including virus particles of a viral type.

53. A method according to example implementation combination 52, wherein the virus-size particles are the virus particles of the viral type.

54. A method according to example implementation combination 53, wherein:
the fluorescent antibody stain is a first fluorescent stain, the fluorescent emission is a first fluorescent emission, the detecting is first detecting and the detection event is a first detection event;
the fluid sample includes a second fluorescent stain for nucleic acid, the second fluorescent stain having a second fluorescent emission response, different than the first fluorescent emission response, to the excitation radiation when attached to nucleic acid; and
the flow cytometry comprises second detecting for second radiation from the flow cell within a wavelength range of the second fluorescent emission and evaluating the detected second radiation for detection events indicative of passage of particles of virus size containing nucleic acid stained with the second fluorescent stain; and
comparing results for the first detecting and the second detecting for identification of occurrences of a said first detection event that temporally coincides with a said second detection event that is further indicative of passage through the flow cell of a said unassociated labeled particle including a said virus particle.

55. A method according to example implementation combination 53, wherein:
the fluorescent antibody stain is a first fluorescent antibody stain, the epitope is a first epitope, the fluorescent emission is a first fluorescent emission, the detecting is first detecting and the detection event is a first detection event;
the fluid sample includes a second fluorescent antibody stain different than the first fluorescent antibody stain and capable of binding, directly or indirectly, with a second epitope different than the first epitope, second fluorescent antibody stain having a second fluorescent emission response to the excitation radiation that is different than the first fluorescent emission response; and
the flow cytometry comprises second detecting for second radiation from the flow cell within a wavelength range of the second fluorescent emission and evaluating the detected second radiation for detection events indicative of passage through the flow cell of unassociated labeled particles of virus size including a particle of virus size with the second epitope and the second fluorescent antibody stain.

56. A method according to example implementation combination 55, wherein the first epitope is indicative of a first viral type and the second epitope is indicative of a second viral type other than the first viral type.

57. A method according to example implementation combination 56, wherein the first viral type is baculovirus. As an enhancement, the first fluorescent antibody stain may include antibody for binding with baculovirus gp64 envelope glycoprotein as an epitope, and optionally such an antibody may be monoclonal (e.g., AcV1 monoclonal antibody).

58. A method according to either one of example implementation combination 56 or example implementation combination 57, wherein the second viral type is selected from the group consisting of rhabdovirus, nodavirus, influenza virus, adenovirus and adeno-associated virus.

59. A method according to any one of example implementation combinations 53-58, wherein the epitope is a first epitope, the flow cytometry is first flow cytometry, the fluid sample is first fluid sample including a first portion of the of the biological material sample, the unassociated labeled particles are first unassociated labeled particles and the excitation radiation is first excitation radiation, and the method comprises:
subjecting to flow cytometry a second fluid sample comprising a second portion of the biological material sample, wherein the fluid sample comprises a second fluorescent antibody stain that is different than the first antibody stain and is capable of binding, directly or indirectly, with a second epitope that is different than the first epitope, the second flow cytometry comprising:
flowing the second fluid sample through a flow cell of a flow cytometer;
subjecting the second fluid sample flowing through the flow cell to second excitation radiation, which is the same as or different than the first excitation radiation, capable of causing a second fluorescent emission response that is different than the first fluorescent emission response from the second fluorescent antibody stain; and
detecting radiation from the flow cell within a wavelength range of the fluorescent emission and evaluating the detected radiation to identify detection events indicative of passage through the flow cell of second unassociated labeled particles of virus size including a particle of virus size with the second epitope and the second fluorescent antibody stain.

60. A method according to example implementation combination 59, wherein:
the first and second fluid samples each includes at least two different fluorescent antibody stains for binding, directly or indirectly, with two different epitopes; and
the first and second fluid samples each includes at least one fluorescent antibody stain that is not in the other said fluid sample.

61. A method according to example implementation combination 60, wherein the at least two fluorescent antibody stains of each said fluid sample are targeted to detecting at least two different types of particles of virus size in the said fluid sample and at least one said type of particle is different between the first sample fluid and the second sample fluid.

62. A method according to example implementation combination 61, wherein at least one of the fluorescent antibody stains in the first fluid sample is targeted to detecting an epitope of a first viral type and at least one of the fluorescent antibody stains in the second fluid sample is targeted to detecting an epitope of a second viral type that is different than the first viral type.

63. A method according to any one of example implementation combinations 53-62, wherein the biological material sample is a sample collected from a stage of a production operation for producing the virus particles during which the virus particles are expected to be present in the biological material.

64. A method for manufacturing a product comprising virus particles, the method comprising:
production processing to prepare a purified product including the virus particles, the production processing including:

generating the virus particles in a biological production operation;

harvesting from the biological production operation crude product comprising the virus particles generated during the generating;

purifying at least a portion of material of the crude product to prepare a purified product including the virus particles;

collecting a biological material sample from a stage of the production processing during which virus particles would be expected to be present in the biological material;

evaluating the sample for presence of particles of virus size having a particular epitope, the evaluating comprising performing the method according to any one of example implementation combinations 52-63.

65. A method according to example implementation combination 64, comprising performing the collecting multiple times to collect different said biological material samples to be evaluated from multiple different said stages and performing a said evaluating on each said collected biological material sample to be evaluated.

66. A method according to example implementation combination 65, wherein the multiple different said stages includes at least a first stage during the generating or the harvesting and a second stage during or after the purifying.

For Some Nanoparticle Applications:

67. A method according to example implementation combination 1, wherein the virus-size particles are nanoparticles, which may or may not be exosomes.

Some Other Example Implementation Combinations:

68. A method according to any one of example implementation combinations 1-67, wherein the biological material in a said fluid sample is purified biological material with larger-size components removed to a filtration size of not larger than 2 microns, and the fluid sample comprises a concentration of fluorescent antibody stain not bound in the unassociated labeled particles in a range of from 0.25 microgram per milliliter to 10 micrograms per milliliter of the fluid sample.

69. A method according to any one of example implementation combinations 1-68, wherein a said fluid sample as fed to the flow cytometer includes a total concentration of the fluorescent antibody stain in a range of from 0.25 microgram per milliliter to 10 micrograms per milliliter.

70. A method according to any one of example implementation combinations 1-69, wherein the unassociated labeled particles have a maximum cross dimension in a range of from 10 nanometers to 2 microns.

71. A method according to any one of example implementation combinations 1-70, wherein the excitation radiation includes radiation within a wavelength range of from 520 nanometers to 550 nanometers.

72. A method according to any one of example implementation combinations 1-71, wherein the fluorescent emission has a Stokes shift in wavelength of at least 10 nanometers.

73. A method according to any one of example implementation combinations 1-72, wherein a said fluid sample as fed to the flow cytometer comprises a concentration of the fluorescent antibody stain not bound in the unassociated labeled particles in a range of from 0.25 microgram per milliliter to 10 micrograms per milliliter.

74. A method according to any one of example implementation combinations 1-73, wherein a said fluid sample as fed to the flow cytometer has a concentration of the unassociated labeled particles in a range of from $1\times10^5$ to $1\times10^9$ particles per milliliter.

75. A method according to any one of example implementation combinations 1-74, wherein a said fluorescent antibody stain comprises a fluorophore attached to an antibody molecule.

76. A method according to example implementation combinations 75, wherein a said fluorescent antibody stain comprises an average of from 3 to 8 of the fluorophores attached per antibody molecule.

77. A method according to either one of example implementation combination 75 or example implementation combination 76, wherein the antibody molecules are monoclonal.

78. A method according to either one of example implementation combination 75 or example implementation combination 76, wherein the antibody molecules are polyclonal.

79. A method according to any one of example implementation combinations 1-78, wherein the flow cytometry comprises flowing a said fluid sample through the flow cell at a fluid sample flow rate in a range of from 250 to 3000 nanoliters per minute.

80. A method according to any one of example implementation combinations 1-79, comprising:

preparing the fluid sample, comprising mixing biological material to be evaluated for presence of the unassociated particles with the fluorescent antibody stain, the fluorescent antibody stain capable of binding, directly or indirectly, with the epitope to form the unassociated labeled particles of virus size.

81. A method according to example implementation combination 80, wherein the preparing a fluid sample comprises, prior to the mixing, purifying a crude sample of biological material to prepare the biological material for the fluid sample as subjected to the flow cytometry, the purifying comprising filtering out particles of the crude sample at a filtration size of not larger than 2 microns and chromatographic removal of at least a portion of impurities smaller than virus size.

82. A method according to example implementation combination 81, wherein the chromatographic removal comprises spin chromatography in a centrifuge.

83. A method according to any one of example implementation combinations 80-82, wherein the preparing a fluid sample comprises, after the mixing, not removing fluorescent antibody not bound in the unassociated labeled particles from the fluid sample prior to the flow cytometry.

84. A method according to any one of example implementation combinations 1-84, wherein the fluorescent antibody stain comprises a biotinylated antibody and a fluorophore conjugated streptavidin.

85. A method according to example implementation combination 84, wherein the fluorophore conjugated streptavidin is attached to the biotinylated antibody when provided to the mixing of any one of example implementation combinations 80-83.

86. A method according to example implementation combination 85, wherein the fluorophore conjugated streptavidin and the biotinylated antibody are provided in separate formulations to the mixing and the fluorophore conjugated streptavidin attaches to the biotinylated antibody in solution during the mixing.

87. A method according to any one of example implementation combinations 1-86, wherein the flow cytometry is in the absence of detecting for light scatter.

88. A method according to any one of example implementation combinations 1-87, wherein the fluid sample as fed to the flow cytometer includes a total concentration of the fluorescent antibody stain in a range of from 0.5 microgram per milliliter to 10 micrograms per milliliter.

89. A method according to any one of example implementation combinations 1-88, wherein the fluid sample as fed to the flow cytometer comprises a concentration of the fluorescent antibody stain not bound in the unassociated labeled particles in a range of from 0.5 microgram per milliliter to 10 micrograms per milliliter.

90. A method according any one of example implementation combinations 1-89, wherein the fluorescent antibody stain is a first fluorescent stain and the fluid sample comprises a second fluorescent stain having a second fluorescent emission response, different than the first fluorescent emission response of the first fluorescent stain, caused by the excitation radiation.

91. A method according to example implementation combination 90, wherein the second fluorescent stain comprises a fluorescent nucleic acid stain not specific to particle type.

92. A method according to example implementation combination 90, wherein:
the unassociated particles are first unassociated particles, the epitope is a first epitope, the unassociated particles are of a first particle type and the unassociated labeled particles are first unassociated labeled particles;
the second fluorescent stain is a second fluorescent antibody stain that is different than the first fluorescent antibody stain and is capable of binding with second unassociated particles of virus size having a second epitope indicative of a second particle type that is different than the first particle type to form second unassociated labeled particles of virus size; and
the method comprises detecting radiation from the flow cell within a wavelength range of the second fluorescent emission and evaluating the detected radiation to identify detection events indicative of passage of the second unassociated labeled particles through the flow cell.

93. A method according to any one of example implementation combinations 90-92, wherein the second fluorescent emission has a peak wavelength at least 20 nanometers different than a peak wavelength of the first fluorescent emission nanometers.

94. A method according to any one of example implementation combinations 1-93, wherein each said fluorescent antibody stain is capable of binding directly with a corresponding said unassociated particle to form the corresponding said unassociated labeled particle.

95. A method according to any one of example implementation combinations 1-94, wherein the flow cytometry comprises hydrodynamically focusing flow of the fluid sample with a sheath fluid and flowing the fluid sample and the sheath fluid through the flow cell.

96. A method according to any one of example implementation combinations 1-95, wherein the flow cytometry comprises separately detecting for at least two different fluorescent emissions and not detecting for light scatter.

97. A method according to any one of example implementation combinations 1-96, wherein the unassociated labeled particles are viral particles of a viral type.

98. A method according to example implementation combination 97, wherein the viral particles comprise a member selected from the group consisting of virus particles of the viral type, virus-like particles of the viral type and combinations thereof.

99. A method according to either one of example implementation combination 97 or example implementation combination 98, wherein the viral type is a baculovirus viral type.

100. A method according to either one of example implementation combination 97 or example implementation combination 98, wherein the viral type is an adenovirus viral type.

101. A method according to either one of example implementation combination 97 or example implementation combination 98, wherein the viral type is an adeno-associated virus viral type.

102. A method according to either one of example implementation combination 97 or example implementation combination 98, wherein the viral type is an influenza virus viral type.

103. A method according to any one of example implementation combinations 1-102, wherein the unassociated viral particles have a maximum cross-dimension in a range of from 10 nanometers to 2 microns.

104. A method according to any one of example implementation combinations 1-103, wherein the fluorescent antibody stain is a first fluorescent stain and the fluid sample comprises a second fluorescent stain having a second fluorescent emission response, different than the first fluorescent emission response of the first fluorescent stain, caused by the excitation radiation.

105. A method according to example implementation combination 104, wherein the second fluorescent stain comprises a fluorescent nucleic acid stain not specific to particle type.

106. A method according to example implementation combination 104, wherein:
the unassociated labeled particles are first unassociated labeled particles, the epitope is a first epitope, the virus-size particles are of a first virus-size particles, the viral type is a first viral type and the unassociated labeled particles are first unassociated labeled particles;
the second fluorescent stain is a second fluorescent antibody stain that is different than the first fluorescent antibody stain and is capable of binding with second virus-size particles having a second epitope indicative of a second viral type that is different than the first viral type to form second unassociated labeled particles of virus size; and
the method comprises detecting radiation from the flow cell within a wavelength range of the second fluorescent emission and evaluating the detected radiation to identify detection events indicative of passage of the second unassociated labeled particles through the flow cell.

107. A method according to example implementation combination 106, wherein the second fluorescent emission has a peak wavelength at least 20 nanometers different than a peak wavelength of the first fluorescent emission nanometers and the flow cytometry comprises separately detecting for at least the first and second fluorescent emissions and not detecting for light scatter.

108. A method according to example implementation combination 107, wherein the second virus-size particles comprise virus-like particles of the second viral type.

109. A method according to any one of example implementation combinations 1-108, wherein the virus-size particles are modified to express recombinant protein.

110. A method according to example implementation combination 109, wherein the flow cytometry is in the absence of detecting for light scatter.

111. A method according to example implementation combination 110, comprising preparing the fluid sample, the preparing the fluid sample comprising:
  mixing biological material to be evaluated for presence of the unassociated virus-size particles with the fluorescent antibody stain; and
  after the mixing, not removing fluorescent antibody not bound in the unassociated labeled particles from the fluid sample prior to flow cytometry 112. A method for manufacturing a product comprising virus-size particles of a viral type, the method comprising:
  production processing to prepare a purified product including the virus-size particles of the viral type, the production processing including:
  generating the virus-size particles in a biological production operation;
  harvesting from the biological production operation crude product comprising the virus-size particles generated during the generating;
  purifying at least a portion of material of the crude product to prepare a purified product including the virus-size particles;
  collecting a biological material sample from a stage of the production processing during which the virus-size particles would be expected to be present in the biological material;
  evaluating the sample for presence of particles of virus size having a particular epitope indicative of the viral type, the evaluating comprising performing the method according to any one of example implementation combinations 1-111.

113. A method according to example implementation combination 112, comprising performing the collecting multiple times to collect different said biological material samples to be evaluated from multiple different said stages and performing a said evaluating on each said collected biological material sample to be evaluated.

114. A method according to example implementation combination 113, wherein the multiple different said stages include at least a first stage during the generating or the harvesting and a second stage during or after the purifying.

115. A fluid sample for feed to a flow cytometer for flow cytometry evaluation, comprising;
  an aqueous liquid medium;
  unassociated labeled particles of virus size in the aqueous liquid medium at a concentration of from $1\times10^5$ to $1\times10^9$ of the unassociated labeled particles per milliliter, wherein the unassociated labeled particles each includes a virus-size particle of a viral type having a particular epitope indicative of the viral type and a fluorescent antibody stain specific for binding, directly or indirectly with the epitope; and
  a concentration of the unbound fluorescent antibody stain in the aqueous liquid medium, not bound in the unassociated labeled particles, in a range of from 0.25 microgram per milliliter to 10 micrograms per milliliter.

116. A fluid sample according to example implementation combination 115, wherein the concentration of the unbound fluorescent antibody stain in the aqueous liquid medium is in a range of from 0.5 microgram per milliliter to 10 micrograms per milliliter 117. A fluid sample according to either one of example implementation combination 115 or example implementation combination 116, wherein the fluid sample includes a total concentration of the fluorescent antibody stain in a range of from 0.25 microgram per milliliter to 10 micrograms per milliliter.

118. A fluid sample according to example implementation combination 117, wherein the total concentration of the fluorescent antibody stain is in a range of from 0.5 microgram per milliliter to 10 micrograms per milliliter 119. A fluid sample according to any one of example implementation combinations 115-118, wherein the biological material in the fluid sample is purified biological material with larger-size components removed to a filtration size of not larger than 2 microns.

120. A fluid sample according to any one of example implementation combinations 115-119, wherein the fluorescent antibody stain comprises fluorophore attached to antibody molecules and the fluorescent antibody stain in the fluid sample comprises an average of 3 to 8 of the fluorophores attached per antibody molecule.

121. A fluid sample according to any one of example implementation combinations 115-120, wherein antibody of the antibody stain is monoclonal.

122. A fluid sample according to any one of example implementation combinations 115-120, wherein antibody of the antibody stain is polyclonal.

123. A fluid sample according to any one of example implementation combinations 115-122, wherein the virus-size particles are modified to express recombinant protein.

124. A fluid sample according to any one of example implementation combinations 115-123, wherein:
  the fluorescent antibody stain is a first fluorescent stain having a first fluorescent emission; and
  the fluid sample includes a second fluorescent stain for nucleic acid, the second fluorescent stain having a second fluorescent emission, different than the first fluorescent emission.

125. A fluid sample according to any one of example implementation combinations 115-123, wherein:
  the fluorescent antibody stain is a first fluorescent antibody stain, the epitope is a first epitope, the fluorescent emission is a first fluorescent emission, the viral type is a first viral type and the unassociated labeled particles are first unassociated labeled particles of virus size;
  the fluid sample includes a second fluorescent antibody stain different than the first fluorescent antibody stain and capable of binding, directly or indirectly, with a second epitope different than the first epitope, the second epitope being indicative of a second viral type that is other than the first viral type and the second fluorescent antibody stain having a second fluorescent emission response that is different than the first fluorescent emission response.

126. A fluid sample according to example implementation combination 125, wherein the particle of virus size with the second epitope is a virus-like particle.

127. A fluid sample according to any one of example implementation combinations 115-126, wherein the viral type is of baculovirus.

128. A fluid sample according to any one of example implementation combinations 115-126, wherein the viral type is of adenovirus.

129. A fluid sample according to any one of example implementation combinations 115-126, wherein the viral type is of adeno-associated virus.

130. A fluid sample according to any one of example implementation combinations 115-126, wherein the viral type is of influenza virus.

For Some Other Baculovirus Applications:

1B. A flow cytometry method for evaluating a biological material sample for unassociated virus-size particles of a baculovirus viral type, the method comprising:
subjecting to flow cytometry a fluid sample comprising at least a portion of the biological material sample, wherein the fluid sample comprises a fluorescent antibody stain capable of binding, directly or indirectly, with an epitope of the baculovirus viral type, the flow cytometry comprising:
flowing the fluid sample through a flow cell of a flow cytometer;
subjecting the fluid sample flowing through the flow cell to excitation radiation capable of causing a fluorescent emission response from the fluorescent antibody stain; and
detecting radiation from the flow cell within a wavelength range of the fluorescent emission and evaluating the detected radiation to identify detection events indicative of passage through the flow cell of the unassociated labeled particles of virus size including a said virus-size particle of the baculovirus viral type bound with a portion of the fluorescent antibody stain.

2B. A flow cytometry method according to example implementation combination 1B, wherein the fluid sample as fed to the flow cytometer comprises a concentration of the fluorescent antibody stain not bound in the unassociated labeled particles in a range of from 0.25 (or 0.5) micrograms per milliliter to 10 micrograms per milliliter.

3B. A flow cytometry method according to example implementation combination 2B, wherein the fluid sample as fed to the flow cytometer includes a total concentration of the fluorescent antibody stain in a range of from 0.25 (or 0.5) microgram per milliliter to 10 micrograms per milliliter.

4B. A flow cytometry method according to any one of example implementation combinations 1B-3B, wherein the epitope is baculovirus gp64 envelope glycoprotein, and optionally the fluorescent antibody stain comprises AcV1 monoclonal antibody.

5B. A flow cytometry method according to any one of example implementation combinations 1B-4B, wherein the virus-size particles comprise baculovirus particles.

6B. A flow cytometry method according to example implementation combination 5B, wherein the baculovirus particles express recombinant protein.

7B. A flow cytometry method according to any one of example implementation combinations 1B-6B, wherein:
the fluorescent antibody stain is a first fluorescent stain, the fluorescent emission is a first fluorescent emission, the detecting is first detecting and the detection event is a first detection event;
the fluid sample includes a second fluorescent stain for nucleic acid, the second fluorescent stain having a second fluorescent emission response, different than the first fluorescent emission response, to the excitation radiation when attached to nucleic acid; and
the flow cytometry comprises second detecting for second radiation from the flow cell within a wavelength range of the second fluorescent emission and evaluating the detected second radiation for detection events indicative of passage of particles of virus size containing nucleic acid stained with the second fluorescent stain; and
comparing results for the first detecting and the second detecting for identification of occurrences of a said first detection event that temporally coincides with a said second detection event that is further indicative of passage through the flow cell of a said unassociated labeled particle including a said virus-size particle of a baculovirus viral type.

8B. A flow cytometry method according to any one of example implementation combinations 1B-6B, wherein:
the fluorescent antibody stain is a first fluorescent antibody stain, the epitope is a first epitope, the fluorescent emission is a first fluorescent emission, the detecting is first detecting, the viral type is a first viral type, the unassociated labeled particles are first unassociated labeled particles of virus size and the detection event is a first detection event;
the fluid sample includes a second fluorescent antibody stain different than the first fluorescent antibody stain and capable of binding, directly or indirectly, with a second epitope different than the first epitope, the second epitope being indicative of a second viral type that is other than baculovirus and the second fluorescent antibody stain having a second fluorescent emission response to the excitation radiation that is different than the first fluorescent emission response; and
the flow cytometry comprises second detecting for second radiation from the flow cell within a wavelength range of the second fluorescent emission and evaluating the detected second radiation for detection events indicative of passage through the flow cell of the second unassociated labeled particles of virus size including a particle of virus size with the second epitope and the second fluorescent antibody stain.

9B. A flow cytometry method according to example implementation combination 8B, wherein the particles of virus size with the second epitope comprise virus-like particles.

10B. A flow cytometry method according to either one of example implementation combination 8B or example implementation combination 9B, wherein the second viral type is selected from the group consisting of rhabdovirus viral type and norovirus viral type.

11B. A flow cytometry method according to any one of example implementation combinations 1B-6B, wherein the epitope is a first epitope, the flow cytometry is first flow cytometry, the fluid sample is a first fluid sample including a first portion of the of the biological material sample, the unassociated labeled particles are first unassociated labeled particles and the excitation radiation is first excitation radiation, and the method comprises:
subjecting to flow cytometry a second fluid sample comprising a second portion of the biological material sample, wherein the fluid sample comprises a second fluorescent antibody stain that is different than the first fluorescent antibody stain and is capable of binding, directly or indirectly, with a second epitope that is different than the first epitope, the second epitope being indicative of a second viral type other than baculovirus and the second flow cytometry comprising:
flowing the second fluid sample through a flow cell of a flow cytometer;
subjecting the second fluid sample flowing through the flow cell to second excitation radiation, which is the same as or different than the first excitation radiation, capable of causing a second fluorescent emission response that is different than the first fluorescent emission response from the second fluorescent antibody stain; and
detecting radiation from the flow cell within a wavelength range of the fluorescent emission and evaluating the detected radiation to identify detection events indicative of passage through the flow cell of second unassociated labeled particles of virus size including a particle of virus size with the second epitope and the second fluorescent antibody stain.

12B. A flow cytometry method according to example implementation combination 11B, wherein:
the first and second fluid samples each includes at least two different fluorescent antibody stains for binding, directly or indirectly, with two different epitopes; and
the first and second fluid samples each includes at least one fluorescent antibody stain that is not in the other said fluid sample.

13B. A flow cytometry method according to example implementation combination 12B, wherein the at least two fluorescent antibody stains of each said fluid sample are targeted to detecting at least two different types of particles of virus size in the said fluid sample and at least one said type of particle is different between the first sample fluid and the second sample fluid.

14B. A flow cytometry method according to any one of example implementation combinations 1B-13B, wherein the biological material sample is a sample collected from a stage of a production operation for producing baculovirus particles during which the virus-size particles of a baculovirus viral type are expected to be present in the biological material.

15B. A flow cytometry method for manufacturing a product comprising virus-size particles of a baculovirus viral type, the method comprising:
production processing to prepare a purified product including the virus-size particles of the baculovirus viral type, the production processing including:
generating the virus-size particles in a biological production operation;
harvesting from the biological production operation crude product comprising the virus-size particles generated during the generating;
purifying at least a portion of material of the crude product to prepare a purified product including the virus-size particles;
collecting a biological material sample from a stage of the production processing during which the virus-size particles would be expected to be present in the biological material;
evaluating the sample for presence of particles of virus size having an epitope indicative of baculovirus viral type, the evaluating comprising performing the method according to any one of example implementation combinations 1B-13B.

16B. A flow cytometry method according to example implementation combination 15B, comprising performing the collecting multiple times to collect different said biological material samples to be evaluated from multiple different said stages and performing a said evaluating on each said collected biological material sample to be evaluated.

17B. A flow cytometry method according to example implementation combination 16B, wherein the multiple different said stages include at least a first stage during the generating or the harvesting and a second stage during or after the purifying.

18B. A flow cytometry method according to any one of example implementation combinations 1B-17B, wherein the biological material in the fluid sample is purified biological material with larger-size components removed to a filtration size of not larger than 2 microns.

19B. A flow cytometry method according to any one of example implementation combinations 1B-18B, wherein a said fluid sample as fed to the flow cytometer has a concentration of the unassociated labeled particles in a range of from $1\times10^5$ to $1\times10^9$ particles per milliliter.

20B. A flow cytometry method according to any one of example implementation combinations 1B-19B, wherein a said fluorescent antibody stain comprises fluorophore attached to antibody molecules and the fluorescent antibody stain in the fluid sample comprises an average of from 3 to 8 of the fluorophores attached per said antibody molecule.

21B. A flow cytometry method according to any one of example implementation combinations 1B-20B, wherein antibody of the fluorescent stain is monoclonal.

22B. A flow cytometry method according to any one of example implementation combinations 1B-21B, wherein the flow cytometry comprises flowing a said fluid sample through the flow cell at a fluid sample flow rate in a range of from 250 to 3000 nanoliters per minute.

23B. A flow cytometry method according to any one of example implementation combinations 1B-22B comprising:
preparing the fluid sample, comprising mixing biological material to be evaluated for presence of the unassociated virus-size particles with the fluorescent antibody stain.

24B. A flow method according to example implementation combination 23B, wherein the preparing the fluid sample comprises, prior to the mixing, purifying a crude sample of biological material to prepare the biological material for the fluid sample as subjected to the flow cytometry, the purifying comprising filtering out particles of the crude sample at a filtration size of not larger than 2 microns and comprising spin chromatography in a centrifuge to remove at least a portion of impurities smaller than virus size.

25B. A flow cytometry method according to either one of example implementation combination 23B or example implementation combination 24B, wherein the preparing a fluid sample comprises, after the mixing, not removing fluorescent antibody stain not bound in the unassociated labeled particles from the fluid sample prior to the flow cytometry.

26B. A flow cytometry method according to any one of example implementation combinations 23B-25B, wherein the fluorescent antibody stain comprises a biotinylated antibody and a fluorophore conjugated streptavidin.

27B. A flow cytometry method according to example implementation combination 26B, wherein the fluorophore conjugated streptavidin is attached to the biotinylated antibody when provided to the mixing.

28B. A flow cytometry method according to example implementation combination 27B, wherein the fluorophore conjugated streptavidin and the biotinylated antibody are provided in separate formulations to the mixing and the fluorophore conjugated streptavidin attaches to the biotinylated antibody in solution during the mixing.

29B. A flow cytometry method according to any one of example implementation combinations 1B-28B, wherein the flow cytometry is in the absence of detecting for light scatter.

30B. A flow cytometry method according to example implementation combination 3B, wherein the fluid sample as fed to the flow cytometer has a concentration of the unassociated labeled particles in a range of from $1\times10^5$ to $1\times10^9$ particles per milliliter.

31B. A flow cytometry method according to example implementation combination 30B, wherein the fluorescent antibody stain comprises fluorophore attached to antibody molecules and the fluorescent antibody stain in the fluid sample comprises an average of from 3 to 8 of the fluorophores attached per said antibody molecule.

32B. A flow cytometry method according to example implementation combination 31B, wherein the fluorescent antibody stain is a first fluorescent stain and the fluid sample comprises a second fluorescent stain having a second fluorescent emission response, different than the first fluorescent emission response of the first fluorescent stain, caused by the excitation radiation.

33B. A flow cytometry method according to example implementation combination 32B, wherein the second fluorescent stain comprises a fluorescent nucleic acid stain not specific to particle type.

34B. A flow cytometry method according to example implementation combination 32B, wherein:
the unassociated labeled particles are first unassociated labeled particles, the epitope is a first epitope, the virus-size particles are of a first virus-size particles, the baculovirus viral type is a first viral type and the unassociated labeled particles are first unassociated labeled particles;
the second fluorescent stain is a second fluorescent antibody stain that is different than the first fluorescent antibody stain and is capable of binding with second virus-size particles having a second epitope indicative of a second viral type that is different than the first viral type to form second unassociated labeled particles of virus size; and
the method comprises detecting radiation from the flow cell within a wavelength range of the second fluorescent emission and evaluating the detected radiation to identify detection events indicative of passage of the second unassociated labeled particles through the flow cell.

35B. A flow cytometry method according to example implementation combination 34B, wherein the second fluorescent emission has a peak wavelength at least 20 nanometers different than a peak wavelength of the first fluorescent emission nanometers and the flow cytometry comprises separately detecting for at least the first and second fluorescent emissions and not detecting for light scatter.

36B. A flow cytometry method according to example implementation combination 35B, wherein the second virus-size particles comprise virus-like particles of the second viral type.

37B. A flow cytometry method according to example implementation combination 31B, wherein the epitope is baculovirus gp64 envelope glycoprotein and the fluorescent antibody stain comprises AcV1 monoclonal antibody.

38B. A flow cytometry method according to any one of example implementation combinations 30B-37B, wherein the virus-size particles comprise baculovirus modified to express recombinant protein.

39B. A flow cytometry method according to example implementation combination 38B, wherein the flow cytometry is in the absence of detecting for light scatter.

40B. A flow cytometry method according to example implementation combination 38B, comprising preparing the fluid sample, the preparing the fluid sample comprising:
mixing biological material to be evaluated for presence of the unassociated virus-size particles with the fluorescent antibody stain; and
after the mixing, not removing fluorescent antibody not bound in the unassociated labeled particles from the fluid sample prior to flow cytometry 41B. A fluid sample for feed to a flow cytometer for flow cytometry evaluation, comprising;
an aqueous liquid medium;
unassociated labeled particles of virus size in the aqueous liquid medium at a concentration of from $1\times10^5$ to $1\times10^9$ of the unassociated labeled particles per milliliter, wherein the unassociated labeled particles each includes a virus-size particle of a baculovirus viral type having an epitope indicative of the baculovirus viral type and a fluorescent antibody stain specific for binding, directly or indirectly with the epitope; and
a concentration of the unbound fluorescent antibody stain in the aqueous liquid medium, not bound in the unassociated labeled particles, in a range of from 0.5 microgram per milliliter to 10 micrograms per milliliter.

42B. A fluid sample according to example implementation combination 41B, wherein the fluid sample includes a total concentration of the fluorescent antibody stain in a range of from 0.5 microgram per milliliter to 10 micrograms per milliliter.

43B. A fluid sample according to either one of example implementation combination 41B or example implementation combination 42B, wherein the biological material in the fluid sample is purified biological material with larger-size components removed to a filtration size of not larger than 2 microns.

44B. A fluid sample according to any one of example implementation combinations 41B-43B, wherein the unassociated labeled particles have a maximum cross dimension of not larger than 600 nanometers.

45B. A fluid sample according to any one of example implementation combinations 41B-44B, wherein the fluorescent antibody stain comprises fluorophore attached to antibody molecules and the fluorescent antibody stain in the fluid sample comprises an average of 3 to 8 of the fluorophores attached per antibody molecule.

46B. A fluid sample according to any one of example implementation combinations 41B-45B, wherein antibody of the antibody stain is monoclonal.

47B. A fluid sample according to any one of example implementation combinations 41B-46B, wherein the virus-size particles comprise baculovirus modified to express recombinant protein.

48B. A fluid sample according to any one of example implementation combinations 41B-47B, wherein the epitope is baculovirus gp64 envelope glycoprotein and the fluorescent antibody stain comprises AcV1 monoclonal antibody.

49B. A fluid sample according to any one of example implementation combinations 41B-48B, wherein the fluorescent antibody stain comprises a biotinylated antibody and a fluorophore conjugated streptavidin.

50B. A fluid sample according to any one of example implementation combinations 41B-49B, wherein:
the fluorescent antibody stain is a first fluorescent stain having a first fluorescent emission; and
the fluid sample includes a second fluorescent stain for nucleic acid, the second fluorescent stain having a second fluorescent emission, different than the first fluorescent emission.

51B. A fluid sample according to any one of example implementation combinations 41B-49B, wherein:
the fluorescent antibody stain is a first fluorescent antibody stain, the epitope is a first epitope, the fluorescent emission is a first fluorescent emission, the viral type is a first viral type and the unassociated labeled particles are first unassociated labeled particles of virus size;

the fluid sample includes a second fluorescent antibody stain different than the first fluorescent antibody stain and capable of binding, directly or indirectly, with a second epitope different than the first epitope, the second epitope being indicative of a second viral type that is other than baculovirus and the second fluorescent antibody stain having a second fluorescent emission response that is different than the first fluorescent emission response.

52B. A fluid sample according to example implementation combination 51B, wherein the particle of virus size with the second epitope is a virus-like particle.

53B. A fluid sample according to either one of example implementation combination 51B or example implementation combination 52B, wherein the second viral type is selected from the group consisting of rhabdovirus viral type and norovirus viral type.

54B. A fluid sample according to example implementation combination 42B, wherein the fluorescent antibody stain comprises fluorophore attached to antibody molecules and the fluorescent antibody stain in the fluid sample comprises an average of 3 to 8 of the fluorophores attached per antibody molecule.

55B. A fluid sample according to example implementation combination 54B, wherein the fluorescent antibody stain comprises a biotinylated antibody and a fluorophore conjugated streptavidin.

56B. A fluid sample according to example implementation combination 54B, wherein:
the fluorescent antibody stain is a first fluorescent stain having a first fluorescent emission; and
the fluid sample includes a second fluorescent stain for nucleic acid, the second fluorescent stain having a second fluorescent emission, different than the first fluorescent emission.

57B. A fluid sample according to example implementation combination 54B, wherein:
the fluorescent antibody stain is a first fluorescent antibody stain, the epitope is a first epitope, the fluorescent emission is a first fluorescent emission, the viral type is a first viral type and the unassociated labeled particles are first unassociated labeled particles of virus size;
the fluid sample includes a second fluorescent antibody stain different than the first fluorescent antibody stain and capable of binding, directly or indirectly, with a second epitope different than the first epitope, the second epitope being indicative of a second viral type that is other than baculovirus and the second fluorescent antibody stain having a second fluorescent emission response that is different than the first fluorescent emission response.

58B. A fluid sample according to example implementation combination 57B, wherein the particle of virus size with the second epitope is a virus-like particle.

59B. A fluid sample according to any one of example implementation combinations 54B-58B, wherein the virus-size particles comprise baculovirus modified to express recombinant protein.

60B. A fluid sample according to example implementation combination 59B, wherein the epitope is baculovirus gp64 envelope glycoprotein and the fluorescent antibody stain comprises AcV1 monoclonal antibody.

1C. A method according to any one of example implementation combinations 1-114 and 1B-40B, wherein the flow cytometry comprises:
counting the detection events as occurrences of individual ones of the unassociated labeled particles passing through the flow cell to determine a count for unassociated labeled particles in a volume of the fluid sample passing through the flow cell;
determining the volume of fluid sample passing through the flow cell that corresponds with the count; and
determining a concentration of the unassociated labeled particles in the volume of the fluid sample passing through the flow cell using the count of unassociated labeled particles.

2C. A method according to example implementation combination 1C, wherein the flow cytometry comprises:
performing the counting of a said unassociated labeled particle in real time relative to the detecting of the radiation corresponding with the detection event; and
determining the concentration in real time relative to passage of the volume of the fluid sample through the flow cell.

3C. A method according to either one of example implementation combination 1C or example implementation combination 2C, wherein the determining the volume of fluid sample passing through the flow cell comprises measuring in real time with a flow sensor the flow rate of the fluid sample to the flow cell and integrating resulting measured flow rate data over time.

4C. A method according to any one of example implementation combination 1C-3C, wherein the identification of detection events indicative of passage through the flow cell of the unassociated labeled particles is determined in the absence of correlating with light scatter detection information.

The foregoing discussion of the invention and different aspects thereof has been presented for purposes of illustration and description. The foregoing is not intended to limit the invention to only the form or forms specifically disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Although the description of the invention has included description of one or more possible embodiments and certain variations and modifications, other variations and modifications are within the scope of the invention, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described or claimed with respect to any disclosed variation may be combined in any combination with one or more of any other features of any other variation or variations, to the extent that the features are not necessarily technically compatible, and all such combinations are within the scope of the present invention. The description of a feature or features in a particular combination do not exclude the inclusion of an additional feature or features. Processing steps and sequencing are for illustration only, and such illustrations do not exclude inclusion of other steps or other sequencing of steps. Additional steps may be included between illustrated processing steps or before or after any illustrated processing step.

The terms "comprising", "containing", "including" and "having", and grammatical variations of those terms, are intended to be inclusive and nonlimiting in that the use of such terms indicates the presence of some condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or the appropriate grammatical variation of such narrower terms). For example, a statement that something "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term at "at least a portion" means all or a portion that is less than all. The term "at least a part" means all or a part that is less than all.

A "portion" or a material, e.g., of a biological material sample, refers to some component or components of such material and includes both equal composition aliquots of a material and processed portions of the material that no longer have the same composition but that have one or more components from the material and which may be mixed with other components (e.g., buffer solution, reagents) not from the material. For example, a fluid sample including biological material that is to be subjected to flow cytometry includes a portion of a collected crude biological material sample even if the fluid sample includes only some purified biological components separated from the crude sample. As another example, if a batch of fluid sample is prepared including some biological material for evaluation is divided into separate aliquots for separate flow cytometry runs of the individual aliquots, each such aliquot includes both a portion of the biological material of the batch and includes a portion of the biological material that originated from a crude sample of biological material that may have been subjected to purification.

What is claimed is:

1. A flow cytometry method for evaluating a biological material sample for the presence of unassociated virus-size particles having a target epitope, the method comprising:
   subjecting to flow cytometry a fluid sample comprising at least a portion of the biological material sample and a fluorescent antibody stain with an antibody targeted to bind, directly or indirectly, with the target epitope to form unassociated labeled particles of virus size, the unassociated labeled particles including a said virus-size particle fluorescently labeled with the fluorescent antibody stain, the flow cytometry comprising:
   flowing the fluid sample through a flow cell of a flow cytometer;
   subjecting the fluid sample flowing through the flow cell to excitation radiation capable of causing a fluorescent emission response from the fluorescent antibody stain; and
   detecting radiation from the flow cell within a wavelength range of the fluorescent emission response and evaluating the detected radiation to identify detection events indicative of passage through the flow cell of the unassociated labeled particles; and
   the fluorescent antibody stain being a first fluorescent stain and the fluid sample comprising a second fluorescent stain, different than the first fluorescent stain, comprising a fluorogenic nucleic acid stain.

2. The method of claim 1, wherein the fluid sample as fed to the flow cytometer includes a concentration of unbound said fluorescent antibody stain, not bound in the unassociated labeled particles, in a range of from 0.5 microgram per milliliter to 10 micrograms per milliliter.

3. The method of claim 1, comprising:
   preparing the fluid sample, comprising mixing the at least a portion of the biological material with the fluorescent antibody stain and, after the mixing, not removing unbound said fluorescent antibody stain, not bound in the unassociated labeled particles, from the fluid sample prior to the flow cytometry.

4. The method of claim 1, wherein the flow cytometry is in the absence of particle identification by light scatter detection.

5. The method of claim 1, wherein the unassociated labeled particles have a size with a maximum cross dimension in a range of from 20 nanometers to 1 micron.

6. The method of claim 5, wherein the fluorescent antibody stain comprises a fluorophore attached to an antibody molecule with an average of from 3 to 8 of the fluorophore attached per antibody molecule.

7. The method of claim 1, wherein the unassociated labeled particles have a size with a maximum cross dimension in a range of from 40 nanometers to 600 nanometers.

8. The method of claim 1, wherein the virus-size particles comprise virus-like particles.

9. The method of claim 1, comprising preparing the fluid sample, comprising mixing the at least a portion of the biological material with the fluorescent antibody stain and, after the mixing, not removing unbound said fluorescent antibody stain, not bound in the unassociated labeled particles, from the fluid sample prior to the flow cytometry, and wherein:
   the fluid sample as fed to the flow cytometer includes a concentration of unbound said fluorescent antibody stain, not bound in the unassociated labeled particles, in a range of from 0.5 microgram per milliliter to 10 micrograms per milliliter;
   the flow cytometry is in the absence of particle identification by light scatter detection; and
   the unassociated labeled particles have a size with a maximum cross dimension in a range of from 40 nanometers to 600 nanometers.

10. A flow cytometry method for evaluating a biological material sample for the presence of unassociated virus-size particles having a target epitope, the method comprising:
    subjecting to flow cytometry a fluid sample comprising at least a portion of the biological material sample and a fluorescent antibody stain with an antibody targeted to bind, directly or indirectly, with the target epitope to form unassociated labeled particles of virus size, the unassociated labeled particles including a said virus-size particle fluorescently labeled with the fluorescent antibody stain, the flow cytometry comprising:

flowing the fluid sample through a flow cell of a flow cytometer;

subjecting the fluid sample flowing through the flow cell to excitation radiation capable of causing a fluorescent emission response from the fluorescent antibody stain; and detecting radiation from the flow cell within a wavelength range of the fluorescent emission response and evaluating the detected radiation to identify detection events indicative of passage through the flow cell of the unassociated labeled particles; and the flow cytometry being in the absence of identification of the unassociated labeled particles using light scatter detection.

11. The method of claim 10, wherein the fluid sample as fed to the flow cytometer includes a concentration of unbound said fluorescent antibody stain, not bound in the unassociated labeled particles, in a range of from 0.5 microgram per milliliter to 10 micrograms per milliliter.

12. The method of claim 10, comprising:

preparing the fluid sample, comprising mixing the at least a portion of the biological material with the fluorescent antibody stain and, after the mixing, not removing unbound said fluorescent antibody stain, not bound in the unassociated labeled particles, from the fluid sample prior to the flow cytometry.

13. The method of claim 10, wherein:

the unassociated labeled particles have a size with a maximum cross dimension in a range of from 20 nanometers to 1 micron; and the fluorescent antibody stain comprises a fluorophore attached to an antibody molecule with an average of from 3 to 8 of the fluorophore attached per antibody molecule.

14. The method of claim 10, wherein the virus-size particles comprise virus-like particles.

15. A flow cytometry method for evaluating a biological material sample for the presence of unassociated virus-size particles having a target epitope, the method comprising:

preparing a fluid sample, the preparing the fluid sample comprising mixing biological material to be evaluated for presence of the unassociated particles with a fluorescent antibody stain with an antibody targeted to bind, directly or indirectly, with the target epitope to form unassociated labeled particles of virus size, the unassociated labeled particles including a said virus-size particle fluorescently labeled with the fluorescent antibody stain;

subjecting to flow cytometry the fluid sample, the flow cytometry comprising:

flowing the fluid sample through a flow cell of a flow cytometer;

subjecting the fluid sample flowing through the flow cell to excitation radiation capable of causing a fluorescent emission response from the fluorescent antibody stain; and detecting radiation from the flow cell within a wavelength range of the fluorescent emission response and evaluating the detected radiation to identify detection events indicative of passage through the flow cell of the unassociated labeled particles; and after the mixing, not removing unbound said fluorescent antibody stain, not bound in the unassociated labeled particles, from the fluid sample prior to the flow cytometry.

16. The method of claim 15, wherein the fluid sample as fed to the flow cytometer includes a concentration of the unbound said fluorescent antibody stain in a range of from 0.5 microgram per milliliter to 10 micrograms per milliliter.

17. The method of claim 15, wherein:

the unassociated labeled particles have a size with a maximum cross dimension in a range of from 20 nanometers to 1 micron; and the fluorescent antibody stain comprises a fluorophore attached to an antibody molecule with an average of from 3 to 8 of the fluorophore attached per antibody molecule.

18. The method of claim 15, wherein the virus-size particles comprise virus-like particles.

19. A flow cytometry method for evaluating a biological material sample for the presence of unassociated virus-size particles having a target epitope, the method comprising:

subjecting to flow cytometry a fluid sample comprising at least a portion of the biological material sample and a fluorescent antibody stain with an antibody targeted to bind, directly or indirectly, with the target epitope to form unassociated labeled particles of virus size, the unassociated labeled particles including a said virus-size particle fluorescently labeled with the fluorescent antibody stain, the flow cytometry comprising:

flowing the fluid sample through a flow cell of a flow cytometer;

subjecting the fluid sample flowing through the flow cell to excitation radiation capable of causing a fluorescent emission response from the fluorescent antibody stain; and detecting radiation from the flow cell within a wavelength range of the fluorescent emission response and evaluating the detected radiation to identify detection events indicative of passage through the flow cell of the unassociated labeled particles; and the fluid sample as fed to the flow cytometer comprising a concentration of the fluorescent antibody stain, not bound in the unassociated labeled particles, in a range of from 0.5 microgram per milliliter to 10 micrograms per milliliter.

20. The method of claim 19, wherein the fluid sample as fed to the flow cytometer includes a total concentration of the fluorescent antibody stain in a range of from 0.5 microgram per milliliter to 10 micrograms per milliliter.

* * * * *